US008741849B2

(12) United States Patent
Panitch et al.

(10) Patent No.: US 8,741,849 B2
(45) Date of Patent: Jun. 3, 2014

(54) KINASE INHIBITORS AND USES THEREOF

(75) Inventors: Alyssa Panitch, West Lafayette, IN (US); Brandon Seal, Pleasant Grove, UT (US); Brian Ward, Lebanon, IN (US)

(73) Assignee: Purdue Research Foundation, West Lafayette, IN (US)

( * ) Notice: Subject to any disclaimer, the term of this patent is extended or adjusted under 35 U.S.C. 154(b) by 522 days.

(21) Appl. No.: 12/188,109

(22) Filed: Aug. 7, 2008

(65) Prior Publication Data

US 2009/0149389 A1 Jun. 11, 2009
US 2013/0184221 A9 Jul. 18, 2013

Related U.S. Application Data

(63) Continuation-in-part of application No. 11/972,459, filed on Jan. 10, 2008, now Pat. No. 8,536,303.

(60) Provisional application No. 60/963,941, filed on Aug. 7, 2007, provisional application No. 60/994,970, filed on Sep. 24, 2007, provisional application No. 60/880,137, filed on Jan. 10, 2007.

(51) Int. Cl.
*A61K 38/16* (2006.01)

(52) U.S. Cl.
USPC ....... 514/18.9; 514/19.2; 514/19.3; 514/19.4; 514/19.5; 514/21.4

(58) Field of Classification Search
None
See application file for complete search history.

(56) References Cited

U.S. PATENT DOCUMENTS

| | | |
|---|---|---|
| 4,105,027 A | 8/1978 | Lundquist |
| 4,192,309 A | 3/1980 | Poulsen |
| 4,227,522 A | 10/1980 | Carris |
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,175,144 A | 12/1992 | Walser |
| 5,415,864 A | 5/1995 | Kopecek et al. |
| 5,565,350 A | 10/1996 | Kmiec et al. |
| 6,855,693 B2 | 2/2005 | Mochly-Rosen et al. |
| 6,921,527 B2 | 7/2005 | Platz et al. |
| 7,041,814 B1 | 5/2006 | Weinstock et al. |
| 7,135,453 B2 | 11/2006 | Brophy et al. |
| 7,361,352 B2 | 4/2008 | Birkett et al. |

(Continued)

FOREIGN PATENT DOCUMENTS

| | | |
|---|---|---|
| JP | 2002-505077 | 2/2002 |
| WO | WO 91/16038 | 10/1991 |

(Continued)

OTHER PUBLICATIONS

Colomer et al. Physiological Roles of the Ca2+/CaM-Dependent Protein Kinase Cascade in Health and Disease. Sub-Cellular Biochemistry. 2007, vol. 45, pp. 169-214.*

(Continued)

*Primary Examiner* — Jeffrey E Russel
(74) *Attorney, Agent, or Firm* — Barnes & Thornburg LLP

(57) ABSTRACT

The present invention relates to kinase inhibiting compositions and uses thereof. The invention further provides isolated kinase inhibiting peptides and uses thereof for inhibiting hyperplasia, for inhibiting the growth of neoplasms, and for inducing programmed cell death in a cell population.

21 Claims, 5 Drawing Sheets

(56) References Cited

U.S. PATENT DOCUMENTS

| | | | |
|---|---|---|---|
| 2002/0009491 | A1 | 1/2002 | Rothbard et al. |
| 2002/0041899 | A1 | 4/2002 | Chudzik et al. |
| 2002/0128444 | A1 | 9/2002 | Gingras et al. |
| 2003/0134810 | A1 | 7/2003 | Springate et al. |
| 2003/0187232 | A1 | 10/2003 | Hubbell et al. |
| 2003/0190364 | A1 | 10/2003 | Panitch et al. |
| 2005/0153372 | A1* | 7/2005 | Greengard et al. ............ 435/7.9 |
| 2006/0024264 | A1 | 2/2006 | Kuroda et al. |
| 2006/0035814 | A1 | 2/2006 | Brophy et al. |
| 2006/0115453 | A1* | 6/2006 | Yaffe et al. .................... 424/85.4 |
| 2006/0293234 | A1 | 12/2006 | Schroeder et al. |
| 2007/0026518 | A1 | 2/2007 | Healy et al. |
| 2007/0078092 | A1 | 4/2007 | Livnah et al. |
| 2007/0154448 | A1 | 7/2007 | Reid et al. |
| 2007/0202189 | A1 | 8/2007 | Ahlfors |
| 2008/0038352 | A1 | 2/2008 | Simpson et al. |
| 2008/0113971 | A1 | 5/2008 | Hanau et al. |
| 2008/0132443 | A1 | 6/2008 | Brophy et al. |
| 2008/0293640 | A1* | 11/2008 | Brophy et al. .................. 514/14 |
| 2009/0176694 | A1 | 7/2009 | Brophy et al. |
| 2009/0176695 | A1 | 7/2009 | Brophy et al. |
| 2009/0196927 | A1* | 8/2009 | Panitch et al. ............... 424/484 |
| 2009/0258819 | A1 | 10/2009 | Brophy et al. |
| 2009/0269406 | A1 | 10/2009 | Panitch et al. |
| 2010/0004165 | A1 | 1/2010 | Brophy et al. |
| 2010/0009903 | A1 | 1/2010 | Brophy et al. |
| 2010/0098760 | A1 | 4/2010 | Panitch |
| 2010/0158968 | A1 | 6/2010 | Panitch et al. |
| 2011/0052658 | A1 | 3/2011 | Panitch et al. |
| 2011/0288036 | A1 | 11/2011 | Lander et al. |

FOREIGN PATENT DOCUMENTS

| | | |
|---|---|---|
| WO | WO 93/22443 | 11/1993 |
| WO | 99/29721 A1 | 6/1999 |
| WO | WO 03/018758 | 3/2003 |
| WO | WO 2004/075914 | 9/2004 |
| WO | WO 2004/110337 | 12/2004 |
| WO | WO 2004110337 A2 * | 12/2004 |
| WO | WO 2005/037236 | 4/2005 |
| WO | WO 2005/114221 | 12/2005 |
| WO | WO 2006/071456 | 7/2006 |
| WO | WO 2007/053512 | 5/2007 |
| WO | WO 2008/008772 | 1/2008 |
| WO | WO 2008/085191 | 7/2008 |
| WO | WO 2009/021137 | 2/2009 |
| WO | WO 2009/123759 | 10/2009 |
| WO | WO 2010/065206 | 6/2010 |
| WO | WO 2010/068692 | 6/2010 |
| WO | WO 2011/017132 | 2/2011 |

OTHER PUBLICATIONS

Kwon et al. The cdk2 Binding Domain of p27Kip correlates with the Inhibition of the Kinase Activity . . . Biochemical and Biophysical Research Communications. 1996, vol. 220, No. 3, pp. 703-709.*
Allaire et al. (1997) Ann Thorac Surg 63(2):582-91.
Andrews et al. (1993). "Report of the AVMA panel on Euthanasia." Journal of the American Veterinary Association, 202(2): 229-249.
Auwerx, "The Human Leukemia-Cell Line, Thp-1-a Multifaceted Model for the Study of Monocyte-Macrophage Differentiation," Experientia, 1991, 47, (1), 22-31.
Brennan et al., "Expression in Chronic Inflammatory Disease," British Medical Bulletin, 1995, 51(2), 368-384.
Brophy et al. (1998) J Reprod Fertil 114(2):351-355.
Butler et al., "Use of organotypic coculture to study keloid biology," Am J Surg, 195(2): 144-148, Feb. 2008.
Calderon et al., "Increased proliferation in keloid fibroblasts wounded in vitro," J Surg Res, vol. 61, pp. 343-347, Mar. 1996.
Carpino et al., 1972, J. Org. Chem., 37: 3403-3409.
Carroll et al., "Triamcinolone stimulates bFGF production and inhibits TGF-beta 1 production by human dermal fibroblasts," Dermato Surg, vol. 28, pp. 704-709, Aug. 2002.

Chiu et al., "Photodynamic therapy on keloid fibroblasts in tissue-engineered keratinocyte-fibroblast co-culture," Lasers Surg Med, vol. 37, pp. 231-244, Sep. 2005.
Coumans et al. (2001). "Axonal regeneration and functional recovery after complete spinal cord transection in rats by delayed treatment with transplants and neurotrophins.'" The Journal of Neuroscience, 21(23): 9334-9344.
Dalkowski et al., "Cryotherapy modifies synthetic activity and differentiation of keloidal fibroblasts in vitro," Exp Dermatol, vol. 12, pp. 673-681, Oct. 2003.
Davies et al. (2000) Biochem J 351(Pt 1):95-105.
DeGrado et al. (1999) Annual Review of Biochemistry 68:779-819.
Dreiza et al., "Transducible heat shock protein 20 phosphopeptide alters cytoskeletal dynamics," FASEB J, 19: 261-263: 2004.
Duncan et al. (1999) FASEB J 13(13): 1774-86.
Fawell et al., Proc Natl Acad Sci USA, 1994, 91(2): 664-668.
Feldmann et al., "The role of cytokines in the pathogenesis of rheumatoid arthritis," Rheumatology, 1999, 38, 3-7.
Fields et al., 1990, Int. J. Pept. Protein Res., 35: 161-214.
Firestein et al., "How important are T cells in chronic rheumatoid synovitis? II. T cell-independent mechanisms from beginning to end," Arthritis and Rheumatism 2002, 46, (2), 298-308.
Frankel et al., Cell, 55(6): 1189-1193, 1988.
Fuchs et al. (2000) Am I Physiol Regul Integr Comp Physiol 279(2): R492-8.
Gaestel, Nat. Rev. Mol. Cell. Biol. 7, 120-130, 2006.
Gerthoffer et al. (2001) J Appl Physiol 91:963-972, 2001.
Green et al., Cell, 1988, 55(60: 1179-1188.
Hayess et al., "Effect of protein kinase inhibitors on activity of mammalian small heat-shock protein (HSP25) kinase", *Biochemical Pharmacology*, May 9, 1997, vol. 53, No. 9, 1239-1247.
Hedges et al., J Biol. Chem. 274, 24211-24219, 1999.
Hegen et al., "MAPKAP kinase 2-deficient mice are resistant to collagen-induced arthritis," Journal of Immunology 2006, 177(3), 1913-1917.
Hirano et al., Journal of Surgical Research 102, 77-84, 2002.
Hong et al., "Growth of keloid-producing fibroblasts in commercially available serum-free media," Otolaryngol Head Neck Surg, vol. 121, pp. 469-473, Oct. 1999.
Jenkins et al., "The pathogenesis of rheumatoid arthritis: A guide to therapy," American Journal of the Medical Sciences, 2002, 323(4), 171-180.
Kent et al. (2004) Ann Vasc Surg 18(2): 135-7.
Koch et al., "Serum-free keloid fibroblast cell culture: an in vitro model for the study of aberrant wound healing," in Plast Reconstr Surg., vol. 99, 1997, pp. 1094-1098.
Kossi et al., "Different metabolism of hexose sugars and sucrose in wound fluid and in. fibroblast cultures derived from granulation tissue, hypertrophic scar and keloid," Pathobiology; vol. 68, pp. 29-35, Jan.-Feb. 2000.
Kotlyarov et al., "MAPKAP kinase 2 is essential for LPS-induced TNF-alpha biosynthesis," Nature Cell Biology, 1999, 1(2).
Kumar et al., "p38 map kinases: Key signaling molecules as therapeutic targets for inflammatory diseases," Nature Reviews Drug Discovery, 2003, 2, (9), 717-726.
Lavoie et al., J Biol. Chem. 268, 24210-24214, 1993.
Lavoie et al., Mol Cell Biol. 15: 505-516, 1995.
Macomson et al. (2002) Neurosurgery 51(1): 204-10; discussion 210-1.
Mann et al. (1999) Lancet 354(9189): 1493-8.
Matsuoka et al., "Ultrastructural characteristics of keloid fibroblasts," Am J Dermatopathol, vol. 10, pp. 505-508, Dec. 1988.
McLemore et al. (2005) J Am Coll Surg 201(1): 30-6.
Neidigh et al. (2002) Nature Structural Biology 9(6): 425-430.
Pincus et al., "What Is the Natural-History of Rheumatoid-Arthritis," Rheumatic Disease Clinics of North America, 1993, 19, (1), 123-151.
Pinol et al., "Effect of minoxidil on DNA synthesis in cultured fibroblasts from healthy skin or keloids," Med Cutan Ibero Lat Am, vol. 18, pp. 13-17, 1990.
Podolin et al., "Attenuation of murine collagen-induced arthritis by a novel, potent, selective small molecule inhibitor of I kappa B kinase 2, TPCA-1 (2-[(aminocarbonyl)amino]-5-(4-fluorophenyl)-3-thiophenecarboxamide), occurs via reduction of proinflammatory

(56) References Cited

OTHER PUBLICATIONS cytokines and antigen-induced T cell proliferation," Journal of Pharmacology and Experimental Therapeutics, 2005, 312, (1), 373-381.
Polo et al., "Effect of TGF-beta2 on proliferative scar fibroblast cell kinetics," Ann Plast Surg, vol. 43, pp. 185-190, Aug. 1999.
Powell et al. (2003) Molecular and Cellular Biology, 23(15) 5376-5387.
Ross et al., "High-content screening analysis of the p38 pathway: Profiling of structurally related p38 alpha kinase inhibitors using cell-based assays," Assay and Drug Development Technologies, 2006, 4, (4), 397-409.
Russel et al., "The effect of histamine on the growth of cultured fibroblasts isolated from normal and keloid tissue," J Cell Physiol, vol. 93, pp. 389-393, Dec. 1977.
Sahara et al., "Suppression of in vitro proliferative scar fibroblast contraction by interferon alfa-2b," Wound Repair Regen, vol. 1, pp. 22-27, Jan. 1993.
Saklatvala, "The p38 MAP kinase pathway as a therapeutic target in inflammatory disease," Current Opinion in Pharmacology, 2004, 4, (4), 372-377.
Schwarze et al., Science, 1999, 285(54339: 1569-1572.
Seal et al., Biomacromolecules, 2003, 4: 1572-1582.
Sestier et al., "In vitro toxicity of magnetic fluids evaluated for macrophage cell lines," Journal of Magnetism and Magnetic Materials, 2002, 252, (1-3), 403-405.
Silver et al., "Regeneration beyond the glial scar," Nature Reviews Neuroscience, 2004. 5(2): p. 146-156.
Takemura et al., "Evaluation of a human monocytic cell line THP-1 model for assay of the intracellular activities of antimicrobial agents against *Legionella pneumophila*," Journal of Antimicrobial Chemotherapy, 2000, 46, (4), 589-594.
Tessier et al. (2004)J Vasc Surg 40(1): 106-14.
Tyagi et al., J Biol Chem., 2001, 276(5): 3254-3261.
Verlardo et al., "Patterns of Gene Expression Reveal a Temporally Orchestrated Wound Healing Response in the Injured Spinal Cord," J. Neurosci.: 2004. 24(39): p. 8562-8576.
Vincent et al., "Human Skin Keloid Fibroblasts Display Bioenergetics of Cancer Cells," J Invest Dermatol, 128(3): 702-709, Mar. 2008.
Wang et al., "Construction of animal models of keloid by tissue engineering," Di Yi Jun Yi Da Xue Xue Bao, vol. 25, pp. 815-819, 832, Jul. 2005.
Woerly et al. (2001). "Spinal cord reconstruction using Neurogel™ Implants and functional recovery after chronic injury." Journal of Neuroscience Research, 66: 1187-1197.
Xia et al., "Increased CCN2 transcription in keloid fibroblasts requires cooperativity between AP-1 and SMAD binding sites," Ann Surg, vol. 246, pp. 886-895, Nov. 2007.
Xia et al., "P38 MAP kinase mediates transforming growth factor-beta2 transcription in human keloid fibroblasts," Am J Physiol Regul Integr Comp Physiol, vol. 290, pp. R501-R508, Mar. 2006.
Xu et al., Oncogene 25, 2987-2998, 2006.
Yamanishi et al., "Regulation of joint destruction and inflammation by p53 in collagen-induced arthritis," American Journal of Pathology 2002, 160, (1), 123-130.
Yamboliev et al., Am. J Physiol. Heart Circ Physiol., 278, H1899-1907, 2000.
Yang et al., "Establishment of an animal model of human hyperplastic scar in nude mice," Zhonghua Shao Shang Za Zhi, vol. 20, pp. 82-84, Apr. 2004.
Yang et al., "Early expression and cellular localization of proinflammatory cytokines interleukin-1 beta, interleukin-6, and tumor necrosis factor-alpha in human traumatic spinal cord injury," Spine, 2004. 29(9): p. 966-71.
Zong, X., et al., "Prevention of postsurgery-induced abdominal adhesions by electrospun bioabsorable nanofibrous poly(lactide-co-clucolide)-based membranes," Am. Surg., 2004, 240(5): p. 910-5.
Colomer, Sub-Cellular Biochemistry, 2007, 45: 169-214.
Abergel et al., "Biochemical composition of the connective tissue in keloids and analysis of collagen metabolism in keloid fibroblast cultures," J Invest Dermatol, vol. 84, pp. 384-390, May 1985.

Achari et al., 1997, J Polym Sci A: Polym Chem, 35: 2513-2520.
Altschul et al., Nucleic Acids Res. 25:3389-3402 (1997).
Amano et al., "Formation of Actin Stress Fibers and Focal Adhesions Enhanced by RhoKinase", Science, Feb. 28, 1997, vol. 275, No. 5304, 1308-1311.
Andrew et al., "Spinothalamic lamina I neurons selectively sensitive to histamine: a central neural pathway for itch," Nature Neuroscience, 2001.4(1): p. 72-77.
Bareyre et al., "Inflammation, degeneration and regeneration in the injured spinal cord: insights from DNA microarrays," Trends Neurosci, 2003, 26(10): p. 555-63.
Barone et al., "Inhibition of p38Mitogen-Activated Protein Kinase Provides Neuroprotection in Cerebral Focal Ischemia", Med Res. Rev., 2001, vol. 21, No. 2, 129-145.
Beutler, 1999; J. Rheumatol., 26:16-21.
Buckenmaier, C.C., 3rd, et al., "Comparison of antiadhesive treatments using an objective rat model," Am. Surg., 1999, 65(3): 274-82.
Choi, et al., 2005, Angewandte Chemie, 44(41): 6685-6689.
Claverie et al., Comput. Chem., 17:191-201 (1993).
Clowes et al. (1991) J Vasc Surg, 13(6):885-91.
Corpet, et al., Nucleic Acids Research, 16:10881-90 (1988).
DeMarzo et al., "Prostate stem cell compartments: expression of the cell cycle inhibitor p27Kip1 in normal, hyperplastic, and neoplastic cells", Am. J. Pathol., Sep. 1998, vol. 153, No. 3, 911-919.
Feldmann et al., "Role of cytokines in rheumatoid arthritis," Annual Review of Immunology, 1996, 14, 397-440.
Fisher et al., 1994, Macromol Chem Phys, 195: 679-687.
Fragonas et al., "Aricular cartilage repair in rabbits by using suspensions of allogenic chondrocytes in alginate," Biomaterials, 2000, 21(8):795-801.
Fuchs et al. (1997) J Hypertens 15(3): 301-307.
Gaestel et al., "Protein kinases as small molecule inhibitor targets in inflammation," Current Medicinal Chemistry, 2007, 14 (21): 2214-2234.
Gu et al., 2002, J Appl Poly Sci, 86: 3412-3419.
Haapasalo et al., "Truncated trkB.T1 is dominant negative inhibitor of trkB.Tk+-mediated cell survival", Biochem Biophys Res Commun, Feb. 9, 2001, vol. 280, No. 5, 1352-1358 (Abstract only).
Hanasono et al., "Autocrine growth factor production by fetal, keloid, and normal dermal fibroblasts," Arch Facial Plast Surg, vol. 5, pp. 26-30, Jan.-Feb. 2003.
Henikoff et al. (1992) Proc. Natl. Acad. Sci. USA 89:10915-10919).
Higgins et al., Cabios, 5:151-153 (1989).
Higgins et al., Gene, 73:237-244 (1988).
Ho et al., "Synthetic Protein Transduction Domains: Enhanced Transduction Potential in Vitro and in Vivo," *Cancer Research*, 2001, 61: 474-477.
Hruby, V. J. (2002) Nat Rev Drug Discov 1(11): 847-58.
Huang, et al., Computer Applications in the Biosciences 8:155-65 (1992).
Iwasaki et al ., "Effect of transforming growth factor beta 1 on spinal motor neurons after axotomy," J Neurol Sci, 1997, 147(1): 9-12.
Jacovella, Long-lasting results with hydroxylapatite (Radiesse) facial filler, Plastic and Reconstructive Surgery, 2006, 118(3S):15S-21S.
Jobanputra et al., Colorectal Dis. Oct. 2007; 9 Suppl 2: 54-9.
Johnson et al. (2004) Nature Biotech 22(9):1093-1094.
Karlin et al., Proc. Natl. Acad. Sci. USA 90:5873-5787 (1993).
Knoepp et al. (2000) J Vasc Surg 31:343-353.
Koonin et al., "Origin and evolution of eukaryotic apoptosis: the bacterial connection", Cell Death Differ, Apr. 2002, vol. 9, No. 4, 394-404.
Kwon et al., "The cdk2 Binding Domain of p27Kip Correlates with the Inhibition of the Kinase Activity of cdk2/Cyclin Complexes", Biochem Biophys Res Comm, 1996, vol. 220, 703-709.
Langer, 1990 Science 249, 1527-1533.
Liu et al., De novo design, synthesis, and characterization of antimicrobial beta-peptides, J Am Chem Soc, 2001, 123(31): 7553-7559.
LoGerfo et al. (1984) Arch Surg 119:1212-1214.
Lopes et al., "Inhibition of HSP27 phosphorylation by a cell-permeant MAPKAP Kinase 2 inhibitor", *Biochemical and Biophysical Research Communcations*, May 8, 2009, vol. 382, No. 3, 535-539.

(56) References Cited

OTHER PUBLICATIONS

Marijnissen et al., "Tissue-engineered cartilage using serially passaged articular chondrocytes. Chondrocytes in alginate, combined in vivo with a synthetic (E210) or biologic degradable carrier (DBM)," Biomaterials, 2000, 21(6):571-580.
McCormack et al., "The effect of copper tripertide and tretinoin on growth factor production in a serum-free fibroblast model," Arch Facial Plast Surg, vol. 3, pp. 28-32, Jan.-Mar. 2001.
Merrifield, 1963, J. Am. Chem. Soc., 85: 2149-2154.
Meyers et al., Computer Applic. Biol. Sci., 4:11-17 (1988).
Mosse et al. (1985) Lab Invest 53(5): 556-62.
Needleman et al., J. Mol. Biol., 48: 443 (1970).
Pearson et al., Methods in Molecular Biology, 24: 307-331 (1994).
Pearson et al., Proc. Natl. Acad. Sci., 85: 2444 (1988).
Pineau et al., Proinflaminatory cytokine synthesis in the injured mouse spinal cord: multiphasic expression pattern and identification of the cell types involved,: J Comp Neurol, 2007, 500(2): p. 267-285.
Ridley et al., "Actions of 11-1 are Selectively Controlled by P38 Mitogen-Activated Protein Kinase: regulation of prostaglandin H synthase-2, metalloproteinases, and IL-6 at different levels", *J. Immunol.*, 1997, vol. 158, 3165-3173.
Sawhney et al., Macromolecules (1993) 26, 581-587.
Schenk et al., Signal perception and transduction: the role of protein kinases, *Biochemica et Biophyica Acta*, 1999, vol. 1449, 1-24.
Shi et al. (2002) Biol Chem 383:1519-1536 , 2002.
Smith and Waterman, Adv. Appl. Math., 2:482 (1981).
Sousa et al. (2007) J Cell Biochem 100(6):1581-1592.
Stokoe, Biochem. J., 1993, 296 (Pt 3): 843-849.
Tanaka et al., 1976, Bulletin of the Chemical Society of Japan, 49(10): 2821-2823.
Tang et al., Synthesis of urea oligomers and their antibacterial activity, Chem Commun, 2005, 1537-1539.
Terashima et al. (2002) J Am Coll Cardiol 39:228A.
Tew et al., De novo design of biomimetic antimicrobial polymers, PNAS, 2002, 99(8): 5110-5114.
Tapash et al., Transdermal and Topical Drug Delivery, pp. 249-297 (1997).
Vassalli, 1992, Annu. Rev. Immunol., 10:411-452.
Violette et al., Mimicking helical antibacterial peptides with nonpeptidic folding oligomers, Chemistry and Biology, 2006, 13(5): 531-538.
Wang et al., "p27Kip1 overexpression causes apoptotic death in mammalian cells", Oncogene, Dec. 11, 1997, vol. 15, No. 24, 2991-2997.
Ward et al., "Design of a bioactive cell-penetrating peptide: when a transduction domain does more than transduce", *Journal of Peptide Science*, Oct. 2009, vol. 15, No. 10, 668-674.
Weibel et al., Am. J. Surg. 1973; 126: 345-53.
Wooten et al., Comput. Chem., 17: 149-163 (1993).
Worm et al., "Aberrant p27Kip1 promoter methylation in malignant melanoma", Oncogene, Oct. 19, 2000, vol. 19, No. 44, 5111-5115.
Biomol International (online), Kinase Inhibitors. 2006, retrieved from http://www.biomol.com/Online_Catalog/Online_Catalog/Products/36/?search=&mode=product&lastSort=&all=true&categoryId=714. (catalog available upon request).
Biomol International (online), Kinases. 2006, retrieved from http://www.biomol.com/Online_Catalog/Online_Catalog/Products/36/?search=&mode=product&lastSort=&all=true&categoryId=713. (catalog available upon request).
Schindler et al., Examination of the kinetic mechanism of mitogen-activated protein kinase activated protein kinase-2, Biochimica et Biophysica Acta, Jul. 29, 2002, 1598(1-2): 88-97.
Burgess et al., J of Cell Bio., 1990, 111: 2129-2138.
Bowie et al., Science, 1990, 247: 1306-1310.
Pawson et al., Science, 2003, 300: 445-452.
Zhongshu Song et al., "Fusarin C biosynthesis in Fusarium moniliforme and Fusarium venenatum," Chembiochem, 2004, 5(9): 1196-1203.

\* cited by examiner

KINASE INHIBITORS AND USES THEREOF

CROSS REFERENCE TO RELATED APPLICATIONS

This application claims the benefit of U.S. Patent Applications 60/963,941, filed Aug. 7, 2007, and 60/994,970, filed Sep. 24, 2007, each of which is incorporated by reference in its entirety herein. This application is a continuation-in-part application of U.S. application Ser. No. 11/972,459, filed Jan. 10, 2008, which claims priority to U.S. Provisional Application Ser. No. 60/880,137, filed Jan. 10, 2007.

STATEMENT OF GOVERNMENT FUNDING

This invention was made with government support under NIH/NHLBI Grant Number HLO74968 awarded by the National Institute of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 26, 2011, is named 12188109_CFR.txt and is 148,575 bytes in size.

FIELD OF THE INVENTION

The invention relates to cell biology, uses of kinase inhibiting peptides and nucleic acids which encode peptides, and therapeutic methods of use thereof.

BACKGROUND

Kinases

Kinases are a ubiquitous group of enzymes that catalyze the phosphoryl group transfer reaction from a phosphate donor (usually ATP) to a receptor substrate. Although all kinases catalyze essentially the same phosphoryl transfer reaction, they display remarkable diversity in their substrate specificity, structure, and the pathways in which they participate. A recent classification of all available kinase sequences (approximately 60,000 sequences) indicates that kinases may be grouped into 25 families of homologous proteins. These kinase families are assembled into 12 fold groups based on similarity of structural fold. 22 of the 25 families (approximately 98.8% of all sequences) belong to 10 fold groups for which the structural fold is known. Of the other 3 families, polyphosphate kinase forms a distinct fold group; the 2 remaining families are both integral membrane kinases and comprise the final fold group. These fold groups not only include some of the most widely spread protein folds, such as Rossmann-like fold, ferredoxin-like fold, TIM-barrel fold, and antiparallel β-barrel fold, but also all major classes (all α, all β, α+β, α/β) of protein structures. Within a fold group, the core of the nucleotide-binding domain of each family has the same architecture, and the topology of the protein core is either identical or related by circular permutation. Homology between the families within a fold group is not implied.

Group I (23,124 sequences) kinases incorporate protein S/T-Y kinase, atypical protein kinase, lipid kinase, and ATP grasp enzymes and further comprise the protein S/T-Y kinase, and atypical protein kinase family (22,074 sequences). These kinases include: choline kinase (EC 2.7.1.32); protein kinase (EC 2.7.137); phosphorylase kinase (EC 2.7.1.38); homoserine kinase (EC 2.7.1.39); I-phosphatidylinositol 4-kinase (EC 2.7.1.67); streptomycin 6-kinase (EC 2.7.1.72); ethanolamine kinase (EC 2.7.1.82); streptomycin 3'-kinase (EC 2.7.1.87); kanamycin kinase (EC 2.7.1.95); 5-methylthioribose kinase (EC 2.7.1.100); viomycin kinase (EC 2.7.1.103); [hydroxymethylglutaryl-CoA reductase (NADPH$_2$)] kinase (EC 2.7.1.109); protein-tyrosine kinase (EC 2.7.1.112); [isocitrate dehydrogenase (NADP+)] kinase (EC 2.7.1.116); [myosin light-chain] kinase (EC 2.7.1.117); hygromycin-B kinase (EC 2.7.1.119); calcium/calmodulin-dependent protein kinase (EC 2.7.1.123); rhodopsin kinase (EC 2.7.1.125); [beta-adrenergic-receptor] kinase (EC 2.7.1.126); [myosin heavy-chain] kinase (EC 2.7.1.129); [Tau protein] kinase (EC 2.7.1.135); macrolide 2'-kinase (EC 2.7.1.136); I-phosphatidylinositol 3-kinase (EC 2.7.1.137); [RNA-polymerase]-subunit kinase (EC 2.7.1.141); phosphatidylinositol-4,5-bisphosphate 3-kinase (EC 2.7.1.153); and phosphatidylinositol-4-phosphate 3-kinase (EC 2.7.1.154). Group I further comprises the lipid kinase family (321 sequences). These kinases include: I-phosphatidylinositol-4-phosphate 5-kinase (EC 2.7.1.68); I D-myo-inositol-triphosphate 3-kinase (EC 2.7.1.127); inositol-tetrakisphosphate 5-kinase (EC 2.7.1.140); I-phosphatidylinositol-5-phosphate 4-kinase (EC 2.7.1.149); I-phosphatidylinositol-3-phosphate 5-kinase (EC 2.7.1.150); inositol-polyphosphate multikinase (EC 2.7.1.151); and inositol-hexakiphosphate kinase (EC 2.7.4.21). Group I further comprises the ATP-grasp kinases (729 sequences), which include inositol-tetrakisphosphate I-kinase (EC 2.7.1.134); pyruvate, phosphate dikinase (EC 2.7.9.1); and pyruvate, water dikinase (EC 2.7.9.2).

Group II (17,071 sequences) kinases incorporate the Rossman-like kinases. Group II comprises: (i) the P-loop kinase family (7,732 sequences), which include gluconokinase (EC 2.7.1.12); phosphoribulokinase (EC 2.7.1.19); thymidine kinase (EC 2.7.1.21); ribosylnicotinamide kinase (EC 2.7.1.22); dephospho-CoA kinase (EC 2.7.1.24); adenylyl-sulfate kinase (EC 2.7.1.25); pantothenate kinase (EC 2.7.1.33); protein kinase (bacterial) (EC 2.7.1.37); uridine kinase (EC 2.7.1.48); shikimate kinase (EC 2.7.1.71); deoxycytidine kinase (EC 2.7.1.74); deoxyadenosine kinase (EC 2.7.1.76); polynucleotide 5'-hydroxyl-kinase (EC 2.7.1.78); 6-phosphofructo-2-kinase (EC 2.7.1.105); deoxyguanosine kinase (EC 2.7.1.113); tetraacyldisaccharide 4'-kinase (EC 2.7.1.130); deoxynucleoside kinase (EC 2.7.1.145); adenosylcobinamide kinase (EC 2.7.1.156); polyphosphate kinase (EC 2.7.4.1); phosphomevalonate kinase (EC 2.7.4.2); adenylate kinase (EC 2.7.4.3); nucleoside-phosphate kinase (EC 2.7.4.4); guanylate kinase (EC 2.7.4.8); thymidylate kinase (EC 2.7.4.9); nucleoside-triphosphate-adenylate kinase (EC 2.7.4.10); (deoxy)nucleoside-phosphate kinase (EC 2.7.4.13); cytidylate kinase (EC 2.7.4.14); and uridylate kinase (EC 2.7.4.-); (ii) the phosphoenolpyruvate carboxykinase family (815 sequences), which includes protein kinase (HPr kianse/phosphatase) (EC 2.7.1.37); phosphoenolpyruvate carboxykinase (GTP) (EC 4.1.1.32); and phosphoenolpyruvate carboxykinase (ATP) (EC 4.1.1.49); (iii) the phosphoglycerate kinase (1,351 sequences) family, which includes phosphoglycerate kinase (EC 2.7.2.3) and phosphoglycerate kinase (GTP) (EC 2.7.2.10); (iv) the aspartokinase family (2,171 sequences), which includes carbamate kinase (EC 2.7.2.2); aspartate kinase (EC 2.7.2.4); acetylglutamate kinase (EC 2.7.2.8 1); glutamate 5-kinase (EC 2.7.2.1) and uridylate kinase (EC 2.7.4.-); (v) the phosphofructokinase-like kinase family (1,998 sequences), which includes 6-phosphofrutokinase (EC 2.7.1.1 1); NAD(+) kinase (EC 2.7.1.23);

I-phosphofructokinase (EC 2.7.1.56); diphosphate-fructose-6-phosphate I-phosphotransferase (EC 2.7.1.90); sphinganine kinase (EC 2.7.1.91); diacylglycerol kinase (EC 2.7.1.107); and ceramide kinase (EC 2.7.1.138); (vi) the ribokinase-like family (2,722 sequences), which includes glucokinase (EC 2.7.1.2); ketohexokinase (EC 2.7.1.3); fructokinase (EC 2.7.1.4); 6-phosphofructokinase (EC 2.7.1.11); ribokinase (EC 2.7.1.15); adenosine kinase (EC 2.7.1.20); pyridoxal kinase (EC 2.7.1.35); 2-dehydro-3-deoxygluconokinase (EC 2.7.1.45); hydroxymethylpyrimidine kinase (EC 2.7.1.49); hydroxyethylthiazole kinase (EC 2.7.1.50); I-phosphofructokinase (EC 2.7.1.56); inosine kinase (EC 2.7.1.73); 5-dehydro-2-deoxygluconokinase (EC 2.7.1.92); tagatose-6-phosphate kinase (EC 2.7.1.144); ADP-dependent phosphofructokinase (EC 2.7.1.146); ADP-dependent glucokinase (EC 2.7.1.147); and phosphomethylpyrimidine kinase (EC 2.7.4.7); (vii) the thiamin pyrophosphokinase family (175 sequences), which includes thiamin pyrophosphokinase (EC 2.7.6.2); and (viii) the glycerate kinase family (107 sequences), which includes glycerate kinase ((EC 2.7.1.31).

Group III kinases (10,973 sequences) comprise (i) the ferredoxin-like fold kinases; (ii) the nucleoside-diphosphate kinase family (923 sequences), which includes nucleoside-diphosphate kianse (EC 2.7.4.6); (iii) the HPPK kinase family (609 sequences), which includes 2-amino-4-hydroxy-6-hydroxymethyldihydropteridine pyrophosphokinase (EC 2.7.6.3); (iv) the guanido kinase family (324 sequences), which includes guanidoacetate kinase (EC 2.7.3.1); creatine kinase (EC 2.7.3.2); arginine kinase (EC 2.7.3.3); and lombricine kinase (EC 2.7.3.5); (v) the histidine kinase family (9,117 sequences), which includes protein kinase (histidine kinase) (EC 2.7.1.37); [pyruvate dehydrogenase(lipoamide)] kinase (EC 2.7.1.99); and [3-methyl-2-oxybutanoate dehydrogenase(lipoamide)] kinase (EC 2.7.1.115).

Group IV kinases (2,768 sequences) incorporate H-like kinases, which include hexokinase (EC 2.7.1.1); glucokinase (EC 2.7.1.2); fructokinase (EC 2.7.1.4); rhamnulokinase (EC 2.7.1.5); mannokinase (EC 2.7.1.7); gluconokinase (EC 2.7.1.12); L-ribulokinase (EC 2.7.1.16); xylulokinase (EC 2.7.1.17); erythritol kinase (EC 2.7.1.27); glycerol kinase (EC 2.7.1.30); pantothenate kinase (EC 2.7.1.33); D-ribulokinase (EC 2.7.1.47); L-fucolokinase (EC 2.7.1.51); L-xylulokinase (EC 2.7.1.53); allose kinase (EC 2.7.1.55); 2-dehydro-3-deoxygalactonokinase (EC 2.7.1.58); N-acetylglucosamine kinase (EC 2.7.1.59); N-acylmannosamine kinase (EC 2.7.1.60); polyphosphate-glucose phosphotransferase (EC 2.7.1.63); beta-glucoside kinase (EC 2.7.1.85); acetate kinase (EC 2.7.2.1); butyrate kinase (EC 2.7.2.7); branched-chain-fatty-acid kinase (EC 2.7.2.14); and propionate kinase (EC 2.7.2.-).

Group V kinases (1,119 sequences) incorporate TIM β/α-barrel kinases, which include pyruvate kinase (EC 2.7.1.40).

Group VI kinases (885 sequences) incorporate GHMP kinases. These enzymes include galactokinase (EC 2.7.1.6); mevalonate kinase (EC 2.7.1.36); homoserine kinase (EC 2.7.1.39); L-arabinokinase (EC 2.7.1.46); fucokinase (EC 2.7.1.52); shikimate kinase (EC 2.7.1.71); 4-(cytidine 5'-diphospho)-2-C-methyl-D-erythriol kinase (EC 2.7.1.148); and phosphomevalonate kinase (EC 2.7.4.2)

Group VII kinases (1,843 sequences) incorporate AIR synthetase-like kinases, which include thiamine-phosphate kinase (EC 2.7.4.16) and selenide, water dikinase (EC 2.7.9.3).

Group VIII kinases (565 sequences) incorporate riboflavin kinases (565 sequences), which include riboflavin kinase (EC 2.7.1.26).

Group IX kinases (197 sequences) incorporate dihydroxyacetone kinases, which include glycerone kinase (EC 2.7.1.29).

Group X kinases (148 sequences) incorporate putative glycerate kinases, which include glycerate kinase (EC 2.7.1.31).

Group XI kinases (446 sequences) incorporate polyphosphate kinases, which include polyphosphate kinases (EC 2.7.4.1).

Group XII kinases (263 sequences) incorporate integral membrane kinases. Group XII comprises the dolichol kinase family, which include dolichol kinases (EC 2.7.1.108); and the undecaprenol kinase family, which include undecaprenol kinases (EC 2.7.1.66).

Kinases, which are among the best-studied enzymes at the structural, biochemical, and cellular levels, play indispensable roles in numerous cellular metabolic and signaling pathways. Even though all kinases use the same phosphate donor (in most cases, ATP) and appear to catalyze apparently the same phosphoryl transfer reaction, they display remarkable diversity in their structural folds and substrate recognition mechanisms. This is probably due largely to the extraordinarily diverse nature of the structures and properties of their substrates.

Signal Transduction Pathways

The AGC family of protein kinases, which comprise isoforms of protein kinase B (PKB, also known as Akt), p70 ribosomal S6 kinase (S6K), serum- and glucocorticoid-induced protein kinase (SGK), and atypical isoforms of protein kinase C (PKC), are activated within minutes of insulin- or growth factor induced stimulation of phosphatidylinositol 3-kinase ($PI_3$-kinase). Once activated, PKB/Akt phosphorylates and modulates the function of a number of important regulatory proteins, resulting in inhibition of apoptosis, formation of cell division and stimulation of glucose uptake and storage. The serine/threonine kinase Akt (protein kinase B) is a critical enzyme in signal transduction pathways involved in cell proliferation, apoptosis, angiogenesis, and diabetes. Three isoforms of Akt ($\alpha$, $\beta$, $\gamma$ or Akt 1, 2, 3) are known in mammals. These isoforms exhibit a high degree of homology but differ slightly in the localization of their regulatory phosphorylation sites. The Akt enzymes are composed of three functionally distinct regions: 1) an N-terminal pleckstrin homology (PH) domain; 2) a central catalytic domain; and 3) a C-terminal hydrophobic motif. The PH domain in the N-terminal region of Akt provides a lipid binding module to direct Akt to $PIP_2$ (phosphatidyl inositol bisphosphate or the products obtained by cleavage of $PIP_3$) and $PIP_3$ (phosphatidyl inositol (3,4,5)-triphosphate, the product of the class I phosphoinositide 3-kinase activity on phosphatidyl inositol (4,5)-bisphosphate), interacts with 3'-phosphoinositides and helps to recruit Akt to the plasma membrane.

In unstimulated cells, Akt is constitutively phosphorylated at $Ser^{124}$, in the region between the PH and catalytic domains, and on $Thr^{450}$, in the C-terminal region (in Akt$\alpha$). Activation of Akt involves growth factor binding to a receptor tyrosine kinase and activation of PI 3-K (PI 3-K phosphorylates membrane bound $PIP_2$ to generate $PIP_3$). The binding of $PIP_3$ to the PH domain anchors Akt to the plasma membrane and allows its phosphorylation and activation by PDK1 (pyruvate dehydrogenase kinase isozyme 1). Akt is fully activated following its phosphorylation at two regulatory residues, a threonine residue on the kinase domain and a serine residue on the hydrophobic motif. These motifs are structurally and functionally conserved within the AGC kinase family. Phosphorylation at $Thr^{308}$ and $Ser^{473}$ is required for the activation of Akt$\alpha$. Phosphorylation at $Thr^{309}$ and $Ser^{474}$ activates Akt$\beta$.

Phosphorylation at Thr$^{305}$ activates Aktγ. Akt activation requires phosphorylation of a threonine residue on the kinase domain, catalyzed by PDK1. This causes a charge-induced conformational change, and allows substrate binding and an increased rate of catalysis. Phosphorylation at the serine residue, primarily by mTOR/richtor complex (mTORC$_2$), augments Akt activity by approximately 10-fold. Studies indicate that DNA-PK and PKCbII phosphorylate the serine residue on the regulatory subunit. The hydrophobic motif of Akt, without threonine phosphorylation, is more susceptible to the action of phosphatases; however, the dually phosphorylated and fully active enzyme is stable, allowing its localization to the nucleus and other sites. The activity of Akt is negatively regulated by PTEN (phosphatase and tensin homolog gene whose product acts as a phosphatase to dephosphorylate phosphatidylinositol (3,4,5)-triphosphate) and SHIP (SH2-containing inositol phosphatase, INPP5D).

Akt facilitates growth factor-mediated cell survival and blocks apoptotic cell death by deactivating (via phosphorylation) pro-apoptotic factors such as Bad, caspase-9, and Forkhead transcription factors (AFX, Daf-16, FKHR). The phosphorylation of Bad at Ser$^{136}$ promotes its association with 14-3-3 proteins in the cytosol; this prevents Bad from localizing at the mitochondria to induce apoptosis. Akt promotes cell survival by inactivating caspase-9 via phosphorylation at Ser$^{196}$. Similarly, activated Akt phosphorylates Forkhead family members, resulting in their sequestration in the cytoplasm. In the absence of survival factors and Akt activity, Forkhead family members translocate to the nucleus, wherein they initiate a program of gene expression (for example, FasL) that promotes cell death. Akt also phosphorylates and activates IKKα (a subunit of IκB alpha kinase complex that has an important role in the activation of nuclear factor-κB (NF-κB), a key regulator of normal and tumor cell proliferation, apoptosis and response to chemotherapy) at Thr$^{23}$. The activated IKKα, in turn, phosphorylates IκB, targeting it for ubiquitination and proteasomal degradation. This leads to the activation and nuclear translocation of NF-κB, and the transcription of NF-kB-dependent pro-survival genes which include BCl-x$_L$ and caspase inhibitors.

Akt also phosphorylates and inactivates GSK-3 (glycogen synthase kinase-3), allowing the activation of glycogen synthase to proceed. GSK-3 phosphorylates cyclin D (a regulator of G1 to S phase transition), targeting cyclin D for proteolysis. Thus, the inactivation of GSK-3 may promote the up-regulation of cyclin D and enhance cell cycling.

Studies indicate Akt phosphorylates Chk1 (a DNA damage effector kinase) at Ser$^{280}$ thereby preventing human protein kinases ATM (ataxiaAtaxia telangiectasia mutated) and ATR (Ataxia telangiectasia and Rad3 related) from activating Chk1 via phosphorylation at Ser$^{345}$. This may be of therapeutic significance as Chk1 inhibition enhances sensitization of tumors to chemotherapeutic agents.

Akt phosphorylates Cdc25B on Ser$^{353}$, resulting in its cytoplasmic accumulation. Cdc25B undergoes activation during S-phase and has a role in activating the mitotic kinase Cdk1/cyclin B in the cytoplasm. This relocation of Cdc25B to the cytoplasm allows Akt to regulate Cdc25B function and participate in controlling the entry of cells into mitosis.

The regulation of Akt by a number of upstream oncogenes and tumor suppressor genes influences cancer progression. Breast cancer cell lines express Aktα in varying degrees. The Akt inhibitor, 1L-6-hydroxymethylchiro-inositol 2-(R)-2-O-methyl-3-O-octadecylcarbonate, reduces survival of both drug resistant and drug sensitive multiple myeloma cells. Akt also has a critical role in tumorigenesis. Akt is activated when tumor suppressors, such as cell cycle inhibitor p27 and PTEN, lose their functions. Akt impairs the nuclear import of p27 by phosphorylation of p27 at Thr$^{157}$. Cytoplasmic mislocalization of p27 has been strongly linked to loss of differentiation and poor outcome in breast cancer. Akt also is reported to associate physically with endogenous p21 (a cell cycle inhibitor). The phosphorylation of p21 at Thr$^{145}$ by Akt causes p21 localization to the cytoplasm and subsequent degradation.

Akt and p53 (also known as protein 53 or tumor protein 53, a transcription factor that regulates the cell cycle) have opposing roles in signaling pathways that determine cell survival. Under conditions where the apoptotic effect of p53 is dominant, destruction of Akt has a role in accelerating the apoptotic process. In apoptosis-prone cells, p53-dependent signaling enables downregulation of Akt, which predisposes cells to rapid apoptosis in response to stress signals. Under certain circumstances, Akt activation may overcome the death promoting effects of p53 and may rescue cells from apoptosis. Studies indicate that Akt can phosphorylate Mdm2 (a protein encoded by an oncogene that modulates p53 tumor suppressor activity) on Ser$^{166}$ and Ser$^{188}$ and promote Mdm2 translocation to the nucleus wherein Mdm2 destabilizes p53 and enhances its degradation via the proteasomal pathway.

Kinase Inhibition

The eukaryotic protein kinases constitute one of the largest superfamilies of homologous proteins that are related to each other by virtue of their catalytic domains. Most related protein kinases are specific for either serine/threonine phosphorylation or tyrosine phosphorylation. Stimulation of protein kinases is considered to be one of these enzymes most common activation mechanisms in signal transduction systems and therefore plays an integral role in the cellular response to extracellular stimuli. Many substrates are known to undergo phosphorylation by multiple protein kinases. A considerable amount of information on primary sequence of the catalytic domains of various protein kinases has been published. These sequences share a large number of residues involved in ATP binding, catalysis, and maintenance of structural integrity. Most protein kinases possess a well conserved 30-32 kDa catalytic domain. Studies have attempted to identify and utilize regulatory elements of protein kinases. These regulatory elements include antibodies, blocking peptides, and inhibitors.

Inhibitors

Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both.

Enzyme inhibitors often are evaluated by their specificity and potency. The term "specificity" as used herein refers to the selective attachment or influence of one substance on another. The term "potency" as used herein refers to efficacy, effectiveness, strength, or, typically, the dissociation constant, which indicates the concentration needed to inhibit an enzyme.

Inhibitors of protein kinases have been studied for use as tools in protein kinase activity regulation. Inhibitors have been studied for use with, for example, cyclin-dependent (Cdk) kinase, MAP kinase, serine/threonine kinase, Src Family protein tyrosine kinase, tyrosine kinase, calmodulin (CaM) kinase, casein kinase, checkpoint kinase (Chk1), GSK-3, JNK, MEK, myosin light chain kinase (MLCK), protein kinase A, Akt (protein kinase B), protein kinase C, protein kinase G, protein tyrosine kinase, Raf kinase, and Rho kinase.

Antibodies

Antibodies (or "immunoglobulins") are gamma globulin proteins produced by B lymphocytes of the immune system in response to an antigen used by the body to identify and neutralize foreign objects having that antigen. In their native form, they are typically made of basic structural units—each with two large heavy (H) chains and two small light (L) chains—to form, for example, monomers with one unit, dimers with two units or pentamers with five units. There are several different types of antibody heavy chains, and several different kinds of antibodies, which are grouped into different isotypes based on which heavy chain they possess. Five different antibody isotypes are known in mammals, which perform different roles, and help direct the appropriate immune response for each different type of foreign object they encounter. The specificity and binding affinity of an antibody are dictated by the three polyvariable loops of the VL chain and the three hypervariable loops of the VH chain located on each arm of that antibody. Variations in the lengths and sequences of these loops define the antibody-combining site (ACS). As used herein, the term "antibody" includes, by way of example, both naturally occurring and non-naturally occurring antibodies. Specifically, the term "antibody" includes polyclonal antibodies and monoclonal antibodies, and fragments thereof. Furthermore, the term "antibody" includes chimeric antibodies and wholly synthetic antibodies, and fragments thereof. The terms "epitope" and "antigenic determinant" are used interchangeably herein to refer to the site on a molecule that an ACS recognizes and to which that antibody binds/attaches itself. An epitope may be an antigenic determinant/antigen binding site on a kinase inhibiting peptide. The epitope may be primary, secondary, or tertiary-sequence related.

The specificity of the interactions between certain antibodies and protein kinases has been studied for use in protein kinase activity regulation. Antibodies have been isolated for use with, for example, MAP kinase pathways, protein kinase A, protein kinase B, protein kinase G, serine/threonine kinases, glycogen-synthase kinase-3 (GSK-3), stress-activated protein (SAP) kinase pathways, and tyrosine kinases. Additionally, antibodies have been isolated for use with protein kinase inhibitors and protein kinase substrates.

Blocking Peptides

A peptide is a chemical compound that is composed of a chain of two or more amino acids; the carboxyl group of one amino acid is linked to the amino group of an adjacent amino acid to form a peptide bond. The term "polypeptide" is used herein in its broadest sense to refer to a sequence of subunit amino acids, amino acid analogs or peptidomimetics, wherein the subunits are linked by peptide bonds. The peptides or polypeptides may by chemically synthesized or expressed recombinantly. Peptides have been used in the study of protein structure and function. Synthetic peptides may be used as probes to see where protein-peptide interactions occur. Inhibitory peptides may be used in clinical research to examine the effects of peptides on the inhibition of protein kinases, cancer proteins and other disorders.

The use of several blocking peptides has been studied. For example, extracellular signal-regulated kinase (ERK), a MAPK protein kinase (meaning any of a group of protein serine/threonine kinases that respond to extracellular stimuli (antigens) and regulate various cellular activities), is essential for cellular proliferation and differentiation. The activation of MAPKs requires a cascade mechanism whereby MAPK is phosphorylated by an upstream MAPKK (MEK) which is then, in turn phosphorylated by a third kinase MAPKKK (MEKK). This inhibitory peptide functions as a MEK decoy by binding to ERK. It contains the amino-terminal 13 amino acids (GMPKKKPTPIQLN) [SEQ ID NO: 149] of MEK1 and binds to ERK. This blocks ERK activation by MEK as ERK is unable to interact with MEK. The ERK inhibitory peptide also contains a protein transduction (PTD) sequence (DRQIKIWFQNRRMKWKK) [SEQ ID NO: 150] derived from Antennapedia which renders the peptide cell permeable.

Other blocking peptides include autocamtide-2 related inhibitory peptide (AIP). This synthetic peptide is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an $IC_{50}$ of 100 nM ($IC_{50}$ is a concentration of the inhibitor required to obtain 50% inhibition). The AIP inhibition is non-competitive with respect to syntide-2 (CaMKII Peptide Substrate) and ATP but competitive with respect to autocamtide-2. The inhibition is unaffected by the presence or absence of Ca2+/calmodulin. CaMKII activity is completely inhibited by 1 μM AIP; PKA, PKC and CaMKIV are not affected. The amino acid sequence of AIP is: KKALRRQEAVDAL (Lys-Lys-Ala-Leu-Arg-Arg-Gln-Glu-Ala-Val-Asp-Ala-Leu) [SEQ ID NO: 151].

Other blocking peptides include cyclin-dependent kinase 5 (Cdk5) inhibitory peptide (CIP). Cdk5 phosphorylates tau at Alzheimer's Disease (AD)-specific phospho-epitopes when it associates with the p25 regulatory component. p25 is a truncated activator of the Cdk-p25 heterodimer (a microtubule associated protein), which is produced from the physiological Cdk5 activator p35 upon exposure to amyloid-beta (Aβ, a protein implicated in AD) peptides. Upon neuronal infections with CIP, CIPs selectively inhibit p25/Cdk5 activity and suppress the aberrant tau phosphorylation in cortical neurons. The reasons for the specificity demonstrated by CIP are not fully understood.

Additional blocking peptides have been studied for ERK2, ERK3, p38/HOG1, protein kinase C, casein kinase II, $Ca^{2+}$/calmodulin kinase IV, casein kinase II, Cdk4, Cdk5, DNA-PK, PAK3, PI-3 kinase, PI-5 kinase, PSTAIRE, ribosomal S6 kinase, GSK-4, GCK, SAPK, SEK1, and FAK.

Protein Transduction Domains

New drug delivery technologies occupy an important niche in treatments as they enable drugs to be more effective. Drug delivery still is considered a poor relation to drug discovery, with greater than 95% of all new potential therapeutics having poor pharmacokinetics. The greatest impediment for cytosolic release of therapeutic molecules is the membrane barrier of target cells. Protein transduction domains (PTDs), also referred to as Trojan peptides, membrane translocating sequences or cell permeable proteins, are a class of peptides that are generally capable of penetrating the plasma membrane of mammalian cells. PTDs are generally 10-16 amino acids in length and may be grouped according to their composition, for example peptides rich in arginine and/or lysine. PTDs also may be used to assist novel HSP27 kinase inhibitors to penetrate cell membranes (see, e.g., PCT/US2007/16246, filed Jul. 16, 2007, entitled "Polypeptic Inhibitors of HSP27 and Uses Thereof," which is incorporated by reference herein in its entirety). PTDs are capable of transporting compounds of many types and molecular weights across mammalian cells. These compounds include effector molecules, such as proteins, DNA, conjugated peptides, oligonucleotides, and small particles such as liposomes. When PTDs are chemically linked or fused to other proteins these fusion proteins are still able to penetrate the plasma membrane and enter cells. Although the exact mechanism of this transduction is unknown, internalization of these proteins is not believed to be receptor-mediated or transporter-mediated. The use of PTDs capable of transporting effector molecules into cells has become increasingly attractive in the design of drugs as they promote the cellular uptake of cargo molecules. These cell penetrating peptides, generally categorized as amphipathic or cationic depending on their sequence, provide a non-invasive delivery technology for macromolecules.

Viral PTD Containing Proteins

The first proteins to be described as having transduction properties were viral in origin. These proteins still are the most commonly accepted models for PTD action. The HIV-1 Transactivator of transcription (TAT) and HSV-1 VP 22 protein are the best characterized viral PTD containing proteins.

TAT (HIV-1 trans-activator gene product) is an 86-amino acid polypeptide that act as a powerful transcription factor of the integrated HIV-1 genome. TAT stimulates viral replication in latently infected cells. The translocation properties of the TAT protein enable it to activate quiescent infected cells and may be involved in priming of uninfected cells for subsequent infection by regulating many cellular genes, including cytokines. The minimal PTD of TAT is the 9 amino acid protein sequence RKKRRQRRR (TAT$_{49-57}$) [SEQ ID NO: 152]. Studies utilizing a longer fragment of TAT demonstrated successful transduction of fusion proteins up to 120 kDa. The addition of multiple TAT-PTDs and synthetic TAT derivatives have been demonstrated to mediate membrane translocation. TAT PTD containing fusion proteins have been used as therapeutic moieties in experiments involving cancer, for transporting a death-protein into cells, and in disease models of neurodegenerative disorders.

VP22 is the HSV-1 tegument protein, a structural part of the HSV virion. VP22 is capable of receptor independent translocation and accumulates in the nucleus. This property of VP22 classifies the protein as a PTD containing peptide. Fusion proteins comprising full length VP22 have been efficiently translocated across the plasma membrane.

Homeoproteins with Intercellular Translocation Properties

Homeoproteins are highly conserved, transactivating transcription factors involved in morphological processes. They bind to DNA through a specific sequence of 60 amino acids. The DNA-binding homeodomain is the most highly conserved sequence of the homeoprotein. Several homeoproteins exhibit PTD like activity; they are capable of efficient translocation across cell membranes in an energy-independent and endocytosis-independent manner without cell type specificity.

The Antennapedia protein (Antp) is a trans-activating factor capable of translocation across cell membranes; the minimal sequence capable of translocation is a 16 amino acid peptide corresponding to the third helix of the protein's homeodomain. The internalization of this helix occurs at 4° C. suggesting that this process is not endocytosis dependent. Peptides of up to 100 amino acids produced as fusion proteins with AntpHD penetrate cell membranes.

Other homeodomains capable of translocation include Fushi tarazu (Ftz) and Engrailed (En) homeodomain. Since the third helix of all homeodomains is highly conserved, it is likely that other homeodomains may possess similar characteristics.

Synthetic PTDs

Several PTD peptides have been synthesized. Many of these synthetic peptides are based on existing and well documented peptides, while others are selected for their basic residues and/or positive charge, which are thought to be crucial for PTD function. These synthetic peptides include: PTD-4 (YARAAARQARA) [SEQ ID NO: 153]; PTD-5 (RRQRRTSKLMKR) [SEQ ID NO: 154]; MST-1 (AAVLL-PVLLAAR) [SEQ ID NO: 155]; L-R9 (RRRRRRRRR) [SEQ ID NO: 156]; and Peptide 2 (SGWFRRWKK) [SEQ ID NO: 157].

Human PTDs

Human PTDs may circumvent potential immunogenicity issues when used as a therapeutic upon introduction into a human patient. Peptides with PTD sequences include: Hoxa-5, Hox-A4, Hox-B5, Hox-B6, Hox-B7, HOX-D3, GAX, MOX-2, and FtzPTD, all of which share the sequence found in AntpPTD (RQIKIWFQNRRMKWKK) [SEQ ID NO: 158]. Other PTDs include Islet-1, interleukin-1β, tumor necrosis factor, and the hydrophobic sequence from Kaposi-FGF (K-FGF or FGF-4) signal peptide which is capable of energy-, receptor-, and endocytosis-independent translocation. Unconfirmed PTDs include members of the Fibroblast Growth Factor (FGF) family.

At present, it is possible to produce a given protein molecule by recombinant DNA technology for in vivo therapeutic applications. Although small molecules or peptides capable of crossing cellular membranes have been successfully designed to deliver small or moderately large proteins, it remains a challenge to deliver the recombinant proteins to desired targets in vivo. Despite developments in the area of protein transduction peptides, the classical delivery methods of protein-coding genes via adeno-associated virus, adenovirus, lentivirus, herpes virus vectors, and plasmid expression vectors remain the preferred choice for expression of proteins.

Viral vector-mediated gene expression is considered the most efficient and reliable approach for expressing functional proteins de novo in mitotically active or postmitotically blocked cell types due to their natural abilities to deliver the specific genes to permissive cells. Nonetheless, viral vectors invariably are required in large doses to achieve therapeutic expression levels of intended proteins and may integrate with the host chromatin material. Because these properties may have undesirable consequences for host genetic systems, safety remains a serious concern for their ultimate clinical application.

While an alternative approach, i.e., to produce recombinant proteins exogenously and then deliver them systemically or by localized injections into the target organs, appears to have a better safety profile, the delivery and bioavailability of recombinant proteins into cells or tissues needs refinement.

Several studies have shown the potential of PTD in drug discovery and transduction of proteins up to 120 kDa into different cells. In vivo injection of fusion proteins systemically has demonstrated the effectiveness of the PTD in protein delivery. Despite successful applications, questions about potency of PTD mediated protein transduction still remain unsolved. Further, some studies in PTD-mediated fusion protein transduction in vitro/in vivo and attempting to induce an immune response have failed. Further, intracellular expression of PTD fusion proteins or other non-secretory proteins may not achieve the same biodistribution as that of recombinant protein. Further, entry of PTD through the blood-brain barrier remains elusive.

The delivery of a diverse set of cargo ranging from small molecules to particulate cargo has been attempted using different types of cell penetrating peptides in vitro and in vivo. However, the internalization mechanism of these peptides is an unresolved issue to date, with dramatic changes in view regarding the involvement of an energy dependent process involving endocytosis as a pathway of internalization. An improvement in the effectiveness of PTDs would significantly increase bioavailability and lower the required doses of existing and novel therapeutics.

The present invention provides transduction domain peptides that are useful for the inhibition of kinases. The present invention further provides a class of peptides that include certain transduction domains that are useful as inhibitors of kinase activity. The present invention further provides transduction domain peptides that are useful as therapeutic agents for a variety of hyper plastic and neoplastic disorders. The present invention further provides transduction domain peptides that are useful as substances to cause cell death.

SUMMARY OF THE INVENTION

The present invention relates to kinase inhibiting compositions and uses thereof and provides isolated kinase inhibiting peptides and uses thereof for inhibiting hyperplasia, for inhibiting the growth of neoplasms, and for inducing programmed cell death in a cell population.

In one aspect, the present invention provides a method for inhibiting a kinase activity of a kinase enzyme, the method comprising the steps: (a) providing a kinase inhibiting composition, wherein the kinase inhibiting composition comprises an inhibitory amount of a kinase inhibiting peptide; (b) contacting kinase enzyme with the kinase inhibiting composition of step (a) such that the kinase inhibiting peptide associates with the kinase enzyme; and (c) inhibiting the kinase activity of the kinase enzyme. According to one embodiment of the method, the kinase inhibiting peptide is a KIP peptide. According to another embodiment, the kinase inhibiting peptide is a cyclin-dependent-kinase inhibitor. According to another embodiment, the kinase inhibiting peptide is a peptide having an amino acid sequence according to Formula IV [Q1-Z1-Z2-Z3-Z4-Z5-Z6-Q2] [SEQ ID NO: 193], wherein Q1 and Q2 are independently absent or present, and wherein if Q1 and Q2 are present, Q1 and Q2 comprise a polypeptide having an amino acid sequence according to Formula IV(a) [X1-X2-X3-X4-X5-X6-X7-X8-X9-X10-X11] [SEQ ID NO: 194], wherein X1 is any amino acid except K, or is absent; X2 is present or is absent; and when X2 is present, X2 is any amino acid; X3 is any amino acid; X4 is any amino acid; X5 is any basic amino acid; X6 is any amino acid; X7 is any amino acid; X8 is any amino acid; X9 is any amino acid; X10 is any amino acid; X11 is any amino acid, or is absent; and wherein Z1 and Z2 are present; wherein Z3 is present or absent, wherein Z4 is absent or present, but if Z4 is present, Z3 is present, wherein Z5 is absent or present, but if Z5 is present, Z3 and Z4 are present; wherein Z6 is absent or present, but if Z6 is present, Z3, Z4 and Z5 are present; and each of Z1, Z2, Z3, Z4, Z5, and Z6, is a peptide selected from the group consisting of: (a) X1-X2-B1-B2-X3-B3-X4 [Formula IV(b)] [SEQ ID NO: 195], wherein each of X1, X3 and X4 is a hydrophobic amino acid; X2 is any amino acid; and wherein each of B1, B2 and B3 is a basic amino acid; (b) X1-X2-B1-B2-X3-B3 [Formula IV(c)] [SEQ ID NO: 196], wherein each of X1 and X3 is a hydrophobic amino acid, X2 is any amino acid; and wherein each of B1, B2, and B3 is a basic amino acid; (c) X1-X2-B1-B2-X3 [Formula IV(d)] [SEQ ID NO: 197], wherein each of X1 and X3 is a hydrophobic amino acid; X2 is any amino acid; and wherein each of B1 and B2 is a basic amino acid; (d) X1-B1-B2-X2-B3-X3 [Formula IV(e)] [SEQ ID NO: 198], wherein X1 is any amino acid; each of X2 and X3 is a hydrophobic amino acid, and each of B1, B2, and B3 is a basic amino acid; (e) X1-B1-B2-X2-B3 [Formula IV(f)] [SEQ ID NO: 199], wherein X1 is a hydrophobic amino acid, H or N; X2 is a hydrophobic amino acid; and each of B1, B2, and B3 is a basic amino acid; (f) X1-B1-B2-X2 [Formula IV(g)] [SEQ ID NO: 200], wherein X1 is any amino acid; X2 is a hydrophobic amino acid; and each of B1 and B2 is a basic amino acid; (g) X1-X2-B1-B2 [Formula IV(h)] [SEQ ID NO: 201], wherein X1 is a hydrophobic amino acid, X2 is any amino acid; and each of B1 and B2 is a basic amino acid; (h) X1-X2-B1-X3-X4 [Formula IV(i)] [SEQ ID NO: 202], wherein each of X1, X3, and X4 is a hydrophobic amino acid; X2 is any amino acid; and B1 is a basic amino acid; (i) X1B1-X2-X3 [Formula IV(j)] [SEQ ID NO: 203], wherein X1 is any amino acid; X2 is any amino acid; X3 is a hydrophobic amino acid; and B1 is any basic amino acid; (j) X1-X2-B1-X3 [Formula IV(k)] [SEQ ID NO: 204], wherein each of X1 and X3 is a hydrophobic amino acid; X2 is any amino acid; and B1 is a basic amino acid; (k) B1-B2-X1-X2-B3-X3 [Formula IV(l)] [SEQ ID NO: 205], wherein each of X1, X2, and X3 is a hydrophobic amino acid; and each of B1, B2, and B3 is a basic amino acid; (l) B1-B2-X1-X2-B3 [Formula IV(m)] [SEQ ID NO: 206], wherein each of X1 and X2 is a hydrophobic amino acid; and each of B1, B2, and B3 is a basic amino acid; (m) B1-B2-X1-X2 [Formula IV(n)] [SEQ ID NO: 207], wherein each of X1 and X2 is a hydrophobic amino acid; and each of B1 and B2 is a basic amino acid; (n) B1-X1-X2-B2-B3X3 [Formula IV(o)] [SEQ ID NO: 208], wherein each of X1, X2, and X3 is a hydrophobic amino acid; and each of B1, B2, and B3 is a basic amino acid; (o) B1-X1-X2-B2-B3 [Formula IV(p)] [SEQ ID NO: 209], wherein each of X1 and X2 is a hydrophobic amino acid, and each of B1, B2, and B3 is a basic amino acid; and (p) B1-X1-X2-B2 [Formula IV(q)] [SEQ ID NO: 210], wherein each of X1 and X2 is a hydrophobic amino acid; and each of B1 and B2 is a basic amino acid; with the proviso that if Q2 is present, the two amino acids immediately preceding Q2 as part of Z2, Z3, Z4, Z5, or Z6 cannot be KA. According to one such embodiment, Q1, Z3, Z4, Z5, and Z6 are absent [SEQ ID NO: 211]. According to another such embodiment, X2 in formula IV(a) is a hydrophobic amino acid, H or N [SEQ ID NO: 212]. According to another such embodiment, X2 in formula IV(a) is A [SEQ ID NO: 213]. According to another such embodiment, X3 in formula IV(a) is a hydrophobic amino acid [SEQ ID NO: 214]. According to another such embodiment, X3 is selected from the group consisting of L, I, V, and M [SEQ ID NO: 215]. According to another such embodiment, X4 in formula IV(a) is selected from the group consisting of Q, A and N [SEQ ID NO: 216]. According to another such embodiment, X6 in formula IV(a) is selected from the group consisting of Q and N [SEQ ID NO: 217]. According to another such embodiment, X7 in formula IV(a) is a hydrophobic amino acid [SEQ ID NO: 218]. According to another such embodiment, X7 in formula IV(a) is selected from the group consisting of L, I, V and M [SEQ ID NO: 219]. According to another such embodiment, X8 in formula IV(a) is selected from the group consisting of G, A, C, S, T, and Y [SEQ ID NO: 220]. According to another such embodiment, X9 in formula IV(a) is a hydrophobic amino acid [SEQ ID NO: 221]. According to another such embodiment, X9 in formula IV(a) is selected from the group consisting of L, I, V and M [SEQ ID NO: 222]. According to another such embodiment, X9 in formula IV(a) is V [SEQ ID NO: 223]. According to another embodiment of the method, the kinase inhibiting peptide is a peptide having an amino acid sequence selected from the group consisting of HRRIKAWLKKILALARQLGVAA [SEQ ID NO: 192]; WLRRIKAWLRRIKALARQLGVAA [SEQ ID NO: 113]; and WLRRIKAWLRRALARQLGVA [SEQ ID NO: 177]. According to another embodiment of the method, the amino acid sequence of the kinase inhibiting peptide is HRRIKAWLKKILALARQLGVAA [SEQ ID NO: 192]. According to another embodiment of the method, the amino acid sequence of the kinase inhibiting peptide is WLR-RIKAWLRRIKALARQLGVAA [SEQ ID NO: 113]. According to another embodiment of the method, the amino acid sequence of the kinase inhibiting peptide is WLR-RIKAWLRRALARQLGVA [SEQ ID NO: 177]. According to another embodiment of the method, the kinase inhibiting peptide is a peptide having an amino acid sequence according to Formula V [(XXBBXBXX)$_n$][SEQ ID NO: 224] wherein X is any amino acid, B is a basic amino acid, and n is an integer between 2 and 5. According to one such embodiment, B is K, R or H [SEQ ID NO: 225]. According to another embodiment of the method, the kinase inhibiting peptide is a peptide having an amino acid sequence according to Formula VI [Z1-X1-X2-X3-X4 X5-X6-X7-X8-X9-X10-Z2] [SEQ ID NO: 226], wherein each of Z1 and Z2 is absent or is a transduction domain; X1 is absent or present, and if present is selected from the group consisting of A, KA, KKA, KKKA [SEQ ID NO: 186], and RA; X2 is selected from the group consisting of an aliphatic amino acid, G, L, A, V, I, M, Y, W, and F; X3 is selected from the group consisting of an aliphatic amino acid, V, L, I, A, G, Q, N, S, T, and C; X4 is selected from the group consisting of Q, N, H, R and K; X5 is selected from the group consisting of Q and N; X6 is selected from the group consisting of an aliphatic amino acid, C, A, G, L, V, I, M, Y, W, and F; X7 is selected from the group consisting of an aliphatic amino acid, S, A, C, T, and G; X8 is selected from the group consisting of V, L, I, and M; X9 is absent or is any amino acid; and X10 is absent or is any amino acid. According to one such embodiment, X2 is selected from the group consisting of G, L, A, V, I, M, Y, W, and F [SEQ ID NO: 227]. According to another such embodiment, X3 is selected from the group consisting of V, L, I, A, G, Q, N, S, T, and C [SEQ ID NO: 228]. According to another such embodiment, X6 is selected from the group consisting of C, A, G, L, V, I, M, Y, W, and F [SEQ ID NO: 229]. According to another such embodiment, the kinase inhibiting peptide is a peptide having an amino acid sequence selected from the group consisting of KAFAKLAARLYRKALARQLGVAA [SEQ ID NO: 173]; FAKLAARLYRKALARQLGVAA [SEQ ID NO: 163]; and WLRRIKAWLRRIKALNRQLGVAA [SEQ ID NO: 142]. According to another such embodiment, the amino acid sequence of the kinase inhibiting peptide is KAFAKLAAR-LYRKALARQLGVAA [SEQ ID NO: 173]. According to another such embodiment, the amino acid sequence of the kinase inhibiting peptide is FAKLAARLYRKALAR-QLGVAA [SEQ ID NO: 163]. According to another such embodiment, the amino acid sequence of the kinase inhibiting peptide is WLRRIKAWLRRIKALNRQLGVAA [SEQ ID NO: 142]. According to another embodiment of the method, the kinase enzyme is a kinase enzyme selected from the group consisting of: Ab 1, Akt/PKB, AMPK, Arg, Ask, Aurora-A, Axl, Blk, Bmx, Brk, BTK, CaMKI, CaMKI6, CaMKIIP, CaMKIIy, CaMKI1r3, Casein Kinase, Cdk, CDK9/cyclin, CKly1, CKly2, CKly3, Ck16, CK2a, CK2, CHK, CDK1/cyclinB, CHK1, CHK2 mutants, CK16, CK2, c-K1t, CLK2, CLK3, Cott, Csk, DAPK1, DCAMKL2, DDR, DYRK2, EGFR, Ephs, EphA2, FAK, Fer, Fes/Fps, FGFR, FGFR1, Fgr, Fit, Flt3, Flt4, Fms/CSF-1R, Fyn, GRK5, GRK6, GRK7, GSK, CSK3, Hck, HERIErbB, HIPK1, HIPK2, HIPK3, IGF-1, ICF IR, IKK, Insulin R, IRAK, IRAK1, IRAK4, JAK, JAK1, JAK2, JAK3, JNK/SAPK, KDR, Lck, LIMK, LIMK1, LOK, Lyn, MAPK, MAPK1, MAPKAP Kinase, MEK, MEK1, MELK, Met, Mer, MINK, MKK, MLCK, MLK1, MRCKa, MSK1, MST, MST3, NEK, NEK3, NEK9, PDGFR, PDGFRa, PDGFRP, PDK, PhKy2, PI 3-Kinase, PIM, Pim-1, Pim-2, Pim-3, PKC, PKC31, PKC6, PKD2, PKR, PKA, PKBP, PKCPI, PKC6, PKG1, PKG1a, PKG1r3, PKR, PLK, PRAK, PTK5, Pyk, Raf, Rct, RIPK2, ROK/ROCK, ROCK-I, Ron, Ros, Rse, Rsk4, Rsk/MAPKAP Kinase, S6 K1nase, Rsk2, SAPK2a, SGK, c-Src, Src(1-530), Src, Syk, TAK1, TAO1, TAO2, TBK, Tie2/TEK, TLK2, Trk, TSSK2, TrkA, Txk, ULK3, Ulk2, VRK2, WEE, Yes, ZAP-70 and ZIPK. According to one such embodiment, the kinase enzyme is selected from the group consisting of a ROCK kinase, a Src kinase, a PKC kinase and a Trk kinase. According to some such embodiments, the kinase enzyme is a ROCK kinase. According to some such embodiments, the kinase enzyme is an Src kinase. According to some such embodiments, the kinase enzyme is a PKC kinase. According to some such embodiments, the kinase enzyme is a Trk kinase.

In another aspect, the present invention provides a method for inhibiting hyperplasia in a cell population, the method comprising the steps: (a) providing a therapeutically effective amount of a kinase inhibiting composition to a subject in need thereof, wherein the kinase inhibiting composition comprises an inhibitory amount of a kinase inhibiting peptide; (b) contacting at least one hyperplastic cell in the cell population with the kinase inhibitory composition such that the kinase inhibiting peptide associates with the at least one hyperplastic cell; and (c) inhibiting the hyperplasia of the at least one hyperplastic cell. According to one embodiment, the kinase inhibiting peptide is a KIP peptide. According to another embodiment, the kinase inhibiting peptide is a cyclin-dependent-kinase inhibitor. According to another embodiment, the kinase inhibiting peptide is a peptide having an amino acid sequence according to Formula IV [Q1-Z1-Z2-Z3-Z4-Z5-Z6-Q2][SEQ ID NO: 193], wherein Q1 and Q2 are independently absent or present, and wherein if Q1 and Q2 are present, Q1 and Q2 comprise a polypeptide having an amino acid sequence according to Formula IV(a) [X1-X2-X3-X4-X5-X6-X7-X8-X9-X10-X11] [SEQ ID NO: 194], wherein X1 is any amino acid except K, or is absent; X2 is present or is absent; and when X2 is present, X2 is any amino acid; X3 is any amino acid; X4 is any amino acid; X5 is any basic amino acid; X6 is any amino acid; X7 is any amino acid; X8 is any amino acid; X9 is any amino acid; X10 is any amino acid; X11 is any amino acid, or is absent; and wherein Z1 and Z2 are present; wherein Z3 is present or absent, wherein Z4 is absent or present, but if Z4 is present, Z3 is present, wherein Z5 is absent or present, but if Z5 is present, Z3 and Z4 are present; wherein Z6 is absent or present, but if Z6 is present, Z3, Z4 and Z5 are present; and each of Z1, Z2, Z3, Z4, Z5, and Z6, is a peptide selected from the group consisting of: (a) X1-X2-B1-B2-X3-B3-X4 [Formula IV(b)] [SEQ ID NO: 195], wherein each of X1, X3 and X4 is a hydrophobic amino acid; X2 is any amino acid; and wherein each of B1, B2 and B3 is a basic amino acid; (b) X1-X2-B1-B2-X3-B3 [Formula IV(c)] [SEQ ID NO: 196], wherein each of X1 and X3 is a hydrophobic amino acid, X2 is any amino acid; and wherein each of B1, B2, and B3 is a basic amino acid; (c) X1-X2-B1-B2-X3 [Formula IV(d)] [SEQ ID NO: 197], wherein each of X1 and X3 is a hydrophobic amino acid; X2 is any amino acid; and wherein each of B1 and B2 is a basic amino acid; (d) X1-B1-B2-X2-B3-X3 [Formula IV(e)] [SEQ ID NO: 198], wherein X1 is any amino acid; each of X2 and X3 is a hydrophobic amino acid, and each of B1, B2, and B3 is a basic amino acid; (e) X1-B1-B2-X2-B3 [Formula IV(f)] [SEQ ID NO: 199], wherein X1 is a hydrophobic amino acid, H or N; X2 is a hydrophobic amino acid; and each of B1, B2, and B3 is a basic amino acid; (f) X1-B1-B2-X2 [Formula IV(g)] [SEQ ID NO: 200], wherein X1 is any amino acid; X2 is a hydrophobic amino acid; and each of B1 and B2 is a basic amino acid; (g) X1-X2-B1-B2 [Formula IV(h)] [SEQ ID NO: 201], wherein X1 is a hydrophobic amino acid, X2 is any amino acid; and each of B1 and B2 is a basic amino acid; (h) X1-X2-B1-X3-X4 [Formula IV(i)] [SEQ ID NO: 202], wherein each of X1, X3, and X4 is a hydrophobic amino acid; X2 is any amino acid; and B1 is a basic amino acid; (i) X1B1-X2-X3 [Formula IV(j)] [SEQ ID NO: 203], wherein X1 is any amino acid; X2 is any amino acid; X3 is a hydrophobic amino acid; and B1 is a basic amino acid; (j) X1-X2-B1-X3 [Formula IV(k)] [SEQ ID NO: 204], wherein each of X1 and X3 is a hydrophobic amino acid; X2 is any amino acid; and B1 is a basic amino acid; (k) B1-B2-X1-X2-B3-X3 [Formula IV(l)] [SEQ ID NO: 205], wherein each of X1, X2, and X3 is a hydrophobic amino acid; and each of B1, B2, and B3 is a basic amino acid; (l) B1-B2-X1-X2-B3 [Formula IV(m)] [SEQ ID NO: 206], wherein each of X1 and X2 is a hydrophobic amino acid; and each of B1, B2, and B3 is a basic amino acid; (m) B1-B2-X1-X2 [Formula IV(n)] [SEQ ID NO: 207], wherein each of X1 and X2 is a hydrophobic amino acid; and each of B1 and B2 is a basic amino acid; (n) B1-X1-X2-B2-B3X3 [Formula IV(o)] [SEQ ID NO: 208], wherein each of X1, X2, and X3 is a hydrophobic amino acid; and each of B1, B2, and B3 is a basic amino acid; (o) B1-X1-X2-B2-B3 [Formula IV(p)] [SEQ ID NO: 209], wherein each of X1 and X2 is a hydrophobic amino acid, and each of B1, B2, and B3 is a basic amino acid; and (p) B1-X1-X2-B2 [Formula IV(q)] [SEQ ID NO: 210], wherein each of X1 and X2 is a hydrophobic amino acid; and each of B1 and B2 is a basic amino acid; with the proviso that if Q2 is present, the two amino acids immediately preceding Q2 as part of Z2, Z3, Z4, Z5, or Z6 cannot be KA. According to one such embodiment, Q1, Z3, Z4, Z5, and Z6 are absent [SEQ ID NO: 211]. According to another such embodiment, X2 in formula IV(a) is a hydrophobic amino acid, H or N [SEQ ID NO: 212]. According to another such embodiment, X2 in formula IV(a) is A [SEQ ID NO: 213]. According to another such embodiment, X3 in formula IV(a) is a hydrophobic amino acid [SEQ ID NO: 214]. According to another such embodiment, X3 in formula IV(a) is selected from the group consisting of L, I, V, and M [SEQ ID NO: 215]. According to another such embodiment, X4 in formula IV(a) is selected from the group consisting of Q, A and N [SEQ ID NO: 216]. According to another such embodiment, X6 in formula IV(a) is selected from the group consisting of Q and N [SEQ ID NO: 217]. According to another such embodiment, X7 in formula IV(a) is a hydrophobic amino acid [SEQ ID NO: 218]. According to another such embodiment, X7 in formula IV(a) is selected from the group consisting of L, I, V and M [SEQ ID NO: 219]. According to another such embodiment, X8 in formula IV(a) is selected from the group consisting of G, A, C, S, T, and Y [SEQ ID NO: 220]. According to another such embodiment, X9 in formula IV(a) is a hydrophobic amino acid [SEQ ID NO: 221]. According to another such embodiment, X9 in formula IV(a) is selected from the group consisting of L, I, V and M [SEQ ID NO: 222]. According to another such embodiment, in formula IV(a) X9 is V [SEQ ID NO: 223]. According to another embodiment of the method, the kinase inhibiting peptide is a peptide having an amino acid sequence selected from the group consisting of HRRIKAWLKKILA-LARQLGVAA [SEQ ID NO: 192]; WLRRIKAWLR-RIKALARQLGVAA [SEQ ID NO: 113]; and WLR-RIKAWLRRALARQLGVA [SEQ ID NO: 177]. According to another embodiment of the method, the amino acid sequence of the kinase inhibiting peptide is HRRIKAWLK-KILALARQLGVAA [SEQ ID NO: 192]. According to another embodiment of the method, the amino acid sequence of the kinase inhibiting peptide is WLRRIKAWLR-RIKALARQLGVAA [SEQ ID NO: 113]. According to another embodiment of the method, the amino acid sequence of the kinase inhibiting peptide is WLRRIKAWLRRALAR-QLGVA [SEQ ID NO: 177]. According to another embodiment of the method, the kinase inhibiting peptide is a peptide having an amino acid sequence according to Formula V [(XXBBXBXX)$_n$] [SEQ ID NO: 224] wherein X is any amino acid, B is a basic amino acid, and n is an integer between 2 and 5. According to one such embodiment, B is K, R or H [SEQ ID NO: 225]. According to another embodiment of the method, the kinase inhibiting peptide is a peptide having an amino acid sequence according to Formula VI [Z1-X1-X2-X3-X4 X5-X6-X7-X8-X9-X10-Z2] [SEQ ID NO: 226], wherein each of Z1 and Z2 is absent or is a transduction domain; X1 is absent or present, and if present is selected from the group consisting of A, KA, KKA, KKKA [SEQ ID NO: 186], and RA; X2 is selected from the group consisting of an aliphatic amino acid, G, L, A, V, I, M, Y, W, and F; X3 is selected from the group consisting of an aliphatic amino acid, V, L, I, A, G, Q, N, S, T, and C; X4 is selected from the group consisting of Q, N, H, R and K; X5 is selected from the group consisting of Q and N; X6 is selected from the group consisting of an aliphatic amino acid, C, A, G, L, V, I, M, Y, W, and F; X7 is selected from the group consisting of an aliphatic amino acid, S, A, C, T, and G; X8 is selected from the group consisting of V, L, I, and M; X9 is absent or is any amino acid; and X10 is absent or is any amino acid. According to one such embodiment, X2 is selected from the group consisting of G, L, A, V, I, M, Y, W, and F [SEQ ID NO: 227]. According to another such embodiment, X3 is selected from the group consisting of V, L, I, A, G, Q, N, S, T, and C [SEQ ID NO: 228]. According to another such embodiment, X6 is selected from the group consisting of C, A, G, L, V, I, M, Y, W, and F [SEQ ID NO: 229]. According to another such embodiment, the kinase inhibiting peptide is a peptide having an amino acid sequence selected from the group consisting of KAFAKLAARLYRKALARQLGVAA [SEQ ID NO: 173]; FAKLAARLYRKALARQLGVAA [SEQ ID NO: 163]; and WLRRIKAWLRRIKALNRQLGVAA [SEQ ID NO: 142]. According to another such embodiment, the amino acid sequence of the kinase inhibiting peptide is KAFAKLAAR-LYRKALARQLGVAA [SEQ ID NO: 173]. According to another such embodiment, the amino acid sequence of the kinase inhibiting peptide is FAKLAARLYRKALAR-QLGVAA [SEQ ID NO: 163]. According to another such embodiment, the amino acid sequence of the kinase inhibiting peptide is WLRRIKAWLRRIKALNRQLGVAA [SEQ ID NO: 142].

In another aspect, the present invention provides a method for inhibiting growth of a neoplasm, the method comprising the steps: (a) providing a therapeutically effective amount of a kinase inhibiting composition to a subject in need thereof, wherein the kinase inhibiting composition comprises an inhibitory amount of a kinase inhibiting peptide; and (b) contacting the neoplasm with the kinase inhibiting composition such that the kinase inhibiting peptide associates with the neoplasm; and (c) inhibiting the growth of the neoplasm. According to one embodiment, the kinase inhibiting peptide is a KIP peptide. According to another embodiment, the kinase inhibiting peptide is a cyclin-dependent-kinase inhibitor. According to another embodiment, the kinase inhibiting peptide is a peptide having an amino acid sequence according to Formula IV [Q1-Z1-Z2-Z3-Z4-Z5-Z6-Q2] [SEQ ID NO: 193], wherein Q1 and Q2 are independently absent or present, and wherein if Q1 and Q2 are present, Q1 and Q2 comprise a polypeptide having an amino acid sequence according to Formula IV(a) [X1-X2-X3-X4-X5-X6-X7-X8-X9-X10-

X11] [SEQ ID NO: 194], wherein X1 is any amino acid except K, or is absent; X2 is present or is absent; and when X2 is present, X2 is any amino acid; X3 is any amino acid; X4 is any amino acid; X5 is any basic amino acid; X6 is any amino acid; X7 is any amino acid; X8 is any amino acid; X9 is any amino acid; X10 is any amino acid; X11 is any amino acid, or is absent; and wherein Z1 and Z2 are present; wherein Z3 is present or absent, wherein Z4 is absent or present, but if Z4 is present, Z3 is present, wherein Z5 is absent or present, but if Z5 is present, Z3 and Z4 are present; wherein Z6 is absent or present, but if Z6 is present, Z3, Z4 and Z5 are present; and each of Z1, Z2, Z3, Z4, Z5, and Z6, is a peptide selected from the group consisting of: (a) X1-X2-B1-B2-X3-B3-X4 [Formula IV(b)] [SEQ ID NO: 195], wherein each of X1, X3 and X4 is a hydrophobic amino acid; X2 is any amino acid; and wherein each of B1, B2 and B3 is a basic amino acid; (b) X1-X2-B1-B2-X3-B3 [Formula IV(c)] [SEQ ID NO: 196], wherein each of X1 and X3 is a hydrophobic amino acid, X2 is any amino acid; and wherein each of B1, B2, and B3 is a basic amino acid; (c) X1-X2-B1-B2-X3 [Formula IV(d)] [SEQ ID NO: 197], wherein each of X1 and X3 is a hydrophobic amino acid; X2 is any amino acid; and wherein each of B1 and B2 is a basic amino acid; (d) X1-B1-B2-X2-B3-X3 [Formula IV(e)] [SEQ ID NO: 198], wherein X1 is any amino acid; each of X2 and X3 is a hydrophobic amino acid, and each of B1, B2, and B3 is a basic amino acid; (e) X1-B1-B2-X2-B3 [Formula IV(f)] [SEQ ID NO: 199], wherein X1 is a hydrophobic amino acid, H or N; X2 is a hydrophobic amino acid; and each of B1, B2, and B3 is a basic amino acid; (f) X1-B1-B2-X2 [Formula IV(g)] [SEQ ID NO: 200], wherein X1 is any amino acid; X2 is a hydrophobic amino acid; and each of B1 and B2 is a basic amino acid; (g) X1-X2-B1-B2 [Formula IV(h)] [SEQ ID NO: 201], wherein X1 is a hydrophobic amino acid, X2 is any amino acid; and each of B1 and B2 is a basic amino acid; (h) X1-X2-B1-X3-X4 [Formula IV(i)] [SEQ ID NO: 202], wherein each of X1, X3, and X4 is a hydrophobic amino acid; X2 is any amino acid; and B1 is a basic amino acid; (i) X1B1-X2-X3 [Formula IV(j)] [SEQ ID NO: 203], wherein X1 is any amino acid; X2 is any amino acid; X3 is a hydrophobic amino acid; and B1 is a basic amino acid; (j) X1-X2-B1-X3 [Formula IV(k)] [SEQ ID NO: 204], wherein each of X1 and X3 is a hydrophobic amino acid; X2 is any amino acid; and B1 is a basic amino acid; (k) B1-B2-X1-X2-B3-X3 [Formula IV(l)] [SEQ ID NO: 205], wherein each of X1, X2, and X3 is a hydrophobic amino acid; and each of B1, B2, and B3 is a basic amino acid; (l) B1-B2-X1-X2-B3 [Formula IV(m)] [SEQ ID NO: 206], wherein each of X1 and X2 is a hydrophobic amino acid; and each of B1, B2, and B3 is a basic amino acid; (m) B1-B2-X1-X2 [Formula IV(n)] [SEQ ID NO: 207], wherein each of X1 and X2 is a hydrophobic amino acid; and each of B1 and B2 is a basic amino acid; (n) B1-X1-X2-B2-B3X3 [Formula IV(o)] [SEQ ID NO: 208], wherein each of X1, X2, and X3 is a hydrophobic amino acid; and each of B1, B2, and B3 is a basic amino acid; (o) B1-X1-X2-B2-B3 [Formula IV(p)] [SEQ ID NO: 209], wherein each of X1 and X2 is a hydrophobic amino acid, and each of B1, B2, and B3 is a basic amino acid; and (p) B1-X1-X2-B2 [Formula IV(q)] [SEQ ID NO: 210], wherein each of X1 and X2 is a hydrophobic amino acid; and each of B1 and B2 is a basic amino acid; with the proviso that if Q2 is present, the two amino acids immediately preceding Q2 as part of Z2, Z3, Z4, Z5, or Z6 cannot be KA. According to such embodiment, Q1, Z3, Z4, Z5, and Z6 are absent [SEQ ID NO: 211]. According to another such embodiment, X2 in formula IV(a) is a hydrophobic amino acid, H or N [SEQ ID NO: 212]. According to another such embodiment, X2 in formula IV(a) is A [SEQ ID NO: 213]. According to another such embodiment, X3 in formula IV(a) is a hydrophobic amino acid [SEQ ID NO: 214]. According to another such embodiment, X3 in formula IV(a) is selected from the group consisting of L, I, V, and M [SEQ ID NO: 215]. According to another such embodiment, X4 in formula IV(a) is selected from the group consisting of Q, A and N [SEQ ID NO: 216]. According to another such embodiment, X6 in formula IV(a) is selected from the group consisting of Q and N [SEQ ID NO: 217]. According to another such embodiment, X7 in formula IV(a) is a hydrophobic amino acid [SEQ ID NO: 218]. According to another such embodiment, X7 in formula IV(a) is selected from the group consisting of L, I, V and M [SEQ ID NO: 219]. According to another such embodiment, X8 in formula IV(a) is selected from the group consisting of G, A, C, S, T, and Y [SEQ ID NO: 220]. According to another such embodiment, X9 in formula IV(a) is a hydrophobic amino acid [SEQ ID NO: 221]. According to another such embodiment, X9 in formula IV(a) is selected from the group consisting of L, I, V and M [SEQ ID NO: 222]. According to another such embodiment, X9 in formula IV(a) is V [SEQ ID NO: 223]. According to another embodiment of the method, the kinase inhibiting peptide is a peptide having an amino acid sequence selected from the group consisting of HRRIKAWLKKILALARQLGVAA [SEQ ID NO: 192]; WLRRIKAWLRRIKALARQLGVAA [SEQ ID NO: 113]; and WLRRIKAWLRRALARQLGVA [SEQ ID NO: 177]. According to another embodiment of the method, the amino acid sequence of the kinase inhibiting peptide is HRRIKAWLKKILALARQLGVAA [SEQ ID NO: 192]. According to another embodiment of the method, the amino acid sequence of the kinase inhibiting peptide is WLRRIKAWLRRIKALARQLGVAA [SEQ ID NO: 113]. According to another embodiment of the method, the amino acid sequence of the kinase inhibiting peptide is WLRRIKAWLRRALARQLGVA [SEQ ID NO: 177]. According to another embodiment of the method, the kinase inhibiting peptide is a peptide having an amino acid sequence according to Formula V [(XXBBXBXX)$_{n}$] [SEQ ID NO: 224] wherein X is any amino acid, B is a basic amino acid, and n is an integer between 2 and 5. According to one such embodiment, B is K, R or H [SEQ ID NO: 225]. According to another embodiment of the method, the kinase inhibiting peptide is a peptide having an amino acid sequence according to Formula VI [Z1-X1-X2-X3-X4 X5-X6-X7-X8-X9-X10-Z2] [SEQ ID NO: 226], wherein each of Z1 and Z2 is absent or is a transduction domain; X1 is absent or present, and if present is selected from the group consisting of A, KA, KKA, KKKA [SEQ ID NO: 186], and RA; X2 is selected from the group consisting of an aliphatic amino acid, G, L, A, V, I, M, Y, W, and F; X3 is selected from the group consisting of an aliphatic amino acid, V, L, I, A, G, Q, N, S, T, and C; X4 is selected from the group consisting of Q, N, H, R and K; X5 is selected from the group consisting of Q and N; X6 is selected from the group consisting of an aliphatic amino acid, C, A, G, L, V, I, M, Y, W, and F; X7 is selected from the group consisting of an aliphatic amino acid, S, A, C, T, and G; X8 is selected from the group consisting of V, L, I, and M; X9 is absent or is any amino acid; and X10 is absent or is any amino acid. According to one such embodiment, X2 is selected from the group consisting of G, L, A, V, I, M, Y, W, and F [SEQ ID NO: 227]. According to another such embodiment, X3 is selected from the group consisting of V, L, I, A, G, Q, N, S, T, and C [SEQ ID NO: 228]. According to another such embodiment, X6 is selected from the group consisting of C, A, G, L, V, I, M, Y, W, and F [SEQ ID NO: 229]. According to another embodiment of the method, the kinase inhibiting peptide is a peptide having an amino acid sequence selected from the group consisting of KAFAKLAARLYRKALARQLGVAA [SEQ ID NO: 173]; FAKLAARLYRKALARQLGVAA [SEQ ID NO: 163]; and WLRRIKAWLRRIKALNRQLGVAA [SEQ ID NO: 142]. According to another embodiment of the method, the amino acid sequence of the kinase inhibiting peptide is KAFAKLAARLYRKALARQLGVAA [SEQ ID NO: 173]. According to another embodiment of the method, the amino acid sequence of the kinase inhibiting peptide is FAKLAAR-LYRKALARQLGVAA [SEQ ID NO: 163]. According to another embodiment of the method, the amino acid sequence of the kinase inhibiting peptide is WLRRIKAWLRRIKAL-NRQLGVAA [SEQ ID NO: 142]. According to another embodiment of the method, the neoplasm is a neoplasm selected from the group consisting of a papilloma, an adenoma, a hydatidiform mole, a fibroma, a chondroma, an osteoma, a leiomyoma, a rhabdomyoma, a lipoma, a hemangioma, a lymphangioma, a polycythemia vera, an infectious mononucleosis, a "benign" glioma, a meningioma, a ganglioneuroma, a neurilemmoma, a neurofibroma, a pigmented nevus (mole), a pheochromocytoma, a carcinoid tumors, a teratoma, a carcinoma, an adenocarcinoma, a basal cell carcinoma, a choriocarcinoma, a fibrosarcoma, a chondrosarcoma, an osteosarcoma, a leiomyosarcoma, a rhabdomyosarcoma, a liposarcoma, a hemangiosarcoma, a lymphangiosarcoma, a myelocytic leukemia, an erythrocytic leukemia, a lymphocytic leukemia, a multiple myeloma, a monocytic leukemia, an Ewing's sarcoma, a non-Hodgkin's malignant lymphoma, a medulloblastoma, an oligodendroglioma, a neurilemma) sarcoma malignant melanoma, thymoma, a glioblastoma multiforme, an astrocytoma, an ependymoma, an meningeal sarcoma, a neuroblastoma (schwannoma), a neurofibrosarcoma, a malignant pheochromocytoma, a retinoblastoma, a carcinoid tumor, a nephroblastoma (Wilms' tumor), a teratocarcinoma and an embryonal carcinoma with choriocarcinoma.

In another aspect, the present invention provides a method for inducing programmed cell death in a cell population, the method comprising the steps: (a) providing a kinase inhibiting composition, wherein the kinase inhibiting composition comprises an inhibitory amount of a kinase inhibiting peptide; (b) contacting at least one cell in the cell population with the kinase inhibiting composition such that the kinase inhibiting peptide associates with the at least one cell; and (c) inducing programmed cell death of the at least one cell. According to one embodiment of the method, the kinase inhibiting peptide is a KIP peptide. According to another embodiment, the kinase inhibiting peptide is a cyclin-dependent-kinase inhibitor. According to another embodiment, the kinase inhibiting peptide is a peptide having an amino acid sequence according to Formula IV [Q1-Z1-Z2-Z3-Z4-Z5-Z6-Q2] [SEQ ID NO: 193], wherein Q1 and Q2 are independently absent or present, and wherein if Q1 and Q2 are present, Q1 and Q2 comprise a polypeptide having an amino acid sequence according to Formula IV(a) [X1-X2-X3-X4-X5-X6-X7-X8-X9-X10-X11] [SEQ ID NO: 194], wherein X1 is any amino acid except K, or is absent; X2 is present or is absent; and when X2 is present, X2 is any amino acid; X3 is any amino acid; X4 is any amino acid; X5 is any basic amino acid; X6 is any amino acid; X7 is any amino acid; X8 is any amino acid; X9 is any amino acid; X10 is any amino acid; X11 is any amino acid, or is absent; and wherein Z1 and Z2 are present; wherein Z3 is present or absent, wherein Z4 is absent or present, but if Z4 is present, Z3 is present, wherein Z5 is absent or present, but if Z5 is present, Z3 and Z4 are present; wherein Z6 is absent or present, but if Z6 is present, Z3, Z4 and Z5 are present; and each of Z1, Z2, Z3, Z4, Z5, and Z6, is a peptide selected from the group consisting of: (a) X1-X2-B1-B2-X3-B3-X4 [Formula IV(b)] [SEQ ID NO: 195], wherein each of X1, X3 and X4 is a hydrophobic amino acid; X2 is any amino acid; and wherein each of B1, B2 and B3 is a basic amino acid; (b) X1-X2-B1-B2-X3-B3 [Formula IV(c)] [SEQ ID NO: 196], wherein each of X1 and X3 is a hydrophobic amino acid, X2 is any amino acid; and wherein each of B1, B2, and B3 is a basic amino acid; (c) X1-X2-B1-B2-X3 [Formula IV(d)] [SEQ ID NO: 197], wherein each of X1 and X3 is a hydrophobic amino acid; X2 is any amino acid; and wherein each of B1 and B2 is a basic amino acid; (d) X1-B1-B2-X2-B3-X3 [Formula IV(e)] [SEQ ID NO: 198], wherein X1 is any amino acid; each of X2 and X3 is a hydrophobic amino acid, and each of B1, B2, and B3 is a basic amino acid; (e) X1-B1-B2-X2-B3 [Formula IV(f)] [SEQ ID NO: 199], wherein X1 is a hydrophobic amino acid, H or N; X2 is a hydrophobic amino acid; and each of B1, B2, and B3 is a basic amino acid; (f) X1-B1-B2-X2 [Formula IV(g)] [SEQ ID NO: 200], wherein X1 is any amino acid; X2 is a hydrophobic amino acid; and each of B1 and B2 is a basic amino acid; (g) X1-X2-B1-B2 [Formula IV(h)] [SEQ ID NO: 201], wherein X1 is a hydrophobic amino acid, X2 is any amino acid; and each of B1 and B2 is a basic amino acid; (h) X1-X2-B1-X3-X4 [Formula IV(i)] [SEQ ID NO: 202], wherein each of X1, X3, and X4 is a hydrophobic amino acid; X2 is any amino acid; and B1 is a basic amino acid; (i) X1B1-X2-X3 [Formula IV(j)] [SEQ ID NO: 203], wherein X1 is any amino acid; X2 is any amino acid; X3 is a hydrophobic amino acid; and B1 is a basic amino acid; (j) X1-X2-B1-X3 [Formula IV(k)] [SEQ ID NO: 204], wherein each of X1 and X3 is a hydrophobic amino acid; X2 is any amino acid; and B1 is a basic amino acid; (k) B1-B2-X1-X2-B3-X3 [Formula IV(l)] [SEQ ID NO: 205], wherein each of X1, X2, and X3 is a hydrophobic amino acid; and each of B1, B2, and B3 is a basic amino acid; (l) B1-B2-X1-X2-B3 [Formula IV(m)] [SEQ ID NO: 206], wherein each of X1 and X2 is a hydrophobic amino acid; and each of B1, B2, and B3 is a basic amino acid; (m) B1-B2-X1-X2 [Formula IV(n)] [SEQ ID NO: 207], wherein each of X1 and X2 is a hydrophobic amino acid; and each of B1 and B2 is a basic amino acid; (n) B1-X1-X2-B2-B3X3 [Formula IV(o)] [SEQ ID NO: 208], wherein each of X1, X2, and X3 is a hydrophobic amino acid; and each of B1, B2, and B3 is a basic amino acid; (o) B1-X1-X2-B2-B3 [Formula IV(p)] [SEQ ID NO: 209], wherein each of X1 and X2 is a hydrophobic amino acid, and each of B1, B2, and B3 is a basic amino acid; and (p) B1-X1-X2-B2 [Formula IV(q)] [SEQ ID NO: 210], wherein each of X1 and X2 is a hydrophobic amino acid; and each of B1 and B2 is any basic amino acid; with the proviso that if Q2 is present, the two amino acids immediately preceding Q2 as part of Z2, Z3, Z4, Z5, or Z6 cannot be KA. According to one such embodiment, Q1, Z3, Z4, Z5, and Z6 are absent [SEQ ID NO: 211]. According to another such embodiment, X2 in formula IV(a) is a hydrophobic amino acid, H or N [SEQ ID NO: 212]. According to another such embodiment, X2 in formula IV(a) is A [SEQ ID NO: 213]. According to another such embodiment, X3 in formula IV(a) is a hydrophobic amino acid [SEQ ID NO: 214]. According to another such embodiment, X3 in formula IV(a) is selected from the group consisting of L, I, V, and M [SEQ ID NO: 215]. According to another such embodiment, X4 in formula IV(a) is selected from the group consisting of Q, A and N [SEQ ID NO: 216]. According to another such embodiment, X6 in formula IV(a) is selected from the group consisting of Q and N [SEQ ID NO: 217]. According to another such embodiment, X7 in formula IV(a) is a hydrophobic amino acid [SEQ ID NO: 218]. According to another such embodiment, X7 in formula IV(a) is selected from the group consisting of L, I, V and M [SEQ ID NO: 219].

According to another such embodiment, X8 in formula IV(a) is selected from the group consisting of G, A, C, S, T, and Y [SEQ ID NO: 220]. According to another such embodiment, X9 in formula IV(a) is a hydrophobic amino acid [SEQ ID NO: 221]. According to another such embodiment, X9 in formula IV(a) is selected from the group consisting of L, I, V and M [SEQ ID NO: 222]. According to another such embodiment, X9 in formula IV(a) is V [SEQ ID NO: 223]. According to another embodiment of the method, the kinase inhibiting peptide is a peptide having an amino acid sequence selected from the group consisting of HRRIKAWLKKILALARQLGVAA [SEQ ID NO: 192]; WLRRIKAWLRRIKALARQLGVAA [SEQ ID NO: 113]; and WLRRIKAWLRRALARQLGVA [SEQ ID NO: 177]. According to another embodiment of the method, the amino acid sequence of the kinase inhibiting peptide is HRRIKAWLKKILALARQLGVAA [SEQ ID NO: 192]. According to another embodiment of the method, the amino acid sequence of the kinase inhibiting peptide is WLRRIKAWLRRIKALARQLGVAA [SEQ ID NO: 113]. According to another embodiment of the method, the amino acid sequence of the kinase inhibiting peptide is WLRRIKAWLRRALARQLGVA [SEQ ID NO: 177]. According to another embodiment of the method, the kinase inhibiting peptide is a peptide having an amino acid sequence according to Formula V [(XXBBXBXX)$_{n}$] [SEQ ID NO: 224] wherein X is any amino acid, B is a basic amino acid, and n is an integer between 2 and 5. According to one such embodiment, B is K, R or H [SEQ ID NO: 225]. According to another embodiment of the method, the kinase inhibiting peptide is a peptide having an amino acid sequence according to Formula VI [Z1-X1-X2-X3-X4 X5-X6-X7-X8-X9-X10-Z2] [SEQ ID NO: 226], wherein each of Z1 and Z2 is absent or is a transduction domain; X1 is absent or present, and if present is selected from the group consisting of A, KA, KKA, KKKA [SEQ ID NO: 186], and RA; X2 is selected from the group consisting of an aliphatic amino acid, G, L, A, V, I, M, Y, W, and F; X3 is selected from the group consisting of an aliphatic amino acid, V, L, I, A, G, Q, N, S, T, and C; X4 is selected from the group consisting of Q, N, H, R and K; X5 is selected from the group consisting of Q and N; X6 is selected from the group consisting of an aliphatic amino acid, C, A, G, L, V, I, M, Y, W, and F; X7 is selected from the group consisting of an aliphatic amino acid, S, A, C, T, and G; X8 is selected from the group consisting of V, L, I, and M; X9 is absent or is any amino acid; and X10 is absent or is any amino acid. According to one such embodiment, X2 is selected from the group consisting of G, L, A, V, I, M, Y, W, and F [SEQ ID NO: 227]. According to another such embodiment, X3 is selected from the group consisting of V, L, I, A, G, Q, N, S, T, and C [SEQ ID NO: 228]. According to another such embodiment, X6 is selected from the group consisting of C, A, G, L, V, I, M, Y, W, and F [SEQ ID NO: 229]. According to another such embodiment, the kinase inhibiting peptide is a peptide having an amino acid sequence selected from the group consisting of KAFAKLAARLYRKALARQLGVAA [SEQ ID NO: 173]; FAKLAARLYRKALARQLGVAA [SEQ ID NO: 163]; and WLRRIKAWLRRIKALNRQLGVAA [SEQ ID NO: 142]. According to another such embodiment, the amino acid sequence of the kinase inhibiting peptide is KAFAKLAARLYRKALARQLGVAA [SEQ ID NO: 173]. According to another such embodiment, the amino acid sequence of the kinase inhibiting peptide is FAKLAARLYRKALARQLGVAA [SEQ ID NO: 163]. According to another such embodiment, the amino acid sequence of the kinase inhibiting peptide is WLRRIKAWLRRIKALNRQLGVAA [SEQ ID NO: 142]. According to another embodiment of the method, the cell is a prokaryotic cell. According to another embodiment of the method, the cell is a eukaryotic cell. According to another embodiment of the method, the programmed cell death occurs by apoptosis.

DETAILED DESCRIPTION OF THE INVENTION

Figure 1:
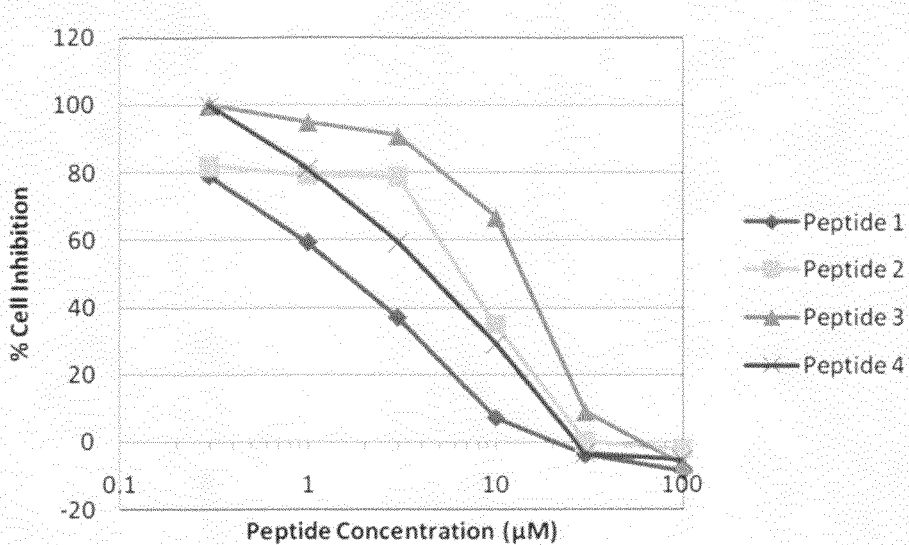
FIG. 1 shows MCF-7 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 15 μM.
Figure 2:
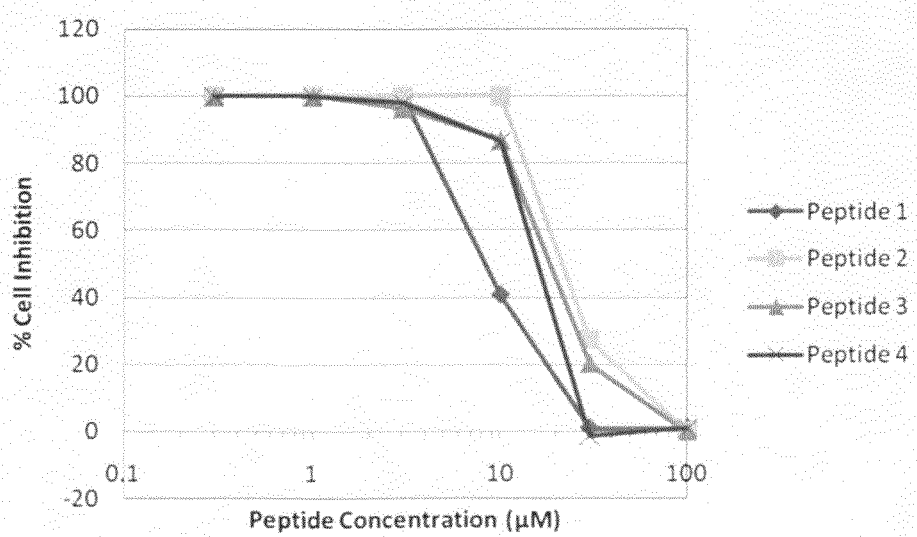
FIG. 2 shows MDA 231 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 20 μM.
Figure 3:
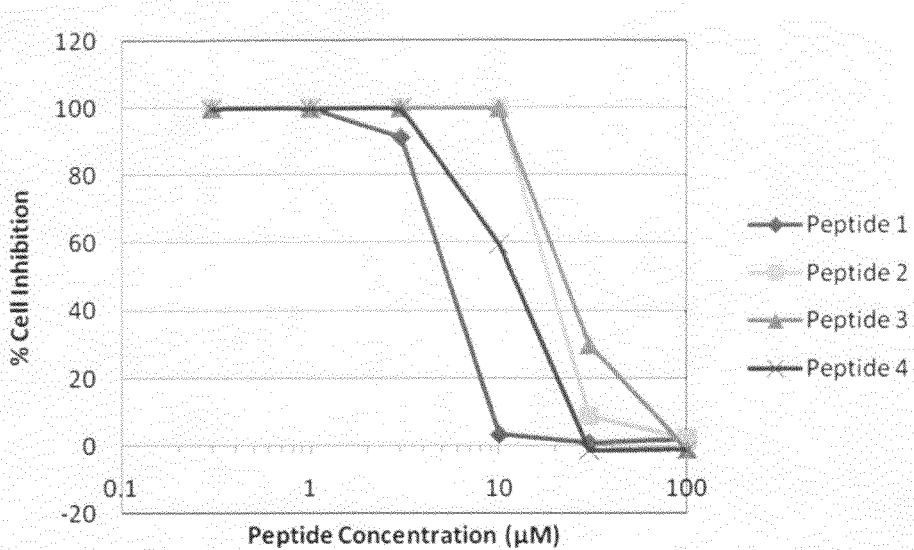
FIG. 3 shows SF539 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 27 μM.
Figure 4:
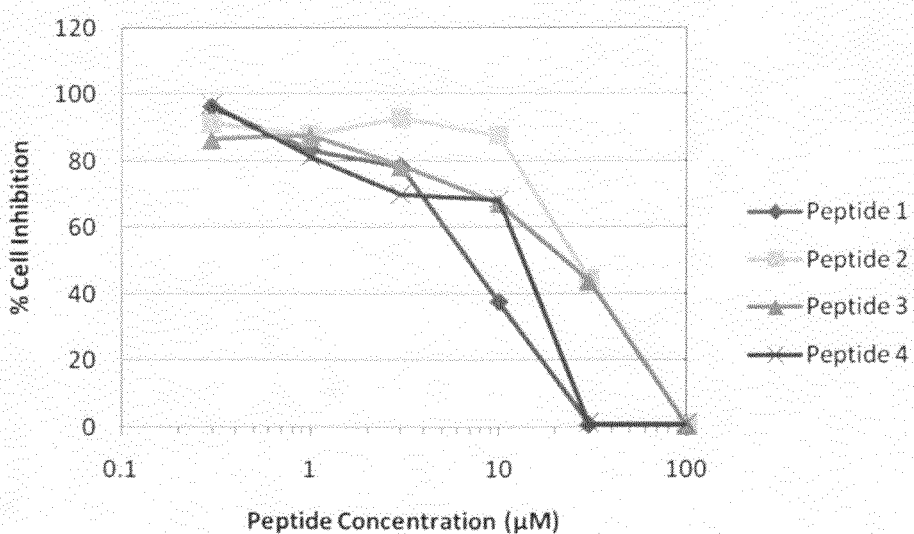
FIG. 4 shows HT29 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 27 μM.
Figure 5:
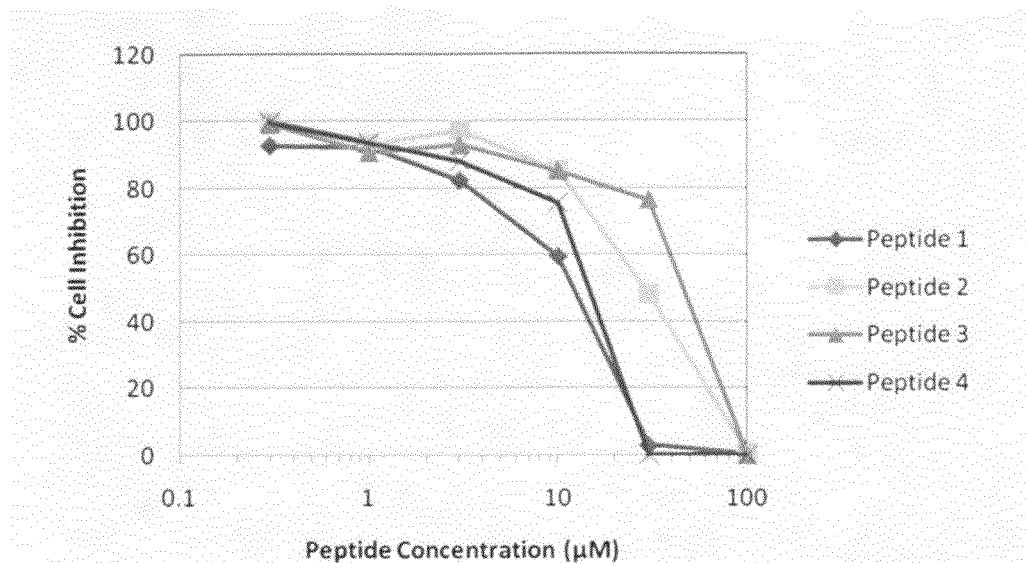
FIG. 5 shows Paca 2 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 43 μM.
Figure 6:
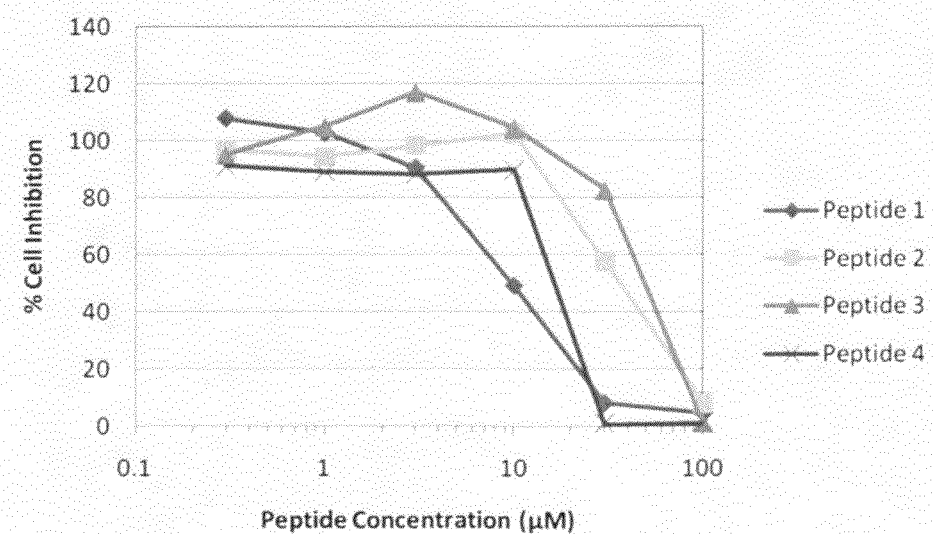
FIG. 6 shows PC3 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 36 μM.
Figure 7:
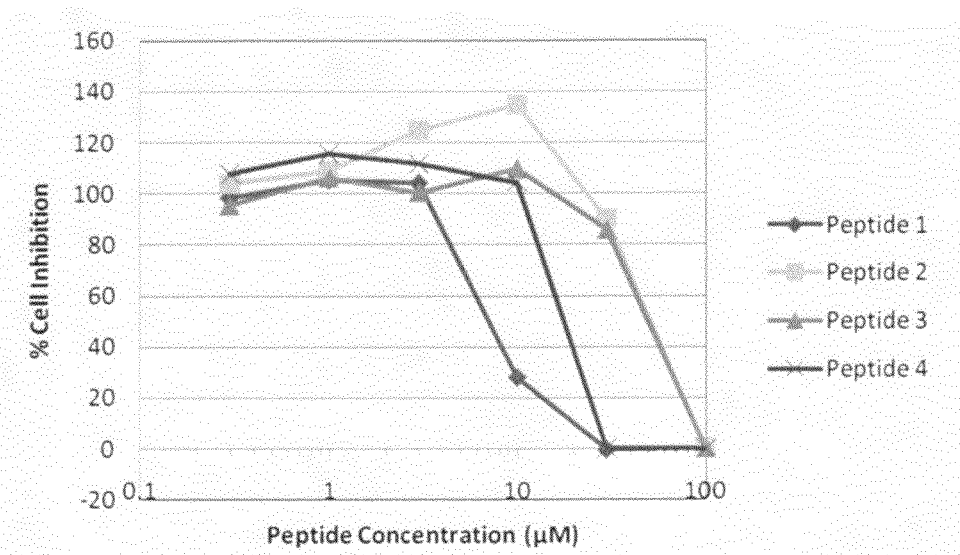
FIG. 7 shows A549 cells treated with different doses of four KIP peptides. Peptide 1 is HRRIKAWLKKIKALARQLGVAA [SEQ ID NO: 166], peptide 2 is WLRRIKAHRRIKALARQLGVAA [SEQ ID NO: 167], peptide 3 is WLRRIKAWLRR [SEQ ID NO: 168], and peptide 4 is WLRRIKAWLRRALNRQLGVAA [SEQ ID NO: 169]. For all peptides, the IC50 concentration was below 35 μM.

The present invention provides therapeutic kinase inhibiting compositions and methods of use thereof.

The terms "administering" or "administration" as used herein are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

Additional administration may be performed, for example, intravenously, pericardially, orally, via implant, transmucosally, transdermally, intramuscularly, subcutaneously, intraperitoneally, intrathecally, intralymphatically, intralesionally, or epidurally. Administering can be performed, for example, once, a plurality of times, and/or over one or more extended periods. The term "topical administration" and "topically applying" as used herein are used interchangeably to refer to delivering a peptide, the nucleic acid, or a vector comprising the peptide or the nucleic acid onto one or more surfaces of a tissue or cell, including epithelial surfaces.'

Although topical administration, in contrast to transdermal administration, generally provides a local rather than a systemic effect. The terms "topical administration" and "transdermal administration" as used herein, unless otherwise stated or implied, are used interchangeably.

The term "associate" or "associates" as used herein refers to joining, connecting, or combining to, either directly, indirectly, actively, inactively, inertly, non-inertly, completely or incompletely.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; I=Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The term "contacting" as used herein refers to bring or put in contact, to be in or come into contact. The term "contact" as used herein refers to a state or condition of touching or of immediate or local proximity. Contacting a composition to a target destination, such as, but not limited to, an organ, tissue, cell, or tumor, may occur by any means of administration known to the skilled artisan.

Methods exist for the transduction and the transfection of nucleic acids into cells. The terms "transduction," or "transduce" as used herein are used interchangeably to refer to the process of crossing biological membranes. The crossing of biological membranes may be from one cell to another, from the extracellular environment to the intracellular environment, or across a cell membrane or nuclear membrane. Materials that may undergo transduction include, but are not limited to, proteins, fusion proteins, peptides, polypeptides, amino acids, viral DNA, and bacterial DNA.

The term "regulatory sequence" (also referred to as a "regulatory region" or "regulatory element") refers to a promoter, enhancer or other segment of DNA where regulatory proteins, such as transcription factors, bind preferentially to control gene expression and thus protein expression.

The term "controllable regulatory element" as used herein refers to nucleic acid sequences capable of effecting the expression of the nucleic acids, or the peptide or protein product thereof. Controllable regulatory elements may be operably linked to the nucleic acids, peptides, or proteins of the present invention. The controllable regulatory elements, such as, but not limited to, control sequences, need not be contiguous with the nucleic acids, peptides, or proteins whose expression they control as long as they function to direct the expression thereof. Thus, for example, intervening untranslated yet transcribed sequences may be present between a promoter sequence and a nucleic acid of the present invention and the promoter sequence may still be considered "operably linked" to the coding sequence. Other such control sequences include, but are not limited to, polyadenylation signals, termination signals, and ribosome binding sites.

The term "hybridization" refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. The effects of base incompatibility may be measured by quantifying the rate at which two strands anneal, this may provide information as to the similarity in base sequence between the two strands being annealed.

The term "isolated" refers to material, such as a nucleic acid, a peptide, or a protein, which is: (1) substantially or essentially free from components that normally accompany or interact with it as found in its naturally occurring environment. The terms "substantially or essentially free" are used to refer to a material, which is at least 80% free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation. The term "therapeutically effective amount" or an "amount effective" of one or more of the active agents of the present invention is an amount that is sufficient to provide a therapeutic effect. Generally, an effective amount of the active agents that can be employed ranges from about 0.000001 mg/kg body weight to about 100 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "drug" as used herein refers to a therapeutic agent or any substance, other than food, used in the prevention, diagnosis, alleviation, treatment, or cure of disease.

The term "reduce" or "reducing" as used herein refers to limit occurrence of the disorder in individuals at risk of developing the disorder.

The term "modulate" as used herein means to regulate, alter, adapt, or adjust to a certain measure or proportion.

The terms "inhibiting", "inhibit" or "inhibition" as used herein are used to refer to reducing the amount or rate of a process, to stopping the process entirely, or to decreasing, limiting, or blocking the action or function thereof. Inhibition may include a reduction or decrease of the amount, rate, action function, or process by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99% when compared to a reference substance, wherein the reference substance is a substance that is not inhibited.

The term "kinase" as used herein refers to a type of enzyme that transfers phosphate groups from high-energy donor molecules to specific target molecules or substrates. High-energy donor groups may include, but are not limited, to ATP.

The term "kinase inhibiting peptide" (or "KIP") as used herein refers to an amino acid sequence comprising a KIP amino acid sequence. A KIP amino acid sequence within a peptide or peptidomimetic conveys to the peptide or peptidomimetic certain kinase inhibiting capabilities. KIP1, KIP2 and KIP3 are classes of KIP amino acid sequences.

The term "peptidomimetic" as used herein refers to a small protein-like chain designed to mimic a peptide. A peptidomimetic typically arises from modification of an existing peptide in order to alter the molecule's properties.

The term "kinase substrate" as used herein refers to a substrate that can be phosphorylated by a kinase.

The term "kinase activity" as used herein refers to kinase mediated phosphorylation of a kinase substrate.

The term "mammalian cell" as used herein refers to a cell derived from an animal of the class Mammalia. As used herein, mammalian cells may include normal, abnormal and transformed cells. Examples of mammalian cells utilized within the present invention, include, but are not limited to, neurons, epithelial cells, muscle cells, blood cells, immune cells, stem cells, osteocytes, endothelial cells and blast cells.

The term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, are contiguous and in the same reading frame.

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The term "peptide" as used herein refers to a polypeptide, protein or peptidomimetic. The terms "polypeptide", "peptide" and "protein" are used herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" refers to a chemical compound that consists of a heterocyclic base, a sugar, and one or more phosphate groups. In the most common nucleotides the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. The purines include adenine (A), and guanine (G); the pyrimidines include cytosine (C), thymine (T), and uracil (U).

The term "reduce" or "reducing" as used herein refers to a decrease in size or the slowing of the growth or proliferative rate of a cell of a neoplasm or hyperplasia.

The term "neoplasia" as used herein refers to the abnormal proliferation of cells that results in a neoplasm. The term "neoplasm" as used herein refers to an abnormal mass of tissue, the growth of which exceeds and is uncoordinated with that of the normal tissues, and persists in the same excessive manner after the cessation of the stimulus which evoked the change. A neoplasm can be benign, potentially malignant, or malignant. Benign neoplasms include uterine fibroids and melanocytic nevi (skin moles). These neoplasms do not transform into cancer. Potentially malignant neoplasms include carcinoma in situ. These neoplasms do not invade and destroy but, given enough time, will transform into a cancer. Malignant neoplasms are commonly called cancer. These neoplasms invade and destroy the surrounding tissue, may form metastases and eventually kill the subject.

The term "hyperplasia" as used herein is a general term referring to the proliferation of cells within an organ or tissue beyond that which is ordinarily seen in e.g. constantly dividing cells. Hyperplasia may result in the gross enlargement of an organ, the formation of a benign tumor, or may be visible only under a microscope. Hyperplasia is considered to be a physiological response to a specific stimulus, and the cells of a hyperplastic growth remain subject to normal regulatory control mechanisms. Hyperplasia may be in or on a subject. Hyperplasia may be due to any number of causes, including increased demand, chronic inflammatory response, hormonal dysfunctions, or compensation for damage or disease elsewhere. Hyperplasia may be harmless and occur on a particular tissue. Hyperplasia may also be induced artificially. Hyperplasia may also occur abnormally, and is associated with a variety of clinical diseases. Hyperplasia includes, but is not limited to, a neointimal hyperplasia of an artery; Keloids scars or hyperplastic scars; surgical adhesions; surgically induced hyperplasia; congenital adrenal hyperplasia; endometrial hyperplasia; benign prostatic hyperplasia; hyperplasia of the breast; focal epithelial hyperplasia; sebaceous hyperplasia; compensatory liver hyperplasia and such like hyperplastic conditions.

The term "subject" or "individual" or "patient" are used interchangeably to refer to a member of an animal species of mammalian origin, including but not limited to, a mouse, a rat, a cat, a goat, sheep, horse, hamster, ferret, pig, a dog, a guinea pig, a rabbit and a primate, such as, for example, a monkey, ape, or human.

The term "treat" or "treating" as used herein refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously symptomatic for the disorder. The term "disease" or "disorder" as used herein refers to an impairment of health or a condition of abnormal functioning. The term "syndrome" as used herein refers to a pattern of symptoms indicative of some disease or condition. The term "injury" as used herein refers to damage or harm to a structure or function of the body caused by an outside agent or force, which may be physical or chemical. The term "condition" as used herein refers to a variety of health states and is meant to include disorders or diseases caused by any underlying mechanism or disorder, injury, and the promotion of healthy tissues and organs. Disorders may include, for example, but not limited to, neoplasia or hyperplasia.

Compositions: Kinase Inhibiting Peptides (KIPs)

According to one aspect, the present invention provides a kinase inhibiting composition, the composition comprising a therapeutically effective amount of a kinase inhibiting peptide, wherein the kinase inhibiting peptide inhibits kinase activity of a kinase enzyme.

According to one embodiment, the kinase inhibiting peptide is a cyclin-dependent-kinase inhibitor. According to one such embodiment, the kinase inhibiting peptide is a peptide having the amino acid sequence of the general Formula IV:

Q1-Z1-Z2-Z3-Z4-Z5-Z6-Q2        [Formula IV] [SEQ ID NO: 193]

wherein Q1 and Q2 are independently absent or present, and wherein if Q1 and Q2 are present, Q1 and Q2 comprise a polypeptide of the sequence:

X1-X2-X3-X4-X5-X6-X7-X8-X9-X10-X11        [Formula IV(a)] [SEQ ID NO: 194]

wherein

X1 is any amino acid except K, or is absent;

X2 is present or is absent; in some such embodiments when X2 is present, X2 is any amino acid; in some such embodiments, when X2 is present, X2 is a hydrophobic amino acid [SEQ ID NO: 212]; in some such embodiments, when X2 is present, X2 is A [SEQ ID NO: 213];

X3 is any amino acid; in some such embodiments, X3 is a hydrophobic amino acid [SEQ ID NO: 214] in some such embodiments, X3 is selected from the group consisting of L, I, V, and M [SEQ ID NO: 215];

X4 is any amino acid; in some such embodiments, X4 is selected from the group consisting of Q, A, and N [SEQ ID NO: 216];

X5 is any basic amino acid;

X6 is any amino acid; in some such embodiments, X6 is selected from the group consisting of Q and N [SEQ ID NO: 217];

X7 is any amino acid; in some such embodiments, X7 is a hydrophobic amino acid [SEQ ID NO: 218]; in some such embodiments, X7 is selected from the group consisting of L, I, V and M [SEQ ID NO: 219];

X8 is any amino acid; in some such embodiments, X8 is selected from the group consisting of G, A, C, S, T and Y [SEQ ID NO: 220];

X9 is any amino acid; in some such embodiments, X9 is a hydrophobic amino acid [SEQ ID NO: 221]; in some such embodiments, X9 is selected from the group consisting of L, I, V and M [SEQ ID NO: 222]; in some such embodiments, X9 is V [SEQ ID NO: 223];

X10 is any amino acid;

X11 is any amino acid, or is absent;

and wherein Z1 and Z2 are present;

wherein Z3 is present or absent, wherein Z4 is absent or present, but if Z4 is present, Z3 is present, wherein Z5 is absent or present, but if Z5 is present, Z3 and Z4 are present; wherein Z6 is absent or present, but if Z6 is present, Z3, Z4 and Z5 are present; and each of Z1, Z2, Z3, Z4, Z5, and Z6, is a peptide selected from the group consisting of:

(a) X1-X2-B1-B2-X3-B3-X4   [Formula IV(b)] [SEQ ID NO: 195], wherein each of X1, X3 and X4 is a hydrophobic amino acid; X2 is any amino acid; and, in some embodiments, X2 is a hydrophobic amino acid, H or N; and wherein each of B1, B2 and B3 is a basic amino acid;

(b) X1-X2-B1-B2-X3-B3   [Formula IV(c)] [SEQ ID NO: 196], wherein each of X1 and X3 is a hydrophobic amino acid, X2 is any amino acid, and, in some embodiments, X2 is a hydrophobic amino acid; H or N; and wherein each of B1, B2, and B3 is a basic amino acid;

(c) X1-X2-B1-B2-X3   [Formula IV(d)] [SEQ ID NO: 197], wherein each of X1 and X3 is a hydrophobic amino acid; X2 is any amino acid; and, in some embodiments, X2 is a hydrophobic amino acid; H, or N; and wherein each of B1 and B2 is a basic amino acid;

(d) X1-B1-B2-X2-B3-X3   [Formula IV(e)] [SEQ ID NO: 198], wherein X1 is any amino acid; and, in some embodiments, X1 is a hydrophobic amino acid; H, or N; each of X2 and X3 is a hydrophobic amino acid, and each of B1, B2, and B3 is a basic amino acid;

(e) X1-B1-B2-X2-B3   [Formula IV(f)] [SEQ ID NO: 199], wherein X1 is a hydrophobic amino acid, H or N; X2 is any hydrophobic amino acid; and each of B1, B2, and B3 is a basic amino acid;

(f) X1-B1-B2-X2   [Formula IV(g)] [SEQ ID NO: 200], wherein X1 is any amino acid; and, in some embodiments, X1 is a hydrophobic amino acid, H or N; X2 is a hydrophobic amino acid; and each of B1 and B2 is a basic amino acid;

(g) X1-X2-B1-B2   [Formula IV(h)] [SEQ ID NO: 201], wherein X1 is a hydrophobic amino acid, X2 is any amino acid, and, in some embodiments, X2 is a hydrophobic amino acid, H or N; and each of B1 and B2 is a basic amino acid;

(h) X1-X2-B1-X3-X4   [Formula IV(i)] [SEQ ID NO: 202], wherein each of X1, X3, and X4 is a hydrophobic amino acid; X2 is any amino acid, and, in some embodiments, X2 is a hydrophobic amino acid, H or N; and B1 is a basic amino acid;

(i) X1-B1-X2-X3   [Formula IV(j)] [SEQ ID NO: 203], wherein X1 is any amino acid, and, in some embodiments, X1 is hydrophobic amino acid, H or N; X2 is any amino acid, a hydrophobic amino acid or Q; X3 is a hydrophobic amino acid; and B1 is a basic amino acid;

(j) X1-X2-B1-X3   [Formula IV(k)] [SEQ ID NO: 204], wherein each of X1 and X3 is a hydrophobic amino acid; X2 is any amino acid, and, in some embodiments, X2 is a hydrophobic amino acid, H or N; and B1 is a basic amino acid;

(k) B1-B2-X1-X2-B3-X3   [Formula IV(l)] [SEQ ID NO: 205], wherein each of X1, X2, and X3 is a hydrophobic amino acid; and each of B1, B2, and B3 is a basic amino acid;

(l) B1-B2-X1-X2-B3   [Formula IV(m)] [SEQ ID NO: 206], wherein each of X1 and X2 is a hydrophobic amino acid; and each of B1, B2, and B3 is a basic amino acid;

(m) B1-B2-X1-X2   [Formula IV(n)] [SEQ ID NO: 207], wherein each of X1 and X2 is a hydrophobic amino acid; and each of B1 and B2 is a basic amino acid;

(n) B1-X1-X2-B2-B3-X3   [Formula IV(o)] [SEQ ID NO: 208], wherein each of X1, X2, and X3 is a hydrophobic amino acid; and each of B1, B2, and B3 is a basic amino acid;

(o) B1-X1-X2-B2-B3   [Formula IV(p)] [SEQ ID NO: 209], wherein each of X1 and X2 is a hydrophobic amino acid, and each of B1, B2, and B3 is a basic amino acid;

(p) B1-X1-X2-B2   [Formula IV(q)] [SEQ ID NO: 210]

wherein each of X1 and X2 is a hydrophobic amino acid; and each of B1 and B2 is a basic amino acid; with the proviso that if Q2 is present, the two amino acids immediately preceding Q2 as part of Z2, Z3, Z4, Z5, or Z6 cannot be KA.

In another embodiment of the isolated polypeptide according to general Formula IV, Q1, Z3, Z4, Z5, and Z6 are absent [SEQ ID NO: 211].

In some such embodiments, the kinase inhibiting peptide is a peptide having an amino acid sequence selected from the group consisting of HRRIKAWLKKILALARQLGVAA [SEQ ID NO: 192]; WLRRIKAWLRRIKALARQLGVAA [SEQ ID NO: 113]; AND WLRRIKAWLRRALARQLGVA [SEQ ID NO: 177]. In some such embodiments, the amino acid sequence of the kinase inhibiting peptide is HRRIKAWLKKILALARQLGVAA [SEQ ID NO: 192]. In some such embodiments, the amino acid sequence of the kinase inhibiting peptide is WLRRIKAWLRRIKALARQLGVAA [SEQ ID NO: 113]. In some such embodiments, the amino acid sequence of the kinase inhibiting peptide is WLRRIKAWLRRALARQLGVA [SEQ ID NO: 177].

According to one such embodiment, the kinase inhibiting peptide is KIP1. In some such embodiments, the KIP1 peptide is a peptide of at least 14 amino acids, at least 21 amino acids, at least 28 amino acids, or a maximum of 35 amino acids. In some such embodiments, the KIP1 peptide is a peptide having an amino acid sequence according to Formula I: $(XXBBXBX)_n$, wherein X is any amino acid, B is a basic amino acid, such as, for example, K, R, H, and n is an integer between 2 and 5.

According to another such embodiment, the kinase inhibiting peptide is KIP2. In some such embodiments, the KIP2 peptide is a peptide of 11 amino acids. In some such embodiments, the KIP2 peptide is a peptide having an amino acid sequence according to Formula II: X1-X2-X3-X4-X5-X6-X7-X8-X9-X10-X11; wherein X1 is present or absent, and if present X1 is selected from the group consisting of A, F, I, L, V, W, and Y, or is an aromatic hydrophobic amino acid; X2 is any amino acid; X3 is selected from the group consisting of Q, N, R, and K; X4 is selected from the group consisting of A, G, I, L, V, R and K, or is an aliphatic amino acid; X5 is selected from the group consisting of A, G, I, L, V, R and K, or is an aliphatic amino acid; X6 is selected from the group consisting of A, G, I, L, V, R and K, or is an aliphatic amino acid; X7 is basic amino acid; X8 is selected from the group consisting of Q, NR, and K; X9 is selected from the group consisting of A, G, I, L, V, R and K, or is an aliphatic amino acid; X10 is present or absent provided that if X10 is absent then X11 is also absent; if X10 is present, X10 is basic amino acid; and X11 is present or absent; if X11 is present, X11 is selected from group consisting of A, G, I, L, V, R and K, or is an aliphatic amino acid. In some such embodiments, X1 is F, W, or Y. In some such embodiments, X3 is R. In some such embodiments, X4 is R or K. In some such embodiments, X5 is R or K. In some such embodiments, X6 is R or K. In some such embodiments, X8 is Q or N. In some such embodiments, X9 is R or K. In some such embodiments, X10 is R or K. In some such embodiments, X11 is R or K.

According to another such embodiment, the kinase inhibiting peptide is KIP3. In some such embodiments, the KIP3 peptide is a peptide of at least 12 amino acids, at least 18 amino acids, at least 24 amino acids, or at least 30 amino acids. The KIP3 amino acid sequence is of the general Formula III: $(XBBXBX)_n$ wherein X is any amino acid, B is a basic amino acid, such as, for example, K, R, H and n is an integer between 2 and 5.

According to another such embodiment, the kinase inhibiting peptide is KIP4. In some such embodiments, the KIP4 peptide is a peptide of at least 16 amino acids, at least 24 amino acids, at least 32 amino acids, or at least 40 amino acids. In some such embodiments, the KIP4 peptide is a peptide having an amino acid sequence according to Formula V: $(XXBBXBXX)_n$ [SEQ ID NO: 224] wherein X is any amino acid, B is a basic amino acid, such as, for example, K, R, or H [SEQ ID NO: 225], and n is an integer between 2 and 5.

According to another embodiment, the kinase inhibiting peptide is a peptide having an amino acid sequence according to Formula VI:

Z1-X1-X2-X3-X4X5-X6-X7-X8-X9-X10-Z2    [Formula VI] [SEQ ID NO: 226], wherein each of Z1 and Z2 is absent or is a transduction domain;
X1 is absent or present, and if present is selected from the group consisting of A, KA, KKA, KKKA [SEQ ID NO: 186], and RA;
X2 is an aliphatic amino acid or is selected from the group consisting of G, L, A, V, I, M, Y, W, and F;
X3 is an aliphatic amino acid or is selected from the group consisting of V, L, I, A, G, Q, N, S, T, and C;
X4 is selected from the group consisting of Q, N, H, R and K;
X5 is selected from the group consisting of Q and N;
X6 is an aliphatic amino acid or is selected from the group consisting of C, A, G, L, V, I, M, Y, W, and F;
X7 is an aliphatic amino acid or is selected from the group consisting of S, A, C, T, and G;
X8 is selected from the group consisting of V, L, I, and M;
X9 is absent or is any amino acid; and
X10 is absent or is any amino acid.

In some such embodiments, the kinase inhibiting peptide is a peptide having an amino acid sequence selected from the group consisting of KAFAKLAARLYRKALARQLGVAA [SEQ ID NO: 173]; FAKLAARLYRKALARQLGVAA [SEQ ID NO: 163]; AND WLRRIKAWLRRIKALNRQLGVAA [SEQ ID NO: 142]. In some such embodiments, the amino acid sequence of the kinase inhibiting peptide is KAFAKLAARLYRKALARQLGVAA [SEQ ID NO: 173]. In some such embodiments, the amino acid sequence of the kinase inhibiting peptide is FAKLAARLYRKALARQLGVAA [SEQ ID NO: 163]. In some such embodiments, the amino acid sequence of the kinase inhibiting peptide is WLRRIKAWLRRIKALNRQLGVAA [SEQ ID NO: 142].

According to another embodiment, the kinase inhibiting peptide is a kinase inhibiting peptide of Table 1.

TABLE 1

Additional KIP amino acid sequences

| | Amino Acid Sequence | [SEQ ID NO:] |
|---|---|---|
| 1 | $(R)_{4-9}$ | [SEQ ID NO: 1] |
| 2 | GRKKRRQRRRPPQ | [SEQ ID NO: 2] |
| 3 | AYARAAARQARA | [SEQ ID NO: 3] |
| 4 | DAATATRGRSAASRPTERPRAPARSASRPRRPVE | [SEQ ID NO: 4] |
| 5 | GWTLNSAGYLLGLINLKALAALAKKIL | [SEQ ID NO: 5] |
| 6 | PLSSIFSRIGDP | [SEQ ID NO: 6] |
| 7 | AAVALLPAVLLALLAP | [SEQ ID NO: 7] |
| 8 | AAVLLPVLLAAP | [SEQ ID NO: 8] |
| 9 | VTVLALGALAGVGVG | [SEQ ID NO: 9] |
| 10 | GALFLGWLGAAGSTMGAWSQP | [SEQ ID NO: 10] |
| 11 | GWTLNSAGYLLGLINLKALAALAKKIL | [SEQ ID NO: 11] |
| 12 | KLALKLALKALKAALKLA | [SEQ ID NO: 12] |
| 13 | KETWWETWWTEWSQPKKKRKV | [SEQ ID NO: 13] |
| 14 | KAFAKLAARLYRKA | [SEQ ID NO: 14] |
| 15 | KAFAKLAARLYRAA | [SEQ ID NO: 15] |
| 16 | AAFAKLAARLYRKA | [SEQ ID NO: 16] |
| 17 | KAFAKLAARLYRKA | [SEQ ID NO: 17] |
| 18 | KAFAKLAARLYRKAGC | [SEQ ID NO: 18] |
| 19 | KAFAKLAARLYRAAGC | [SEQ ID NO: 19] |
| 20 | AAFAKLAARLYRKAGC | [SEQ ID NO: 20] |
| 21 | KAFAKLAARLYRKAGC | [SEQ ID NO: 21] |
| 22 | KAFAKLAAQLYRKAGC | [SEQ ID NO: 22] |
| 23 | AGGGGYGRKKRRQRRR | [SEQ ID NO: 23] |
| 24 | $(WLRRIKA)_{1-3}$ | [SEQ ID NO: 176] |
| 25 | YGRKKRRQRRR | [SEQ ID NO: 24] |
| 26 | YARAAARQARA | [SEQ ID NO: 25] |

TABLE 1-continued

Additional KIP amino acid sequences

| # | Amino Acid Sequence | [SEQ ID NO:] |
|---|---|---|
| 27 | RQRRKKRG | [SEQ ID NO: 26] |
| 28 | GRKKRRQR | [SEQ ID NO: 27] |
| 29 | YARAAARQARAKALNRQLGVA | [SEQ ID NO: 28] |
| 30 | YGRKKRRQRRRKALNRQLGVA | [SEQ ID NO: 29] |
| 31 | GRKKRRQRKALNRQLGVA | [SEQ ID NO: 30] |
| 32 | RQRRKKRGKALNRQLGVA | [SEQ ID NO: 31] |
| 33 | WLRRIKAWLRRIKAKALNRQLGVA | [SEQ ID NO: 32] |
| 34 | WLRRIKAWLRRIKAWLRRIKAKALNRQLGVA | [SEQ ID NO: 33] |
| 35 | YARAAARQARAKKKALNRQLGVA | [SEQ ID NO: 34] |
| 36 | YGRKKRRQRRRKKKALNRQLGVA | [SEQ ID NO: 35] |
| 37 | RQRRKKRGKKKALNRQLGVA | [SEQ ID NO: 36] |
| 38 | GRKKRRQRKKKALNRQLGVA | [SEQ ID NO: 37] |
| 39 | WLRRIKAWLRRIKAKKKALNRQLGVA | [SEQ ID NO: 38] |
| 40 | WLRRIKAWLRRIKAWLRRIKAKKKALNRQLGVA | [SEQ ID NO: 39] |
| 41 | YARAAARQARAKKKALNRGLGVA | [SEQ ID NO: 40] |
| 42 | YGRKKRRQRRRKKKALNRGLGVA | [SEQ ID NO: 41] |
| 43 | RQRRKKRGKLKALNRGLGVA | [SEQ ID NO: 42] |
| 44 | GRKKRRQRKKKALNRGLGVA | [SEQ ID NO: 43] |
| 45 | WLRRIKAWLRRIKAKKKALNRGLGVA | [SEQ ID NO: 44] |
| 46 | WLRRIKAWLRRIKAWLRRIKAKKKALNRGLGVA | [SEQ ID NO: 45] |
| 47 | YARAAARQARAKKKALNRQLAVA | [SEQ ID NO: 46] |
| 48 | YGRKKRRQRRRKKKALNRQLAVA | [SEQ ID NO: 47] |
| 49 | RQRRKKRGKKKALNRQLAVA | [SEQ ID NO: 48] |
| 50 | GRKKRRQRKKKALNRQLAVA | [SEQ ID NO: 49] |
| 51 | WLRRIKAWLRRIKAKKKALNRQLAVA | [SEQ ID NO: 50] |
| 52 | WLRRIKAWLRRIKAWLRRIKAKKKALNRQLAVA | [SEQ ID NO: 51] |
| 53 | YARAAARQARAKKKALARQLGVA | [SEQ ID NO: 52] |
| 54 | YGRKKRRQRRRKKKALARQLGVA | [SEQ ID NO: 53] |
| 55 | RQRRKKRGKKKALARQLGVA | [SEQ ID NO: 54] |
| 56 | GRKKRRQRKKKALARQLGVA | [SEQ ID NO: 55] |
| 57 | WLRRIKAWLRRIKAKKKALARQLGVA | [SEQ ID NO: 56] |
| 58 | WLRRIKAWLRRIKAWLRRIKAKKKALARQLGVA | [SEQ ID NO: 57] |
| 59 | YARAAARQARAKALNRGLGVA | [SEQ ID NO: 58] |
| 60 | YGRKKRRQRRRKALNRGLGVA | [SEQ ID NO: 59] |
| 61 | RQRRKKRGKALNRGLGVA | [SEQ ID NO: 60] |
| 62 | GRKKRRQRKALNRGLGVA | [SEQ ID NO: 61] |
| 63 | WLRRIKAWLRRIKAKALNRGLGVA | [SEQ ID NO: 62] |
| 64 | WLRRIKAWLRRIKAWLRRIKAKALNRGLGVA | [SEQ ID NO: 63] |
| 65 | YARAAARQARAKALNRQLAVA | [SEQ ID NO: 64] |
| 66 | YGRKKRRQRRRKALNRQLAVA | [SEQ ID NO: 65] |
| 67 | RQRRKKRGKALNRQLAVA | [SEQ ID NO: 66] |
| 68 | GRKKRRQRKALNRQLAVA | [SEQ ID NO: 67] |
| 69 | WLRRIKAWLRRIKAKALNRQLAVA | [SEQ ID NO: 68] |
| 70 | WLRRIKAWLRRIKAWLRRIKAKALNRQLAVA | [SEQ ID NO: 69] |
| 71 | YARAAARQARAKALARQLGVA | [SEQ ID NO: 70] |
| 72 | YGRKKRRQRRRKALARQLGVA | [SEQ ID NO: 71] |
| 73 | RQRRKKRGKALARQLGVA | [SEQ ID NO: 72] |
| 74 | GRKKRRQRKALARQLGVA | [SEQ ID NO: 73] |
| 75 | WLRRIKAWLRRIKAKALARQLGVA | [SEQ ID NO: 74] |
| 76 | WLRRIKAWLRRIKAWLRRIKAKALARQLGVA | [SEQ ID NO: 75] |
| 77 | YARAAARQARAKKKALNRGLGVAA | [SEQ ID NO: 76] |
| 78 | YGRKKRRQRRRKKKALNRGLGVAA | [SEQ ID NO: 77] |
| 79 | RQRRKKRGKKKALNRGLGVAA | [SEQ ID NO: 78] |
| 80 | GRKKRRQRKKKALNRGLGVAA | [SEQ ID NO: 79] |
| 81 | WLRRIKAWLRRIKAKKKALNRGLGVAA | [SEQ ID NO: 80] |
| 82 | WLRRIKAWLRRIKAWLRRIKAKKKALNRGLGVAA | [SEQ ID NO: 81] |
| 83 | YARAAARQARAKKKALNRQLAVAA | [SEQ ID NO: 82] |
| 84 | YGRKKRRQRRRKKKALNRQLAVAA | [SEQ ID NO: 83] |
| 85 | RQRRKKRGKKKALNRQLAVAA | [SEQ ID NO: 84] |
| 86 | GRKKRRQRKKKALNRQLAVAA | [SEQ ID NO: 85] |
| 87 | WLRRIKAWLRRIKAKKKALNRQLAVAA | [SEQ ID NO: 86] |
| 88 | WLRRIKAWLRRIKAWLRRIKAKKKALNRQLAVAA | [SEQ ID NO: 87] |
| 89 | YARAAARQARAKKKALARQLGVAA | [SEQ ID NO: 88] |
| 90 | YGRKKRRQRRRKKKALARQLGVAA | [SEQ ID NO: 89] |
| 91 | RQRRKKRGKKKALARQLGVAA | [SEQ ID NO: 90] |
| 92 | GRKKRRQRKKKALARQLGVAA | [SEQ ID NO: 91] |
| 93 | WLRRIKAWLRRIKAKKKALARQLGVAA | [SEQ ID NO: 92] |
| 94 | WLRRIKAWLRRIKAWLRRIKAKKKALARQLGVAA | [SEQ ID NO: 93] |
| 95 | YARAAARQARAKALNRGLGVAA | [SEQ ID NO: 94] |
| 96 | YGRKKRRQRRRKALNRGLGVAA | [SEQ ID NO: 95] |
| 97 | RQRRKKRGKALNRGLGVAA | [SEQ ID NO: 96] |

TABLE 1-continued

Additional KIP amino acid sequences

| | Amino Acid Sequence | [SEQ ID NO:] |
|---|---|---|
| 98 | GRKKRRQRKALNRGLGVAA | [SEQ ID NO: 97] |
| 99 | WLRRIKAWLRRIKAKALNRGLGVAA | [SEQ ID NO: 98] |
| 100 | WLRRIKAWLRRIKAWLRRIKAKALNRGLGVAA | [SEQ ID NO: 99] |
| 101 | YARAAARQARAKALNRQLAVAA | [SEQ ID NO: 100] |
| 102 | YGRKKRRQRRRKALNRQLAVAA | [SEQ ID NO: 101] |
| 103 | RQRRKKRGKALNRQLAVAA | [SEQ ID NO: 102] |
| 104 | GRKKRRQRKALNRQLAVAA | [SEQ ID NO: 103] |
| 105 | WLRRIKAWLRRIKAKALNRQLAVAA | [SEQ ID NO: 104] |
| 106 | WLRRIKAWLRRIKAWLRRIKAKALNRQLAVAA | [SEQ ID NO: 105] |
| 107 | YARAAARQARAKALARQLGVAA | [SEQ ID NO: 106] |
| 108 | YGRKKRRQRRRKALARQLGVAA | [SEQ ID NO: 107] |
| 109 | RQRRKKRGKALARQLGVAA | [SEQ ID NO: 108] |
| 110 | GRKKRRQRKALARQLGVAA | [SEQ ID NO: 109] |
| 111 | WLRRIKAWLRRIKAKALARQLGVAA | [SEQ ID NO: 110] |
| 112 | WLRRIKAWLRRIKAWLRRIKAKALARQLGVAA | [SEQ ID NO: 111] |
| 113 | WLRRIKAWLRRIKALARQLGVAA | [SEQ ID NO: 113] |
| 114 | WLRRIKAWLRRIKALNRQLGVAA | [SEQ ID NO: 142] |
| 115 | FAKLAARLYRKA | [SEQ ID NO: 160] |
| 116 | FAKLAARLYRKAGC | [SEQ ID NO: 161] |
| 117 | FAKLAARLYRKALNRQLGVAA | [SEQ ID NO: 162] |
| 118 | FAKLAARLYRKALARQLGVAA | [SEQ ID NO: 163] |
| 119 | FAKLAARLYRKALNRQLGVA | [SEQ ID NO: 164] |
| 120 | FAKLAARLYRKALARQLGVA | [SEQ ID NO: 165] |
| 121 | HRRIKAWLKKIKALARQLGVAA | [SEQ ID NO: 166] |
| 122 | WLRRIKAHRRIKALARQLGVAA | [SEQ ID NO: 167] |
| 123 | WLRRIKAWLRR | [SEQ ID NO: 168] |
| 124 | WLRRIKAWLRRALNRQLGVAA | [SEQ ID NO: 169] |
| 125 | YARAAARQARAKALNRQLGVAA | [SEQ ID NO: 147] |
| 126 | YARAAARQARALNRQLGVAA | [SEQ ID NO: 170] |
| 127 | YARAAARQARALARQLGVAA | [SEQ ID NO: 171] |
| 128 | KAFAKLAARLYRKALNRQLGVAA | [SEQ ID NO: 172] |
| 129 | KAFAKLAARLYRKALARQLGVAA | [SEQ ID NO: 173] |
| 130 | KAFAKLAARLYRKALNRQLGVA | [SEQ ID NO: 174] |
| 131 | KAFAKLAARLYRKALARQLGVA | [SEQ ID NO: 175] |
| 132 | WLRRIKAWLRRALARQLGVA | [SEQ ID NO: 177] |

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

As used herein, "sequence identity" or "identity" in the context of two nucleic acid or polypeptide sequences refers to the residues in the two sequences which are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

According to another embodiment, the present invention provides an isolated nucleic acid that encodes a polypeptide having at least 85% amino acid sequence identity to KIP1, wherein the polypeptide inhibits kinase activity of a kinase enzyme. In some such embodiments, the isolated nucleic acid encodes a polypeptide with 100% amino acid sequence identity to KIP1, wherein the polypeptide inhibits kinase activity of a kinase enzyme. In some such embodiments, the KIP1 sequence is operably linked to a controllable regulatory element.

According to another embodiment, the present invention provides an isolated nucleic acid that encodes a polypeptide having at least 85% amino acid sequence identity to KIP2, wherein the polypeptide inhibits kinase activity of a kinase enzyme. In some such embodiments, the isolated nucleic acid encodes a polypeptide with 100% amino acid sequence identity to KIP2, wherein the polypeptide inhibits kinase activity of a kinase enzyme. In some such embodiments, the KIP2 sequence is operably linked to a controllable regulatory element.

According to another embodiment, the present invention provides an isolated nucleic acid that encodes a polypeptide having at least 85% amino acid sequence identity to KIP3, wherein the polypeptide inhibits kinase activity of a kinase enzyme. In some such embodiments, the isolated nucleic acid encodes a polypeptide with 100% amino acid sequence identity to KIP3, wherein the polypeptide inhibits kinase activity of a kinase enzyme. In some such embodiments, the KIP3 sequence is operably linked to a controllable regulatory element.

According to another embodiment, the present invention provides an isolated nucleic acid that encodes a polypeptide having at least 85% amino acid sequence identity to KIP4, wherein the polypeptide inhibits kinase activity of a kinase enzyme. In some such embodiments, the isolated nucleic acid encodes a polypeptide with 100% amino acid sequence identity to KIP4, wherein the polypeptide inhibits kinase activity of a kinase enzyme. In some such embodiments, the KIP4 sequence is operably linked to a controllable regulatory element.

According to another embodiment, the present invention provides an isolated nucleic acid that specifically hybridizes to mRNA encoding a peptide comprising a KIP1 or KIP2 amino acid sequence. The term "specifically hybridizes" as used herein refers to the process of a nucleic acid distinctively or definitively forming base pairs with complementary regions of at least one strand of DNA that was not originally paired to the nucleic acid. For example, a nucleic acid that may bind or hybridize to at least a portion of an mRNA of a cell encoding a peptide comprising a KIP sequence may be considered a nucleic acid that specifically hybridizes. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 90% sequence identity, or at least 100% sequence identity (i.e., complementary) with each other.

Methods of extraction of RNA are well-known in the art and are described, for example, in J. Sambrook et al., "Molecular Cloning: A Laboratory Manual" (Cold Spring Harbor Laboratory Press, Cold Spring Harbor, N.Y., 1989), vol. 1, ch. 7, "Extraction, Purification, and Analysis of Messenger RNA from Eukaryotic Cells," incorporated herein by this reference. Other isolation and extraction methods are also well-known, for example in F. Ausubel et al., "Current Protocols in Molecular Biology", John Wiley & Sons, 2007). Typically, isolation is performed in the presence of chaotropic agents, such as guanidinium chloride or guanidinium thiocyanate, although other detergents and extraction agents alternatively may be used. Typically, the mRNA is isolated from the total extracted RNA by chromatography over oligo(dT)-cellulose or other chromatographic media that have the capacity to bind the polyadenylated 3'-portion of mRNA molecules. Alternatively, but less preferably, total RNA can be used. However, it is generally preferred to isolate poly(A)+ RNA from mammalian sources.

According to another embodiment, the present invention provides an antibody or an antibody fragment that specifically binds to an amino acid sequence of a KIP peptide.

Methods of Inhibiting Kinase Activity

According to another aspect, the present invention provides a method for inhibiting kinase activity of a kinase enzyme, the method comprising the steps: (a) providing a kinase inhibiting composition, wherein the kinase inhibiting composition comprises an inhibitory amount of a kinase inhibiting peptide; (b) contacting the kinase inhibiting composition with a kinase enzyme such that the kinase inhibiting peptide associates with the kinase enzyme; and (c) reducing the kinase activity of the kinase enzyme.

According to another embodiment, the present invention provides a method for inhibiting kinase activity of a kinase enzyme, the method comprising the steps of: (a) providing a kinase inhibiting composition, wherein the kinase inhibiting composition comprises an inhibitory amount of a kinase inhibiting peptide, wherein the kinase inhibiting peptide further comprises a KIP1 peptide; (b) contacting the kinase inhibiting composition with a kinase enzyme such that the kinase inhibiting peptide associates with kinase enzyme; and (c) reducing the kinase activity of the kinase enzyme.

According to another embodiment, the present invention provides a method for inhibiting kinase activity of a kinase enzyme, the method comprising the steps of: (a) providing a kinase inhibiting composition, wherein the kinase inhibiting composition comprises an inhibitory amount of a kinase inhibiting peptide, wherein the kinase inhibiting peptide further comprises a KIP2 peptide; (b) contacting the kinase inhibiting composition with a kinase enzyme such that the kinase inhibiting peptide associates with the kinase enzyme; and (c) reducing the kinase activity of the kinase enzyme.

According to another embodiment, the present invention provides a method for inhibiting kinase activity of a kinase enzyme, the method comprising the steps of: (a) providing a kinase inhibiting composition, wherein the kinase inhibiting composition comprises an inhibitory amount of a kinase inhibiting peptide, wherein the kinase inhibiting peptide further comprises a KIP3 peptide; (b) contacting the kinase inhibiting composition with a kinase enzyme such that the kinase inhibiting peptide associates with the kinase enzyme; and (c) reducing the kinase activity of the kinase enzyme.

According to another embodiment, the present invention provides a method for lowering the enzymatic velocity of a kinase reaction, the method comprising the steps: (a) providing a kinase inhibiting composition, wherein the kinase inhibiting composition comprises an inhibitory amount of a kinase inhibiting peptide, wherein the kinase inhibiting peptide comprises a KIP1 peptide, (b) contacting the kinase inhibiting composition with a kinase enzyme such that the kinase inhibiting peptide associates with the kinase enzyme; and (c) lowering the enzymatic velocity of the kinase enzyme. In some such embodiments, the kinase enzyme is in a prokaryotic cell. In some such embodiments, the kinase enzyme is in a eukaryotic cell. In some such embodiments, the kinase inhibiting peptide is operably linked to a controllable regulatory element.

According to another embodiment, the present invention provides a method for lowering the enzymatic velocity of a kinase reaction, the method comprising the steps: (a) providing a kinase inhibiting composition, wherein the kinase inhibiting composition comprises an inhibitory amount of a kinase inhibiting peptide, wherein the kinase inhibiting peptide comprises a KIP2 peptide, (b) contacting the kinase inhibiting composition with the kinase enzyme such that the kinase inhibiting peptide associates with the kinase enzyme; and (c) lowering the enzymatic velocity of the kinase enzyme. In some such embodiments, the kinase enzyme is in a prokaryotic cell. In some such embodiments, the kinase enzyme is in a eukaryotic cell. In some such embodiments, the kinase inhibiting peptide is operably linked to a controllable regulatory element.

According to another embodiment, the kinase enzyme is a serine kinase. According to another embodiment, the kinase enzyme is a threonine kinase. According to another embodiment, the kinase enzyme is a tyrosine kinase. According to another embodiment, the kinase enzyme is a receptor tyrosine kinase. According to another embodiment, the kinase enzyme is a serine/threonine kinase.

According to another embodiment, the kinase enzyme is a kinase enzyme selected from the group consisting of: Ab 1, Akt/PKB, AMPK, Arg, Ask, Aurora-A, Axl, Blk, Bmx, Brk, BTK, CaMKI, CaMKIδ, CaMKIIβ, CaMKIIγ, CaMKI1β, Casein Kinase, Cdk, CDK9/cyclin, CKly1, CKly2, CKly3, Cklδ, CK2α, CK2, CHK, CDK1/cyclinB, CHK1, CHK2 mutants, CK1δ, CK2, c-Kit, CLK2, CLK3, Cott, Csk, DAPK1, DCAMKL2, DDR, DYRK2, EGFR, Ephs, EphA2, FAK, Fer, Fes/Fps, FGFR, FGFR1, Fgr, Fit, Flt3, Flt4, Fms/CSF-1 R, Fyn, GRK5, GRK6, GRK7, GSK, CSK3, Hck, HER/ErbB, HIPK1, HIPK2, HIPK3, IGF-1, ICF IR, IKK, Insulin R, IRAK, IRAK1, IRAK4, JAK, JAK1, JAK2, JAK3, JNK/SAPK, KDR, Lck, LIMK, LIMK1, LOK, Lyn, MAPK, MAPK1, MAPKAP Kinase, MEK, MEK1, MELK, Met, Mer, MINK, MKK, MLCK, MLK1, MRCKa, MSK1, MST, MST3, NEK, NEK3, NEK9, PDGFR, PDGFRα, PDGFRβ, PDK, PhKγ2, PI 3-Kinase, PIM, Pim-1, Pim-2, Pim-3, PKC, PKCβ1, PKCδ, PKD2, PKR, PKA, PKBβ, PKCβI, PKCδ, PKG1, PKG1α, PKG1β, PKR, PLK, PRAK, PTK5, Pyk, Raf, Rct, RIPK2, ROK/ROCK, ROCK-I, Ron, Ros, Rse, Rsk4, Rsk/MAPKAP Kinase, S6 Kinase, Rsk2, SAPK2a, SGK, c-Src, Src(1-530), Src, Syk, TAK1, TAO1, TAO2, TBK, Tie2/TEK, TLK2, Trk, TSSK2, TrkA, Txk, ULK3, Ulk2, VRK2, WEE, Yes, ZAP-70 and ZIPK.

In some such embodiments, the kinase enzyme is selected from the group consisting of a ROCK kinase, a Src kinase, a PKC kinase and a Trk kinase. In some such embodiments, the kinase enzyme is a ROCK kinase. In some such embodiments, the kinase enzyme is ROCK-1. In some such embodiments, the kinase enzyme is a Src kinase. In some such embodiments, the kinase enzyme is SRrc(1-530). In some such embodiments, the kinase enzyme is a PKC kinase. In some such embodiments, the kinase enzyme is PKCβ1 or PKCδ. In some such embodiments, the kinase enzyme is a Trk kinase. In some such embodiments, the kinase enzyme is TrkA.

According to another embodiment, the present invention provides a method of inhibiting mRNA translation of an mRNA$_{KIP}$ molecule, the method comprising the steps: (a) providing a kinase inhibiting composition, wherein the kinase inhibiting composition comprises an inhibitory amount of an isolated nucleic acid that encodes a polypeptide having 100% amino acid sequence identity to KIP1, wherein the polypeptide inhibits kinase activity of a kinase enzyme; (b) contacting the kinase inhibiting composition of step (a) with an mRNA$_{KIP}$ molecule such that the isolated nucleic acid hybridizes with the mRNA$_{KIP}$; and (c) inhibiting the mRNA translation of the mRNA$_{KIP}$ molecule. As used herein, the term "mRNA$_{KIP}$" refers to an mRNA molecule that upon mRNA translation, yields a KIP molecule. In some such embodiments, the mRNA translation of the mRNA$_{KIP}$ molecule yields a KIP1 molecule. In some such embodiments, the mRNA$_{KIP}$ molecule comprises a KIP sequence operably linked to a controllable regulatory element. In some such embodiments, in step (a) the isolated nucleic acid encodes a polypeptide having about 85% amino acid sequence identity to a KIP1 peptide.

According to another embodiment, the present invention provides a method of inhibiting mRNA translation of an mRNA$_{KIP}$ molecule, the method comprising the steps: (a) providing a kinase inhibiting composition, wherein the kinase inhibiting composition comprises an inhibitory amount of an isolated nucleic acid that encodes a polypeptide having 100% amino acid sequence identity to a KIP2 peptide, wherein the polypeptide inhibits kinase activity of a kinase enzyme; (b) contacting the kinase inhibiting composition of step (a) with an mRNA$_{KIP}$ molecule such that the isolated nucleic acid hybridizes with the mRNA$_{KIP}$; and (c) inhibiting the mRNA translation of the mRNA$_{KIP}$ molecule. In some such embodiments, the mRNA translation of the mRNA$_{KIP}$ molecule yields a KIP2 molecule. In some such embodiments, the mRNA$_{KIP}$ molecule comprises a KIP sequence operably linked to a controllable regulatory element. In some such embodiments, in step (a) the isolated nucleic acid encodes a polypeptide having about 85% amino acid sequence identity to a KIP2 peptide.

According to another embodiment, the present invention provides a method of inhibiting a kinase inhibitory function of a KIP1 peptide, the method comprising the steps: (a) providing a kinase inhibiting composition, wherein the kinase inhibiting composition comprises a therapeutically effective amount of an antibody specific to an epitope of a kinase inhibiting peptide amino acid sequence, wherein the kinase inhibiting peptide amino acid sequence is a KIP1 peptide amino acid sequence; (b) contacting the kinase inhibiting composition of step (a) with a KIP1 peptide such that the antibody associates with the KIP1 peptide; and (c) inhibiting the kinase inhibitory function of the kinase inhibiting peptide.

According to another embodiment, the present invention provides a method of inhibiting the kinase inhibitory function of a KIP2 peptide, the method comprising the steps: (a) providing a kinase inhibiting composition, wherein the kinase inhibiting composition comprises a therapeutically effective amount of an antibody specific to an epitope of a kinase inhibiting peptide amino acid sequence, wherein the kinase inhibiting peptide amino acid sequence is a KIP2 peptide amino acid sequence; (b) contacting kinase inhibiting composition of step (a) with a KIP2 peptide such that the antibody associates with the KIP2 peptide; and (c) inhibiting the kinase inhibitory function of the kinase inhibiting peptide.

Inhibiting Disorders

According to another aspect, the present invention provides a method for inhibiting hyperplasia of a cell population, the method comprising the steps: (a) providing a therapeutically effective amount of a kinase inhibiting composition to a subject in need thereof, wherein the kinase inhibiting composition comprises an isolated nucleic acid that encodes a polypeptide having 100% amino acid sequence identity to a KIP peptide, wherein the polypeptide inhibits kinase activity of a kinase enzyme; (b) contacting the kinase inhibiting composition of step (a) with at least one hyperplastic cell such that the isolated nucleic acid associates with the at least one hyperplastic cell; and (c) inhibiting the hyperplasia. In another embodiment, the isolated nucleic acid of step (a) further comprises a controllable regulatory element.

According to another aspect, the present invention provides a method for inhibiting hyperplasia of a cell population, the method comprising the steps: (a) providing a therapeutically effective amount of a kinase inhibiting composition to a subject in need thereof, wherein the kinase inhibiting composition comprises an inhibiting amount of a kinase inhibiting peptide, wherein the kinase inhibiting peptide comprises a KIP peptide, (b) contacting the kinase inhibitory composition with at least one hyperplastic cell such that the kinase inhibiting peptide associates with the at least one hyperplastic cell; and (c) inhibiting the hyperplasia. In some such embodiments, the kinase inhibiting peptide of step (a) is operably linked to a controllable regulatory element.

The term "growth" as used herein refers to a process of becoming larger, longer or more numerous, or an increase in size, number, or volume of cells in a cell population.

According to another aspect, the present invention provides a method for inhibiting growth of a neoplasm, the method comprising the steps: (a) providing a therapeutically effective amount of a kinase inhibiting composition to a subject in need thereof, wherein the kinase inhibiting composition comprises an inhibitory amount of an isolated nucleic acid that encodes a polypeptide having 100% amino acid sequence identity to a KIP peptide, wherein the polypeptide inhibits kinase activity of a kinase enzyme; (b) contacting the neoplasm with the kinase inhibiting composition of step (a) such that the isolated nucleic acid associates with the neoplasm; and (c) inhibiting the growth of the neoplasm. In another embodiment, the isolated nucleic acid of step (a) further comprises a controllable regulatory element.

According to another aspect, the present invention provides a method for inhibiting growth of a neoplasm, the method comprising the steps: (a) providing a therapeutically effective amount of a kinase inhibiting composition to a subject in need thereof, wherein the kinase inhibiting composition comprises an inhibitory amount of a kinase inhibiting peptide, wherein the kinase inhibiting peptide comprises a KIP peptide, (b) contacting the neoplasm with the kinase inhibiting composition such that the kinase inhibiting peptide associates with the neoplasm; and (c) inhibiting the growth of the neoplasm. In some such embodiments, the kinase inhibiting peptide of step (a) is operably linked to a controllable regulatory element.

According to another embodiment, the neoplasm is a benign tumor. According to another embodiment, the neoplasm is a malignant tumor. According to another embodiment, the neoplasm is a neoplasm selected from the group consisting of: a papilloma, an adenoma, a hydatidiform mole, a fibroma, a chondroma, an osteoma, a leiomyoma, a rhabdomyoma, a lipoma, a hemangioma, a lymphangioma, a polycythemia vera, an infectious mononucleosis, a "benign" glioma, a meningioma, a ganglioneuroma, a neurilemmoma, a neurofibroma, a pigmented nevus (mole), a pheochromocytoma, a carcinoid tumors, a teratoma, a carcinoma, an adenocarcinoma, a basal cell carcinoma, a choriocarcinoma, a fibrosarcoma, a chondrosarcoma, an osteosarcoma, a leiomyosarcoma, a rhabdomyosarcoma, a liposarcoma, a hemangiosarcoma, a lymphangiosarcoma, a myelocytic leukemia, an erythrocytic leukemia, a lymphocytic leukemia, a multiple myeloma, a monocytic leukemia, an Ewing's sarcoma, a non-Hodgkin's malignant lymphoma, a medulloblastoma, an oligodendroglioma, a neurilemmal sarcoma malignant melanoma, thymoma, a glioblastoma multiforme, an astrocytoma, an ependymoma, an meningeal sarcoma, a neuroblastoma (schwannoma), a neurofibrosarcoma, a malignant pheochromocytoma, a retinoblastoma, a carcinoid tumor, a nephroblastoma (Wilms' tumor), a teratocarcinoma and an embryonal carcinoma with choriocarcinoma.

According to another embodiment, the isolated nucleic acid that encodes a polypeptide having 100% amino acid sequence identity to a KIP peptide, wherein the polypeptide inhibits kinase activity, may be administered locally or systemically.

According to another aspect, the present invention further describes experiments in animal models of human disease that will be used to determine the effect of the polypeptides of the present invention. These animal models have been used by other investigators, and are generally accepted as such. The therapeutic results obtained with this model therefore can be extrapolated to methods of treating human subjects.

Model of Hyperplasia

A KIP peptide may be evaluated for its ability to reduce hyperplasia using a porcine model of coronary restenosis as described by Heldman et al. (A. W. Heldman, L. Cheng, G. M. Jenkins, etc., 2001, "Paclitaxel Stent Coating Inhibits Neointimal Hyperplasia at 4 Weeks in a Porcine Model of Coronary Restenosis," *Circulation*, 103: 2289-2295). Stents are coated by dipping the stent into a solution containing a KIP peptide and drying the solvent. The coated stents is mounted on balloon catheters and sterilized using ethylene oxide gas. Male and female NIH minipigs weighing 35 to 45 kg are pretreated with aspirin (325 mg) and diltiazem (180 mg) the day before stent implantation. After sedating the animals with ketamine (20 mg/kg IM) and acetylpromazine (0.22 mg/kg IM) and giving the animas sodium pentobarbital (4 mg/kg IV) to facilitate supine positioning and endotracheal intubation, an arterial sheath is inserted into the right carotid artery under sterile surgical technique. After administering heparin (5000 U), the stent may be delivered to the left anterior descending coronary artery through a guiding catheter and deployed using balloon inflations. Angiograms are performed throughout the recovery and experimental period. The extent of hyperplasia may be evaluated inter alia using histological preparation and histomorphometric analysis.

Model of Neoplasm

A KIP peptide may be evaluated for its ability of a KIP peptide to inhibit or decrease the growth of a neoplasm using a scid mouse tumor model, such as that described by Becker et al. (J. C. Becker, N. Varki, S. D. Gillies, K. Furukawa, and R. A. Reisfeld, 1996, "Long-lived and Transferable Tumor Immunity in Mice after Targeted Interleukin-2 Therapy," J. Clin. Invest., 98(12): 2801-2804). Subcutaneous tumors may be induced by subcutaneous injection of $5 \times 10^6$ tumor cells (such as the murine melanoma cell line B16 or the cell line B78-D14) suspended in an isotonic buffer, such as RPMI 1640. Within 14 days, tumors of volume around 40 μl should be present. The KIP peptide may be injected directly into the tumor mass, administered at the time of tumor induction via injection, or delivered via a vehicle or a device. The subcutaneous tumors may be evaluated, inter allia, via histology, immunohistochemistry, or imaging techniques to evaluate the efficacy of the KIP peptide in inhibiting, slowing, decreasing, or modifying the growth or size of the neoplasm.

Cell Death

The term "programmed cell death" (or "PCD") as used herein refers to death of a cell in any form, mediated by an intracellular program. In contrast to necrosis (a form of cell-death that results from acute tissue injury and provokes an inflammatory response), PCD is a regulated process that generally confers advantage during the life cycle of an organism. Two types of PCD are known: apotosis (Type I) and autophagic (Type II) cell death. Other pathways of cell death include non-apoptotic programmed cell death (also referred to as caspase-independent PCD or necrosis-like PCD), anolkis (a form of apoptosis induced by anchorage-dependent cells detaching from the surrounding extracellular matrix), cornification, excitotoxicity, and Wallerain degeneration (axonal degeneration).

The term "apoptosis" as used herein refers to a series of biochemical events that lead to morphological changes including, for example, but not limited to, blebbing, changes to the cell membrane, such as loss of membrane asymmetry and attachment, cell shrinkage, nuclear fragmentation, chromatin condensation, and chromosomal DNA fragmentation. The process of apoptosis is controlled by a diverse range of extracellular and intracellular cell signals. Such extracellular signals may include, for example, but are not limited to, toxins, hormones, growth factors, nitric oxide or cytokines, and therefore must either cross the plasma membrane or transduce the cell to effect a response. The term "intracellular apoptotic signaling" as used herein refers to a response initiated by a cell in response to stress. It ultimately may result in cell suicide. The binding of nuclear receptors by factors, such as, glucocorticoids, heat, radiation, nutrient deprivation, viral infection, and hypoxia may lead to the release of intracellular apoptotic signals by a damaged cell.

According to another aspect, the present invention provides a method for inducing programmed cell death in a cell population, the method comprising the steps: (a) providing a therapeutically effective amount of a kinase inhibiting composition, wherein the kinase inhibiting composition comprises an inhibitory amount of a kinase inhibiting peptide; (b) contacting at least one cell in the cell population with the kinase inhibiting composition such that the kinase inhibiting peptide associates with the at least one cell; and (c) inducing programmed cell death of the at least one cell in the cell population. In some such embodiments, the cell is a prokaryotic cell. In some such embodiments, the cell is a eukaryotic cell. In some such embodiments, the cell is a mammalian cell. In some such embodiments, the mammalian cell is selected from the group consisting of a neuron, an epithelial cell, a muscle cell, a blood cell, an immune cell, a stem cell, an osteocyte, or an endothelial cell. In some such embodiments, the programmed cell death is apoptosis.

According to another embodiment, the present invention provides a method for inducing programmed cell death in a cell population, the method comprising the steps: (a) providing a therapeutically effective amount of a kinase inhibiting composition, wherein the kinase inhibiting composition comprises an inhibitory amount of an isolated nucleic acid that encodes a polypeptide having 100% amino acid sequence identity to a KIP peptide, wherein the polypeptide inhibits kinase activity of a kinase enzyme; (b) contacting at least one cell in the cell population with the kinase inhibiting composition of step (a) such that the isolated nucleic acid associates with the at least one cell; and (c) inducing programmed cell death of the at least one cell in the cell population. In some such embodiments, the isolated nucleic acid of step (a) further comprises a controllable regulatory element. In some such embodiments, the cell is a prokaryotic cell. In some such embodiments, the cell is a mammalian cell. In some such embodiments, the mammalian cell is selected from the group consisting of a neuron, an epithelial cell, a muscle cell, a blood cell, an immune cell, a stem cell, an osteocyte, or an endothelial cell. In some such embodiments, the cell is a eukaryotic cell. In some such embodiments, the programmed cell death is apoptosis.

The term "progressive disease" as used herein implies that the previously administered treatment(s) are/were not effective and other treatments may be necessary to control the disease. The term "stable disease" as used herein refers to no significant decrease in the size or number of lesions in the body, and implies further treatment(s) probably will be needed to attempt a cure. The term "partial response" as used herein refers to a reduction of disease by about 30% or more as identified in clinical examination, X-ray, scans, or tests for biomarkers. The term "complete response" as used herein refers to no residual disease that can be identified in clinical examination, by X-ray, or in tests for biomarkers of the disease; cure is not implied.

According to another aspect, the present invention provides a method for inhibiting the progression of a proliferating cell population, the method comprising the steps of: (a) providing a therapeutically effective amount of a kinase inhibiting composition, wherein the kinase inhibiting composition comprises an inhibitory amount of a kinase inhibiting peptide (b) contacting at least one cell in the proliferating cell population with the kinase inhibiting composition such that the kinase inhibiting peptide associates with the proliferating at least one cell; and (c) inhibiting proliferation by the at least one cell. In some such embodiments, the kinase inhibiting peptide is operably linked to a controllable regulatory element. In some such embodiments, the cell is a prokaryotic cell. In some such embodiments, the cell is a eukaryotic cell.

According to one embodiment, the present invention provides a method for inhibiting the progression of a proliferating cell population, the method comprising the steps of: (a) providing a therapeutically effective amount of a kinase inhibiting composition, wherein the kinase inhibiting composition comprises an inhibitory amount of a kinase inhibiting peptide, wherein the kinase inhibiting peptide comprises a KIP peptide, (b) contacting at least one cell in the proliferating cell population with the kinase inhibiting composition such that the kinase inhibiting peptide associates with the proliferating at least one cell; and (c) inhibiting proliferation by the at least one cell. In some such embodiments, the cell is a prokaryotic cell. In some such embodiments, the cell is a eukaryotic cell.

According to another embodiment, the present invention provides a method for inhibiting the progression of a proliferating cell population, the method comprising the steps: (a) providing a therapeutically effective amount of a kinase inhibiting composition, wherein the kinase inhibiting composition comprises an inhibitory amount of an isolated nucleic acid that encodes a polypeptide having 100% amino acid sequence identity to a KIP peptide, wherein the polypeptide inhibits kinase activity of a kinase enzyme; (b) contacting at least one cell in the proliferating cell population with the kinase inhibiting composition of step (a) such that the isolated nucleic acid associates with the proliferating at least one cell; and (c) inhibiting proliferation of the at least one cell. In another embodiment, the isolated nucleic acid of step (a) further comprises a controllable regulatory element. In some such embodiments, the cell is a prokaryotic cell. In some such embodiments, the cell is a eukaryotic cell.

According to another embodiment, the kinase inhibiting composition, wherein it is desirable to deliver them locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions (i.e., kinase inhibiting compositions) also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The kinase inhibiting composition, and optionally other therapeutics, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a kinase inhibiting composition, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations are also prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(l-glutamic acid), poly-(l-glutamic acid), poly-(d-aspartic acid), poly-(l-aspartic acid), poly-(l-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited to, the hydroxyl off carbon 3 and/or the hydroxyl off carbon 7.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

In some embodiments, the kinase inhibiting composition is a pharmaceutical composition. The pharmaceutical compositions described within the present invention contain a therapeutically effective amount of a kinase inhibiting composition and optionally other therapeutic agents included in a pharmaceutically-acceptable carrier. The term "pharmaceutically-acceptable carrier" as used herein refers to one or more compatible solid or liquid filler, diluents or encapsulating substances which are suitable for administration to a human or other vertebrate animal. The term "carrier" as used herein refers to an organic or inorganic ingredient, natural or synthetic, with which the active ingredient is combined to facilitate the application. The active ingredient may be a kinase inhibiting composition. The components of the pharmaceutical compositions also are capable of being commingled in a manner such that there is no interaction which would substantially impair the desired pharmaceutical efficiency.

The therapeutic agent(s), including the kinase inhibiting composition, may be provided in particles. The term "particles" as used herein refers to nano or microparticles (or in some instances larger) that may contain in whole or in part the kinase inhibiting composition. The particles may contain the therapeutic agent(s) in a core surrounded by a coating. The therapeutic agent(s) also may be dispersed throughout the particles. The therapeutic agent(s) also may be adsorbed on at least one surface of the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the kinase inhibiting composition in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

In another aspect, the present invention further provides a biomedical device comprising at least one isolated kinase inhibiting peptide comprising a sequence according to Formula IV, wherein the one or more isolated kinase inhibiting peptides are disposed on or in the device. In some such embodiments, the at least one kinase inhibiting peptide is at least one peptide having an amino acid sequence selected from the group consisting of HRRIKAWLKKILALARQLGVAA [SEQ ID NO: 192]; WLRRIKAWLRRIKALARQLGVAA [SEQ ID NO: 113]; and WLRRIKAWLRRALARQLGVA [SEQ ID NO: 177]. In some such embodiments, the biomedical device comprises at least one isolated kinase inhibiting peptides comprising a sequence according to Formula V, wherein the one or more isolated kinase inhibiting peptides are disposed on or in the device. In some such embodiments, the biomedical device comprises at least one isolated kinase inhibiting peptide comprising a sequence according to Formula VI, wherein the one or more isolated kinase inhibiting peptides are disposed on or in the device. In some such embodiments, the kinase inhibiting peptide is a peptide having an amino acid sequence selected from the group consisting of

```
KAFAKLAARLYRKALARQLGVAA;      [SEQ ID NO: 173]

FAKLAARLYRKALARQLGVAA;        [SEQ ID NO: 163]
and

WLRRIKAWLRRIKALNRQLGVAA.      [SEQ ID NO: 142]
```

General methods in molecular genetics and genetic engineering useful in the present invention are described in the current editions of *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), and *Gene Transfer and Expression Protocols*, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include plural references unless the context clearly dictates otherwise. All technical and scientific terms used herein have the same meaning.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Comparison of the Effectiveness of a Peptide Inhibitor of MAPKAP kinase II (MK2) Alone or Covalently Bound to the WLRRIKAWLRRIKA [SEQ ID NO: 134] Transduction Domain Using the Omnia™ Lysate Assay for MAPKAP-K2 kit (Invitrogen, Carlsbad, Calif.), the reaction velocity for MK2 was determined in the presence and absence of each of the peptides listed in Table 2. Briefly, inhibitor peptide concentrations at 12.5 μmol, 25 μmol, 50 μmol and 100 μmol were evaluated. The kit contains a proprietary reaction buffer to which the following are added (final concentrations are given): 1 mM ATP, 0.2 mM DTT, 10 μM MAPKAP-K2 Sox-modified peptide substrate, 5 ng MK2, and the peptide inhibitor of interest (final volume of 50 μL). The reactions were performed in the wells of a low protein-binding 96-well plate provided with the kit, and fluorescence readings at 485 nm were taken every 30 seconds for 20 minutes in a Molecular Devices M5 Spectrophotometer. A peptide having the sequence KALNRQLGVAA [SEQ ID NO: 124] was used as a baseline because it is a known inhibitor based on the work of Hayess and Benndorf (Katrin Hayess and Rainer Benndorf, 1997, "Effect of protein kinase inhibitors on activity of mammalian small heat-shock protein (HSP25) kinase", *Biochemical Pharmacology*, 53(9): 1239-1247.

The reaction velocities for a MK2 inhibitor concentration of 100 μM are shown in Table 3; relative reaction velocities between peptides were similar at lower and higher concentrations (data not shown). The results of this study show that several of the kinase inhibiting peptides according to the present invention were able to inhibit MK2 activity. The results further provide information as to the amino acids that are most crucial for the function of the MK2 inhibitor. Note that the covalent attachment of the MK2 inhibitor peptide to the WLRRIKAWLRRIKA [SEQ ID NO: 134] transduction domain substantially increases the MK2 inhibitor function.

TABLE 2

MK2 Inhibitor Sequence Evaluation of Each Amino Acid

|  | [SEQ ID NO:] |
|---|---|
| Controls | |
| KALNRQLGVA* | [SEQ ID NO: 114] |
| KKKALNRQLGVAA# | [SEQ ID NO: 115] |
| (WLRRIKA)₂LNRQLGVAA | [SEQ ID NO: 178] |
| Alanine Scan | |
| KALNRQLGVAA | [SEQ ID NO: 116] |
| KAANRQLGVAA | [SEQ ID NO: 117] |
| KALARQLGVAA | [SEQ ID NO: 118] |
| KALNAQLGVAA | [SEQ ID NO: 119] |
| KALNRALGVAA | [SEQ ID NO: 120] |
| KALNRQAGVAA | [SEQ ID NO: 121] |
| KALNRQLAVAA | [SEQ ID NO: 122] |
| KALNRQLGAAA | [SEQ ID NO: 123] |
| d-Amino Acid Scan | |
| KdALNRQLGVAA | [SEQ ID NO: 179] |
| KAdLNRQLGVAA | [SEQ ID NO: 180] |
| KALdNRQLGVAA | [SEQ ID NO: 181] |
| KALNdRQLGVAA | [SEQ ID NO: 182] |
| Controls | |
| KALNRdQLGVAA | [SEQ ID NO: 183] |
| KALNRQdLGdVAA | [SEQ ID NO: 184] |
| KALNRQLGdVAA | [SEQ ID NO: 185] |

*= Control to determine the requirement of the final A;
=Control to determine the importance of initial Ks

TABLE 3

Reaction Velocities for MK2 Inhibitor Variants (n = 3)

| MK2 Inhibitor Variant Peptide Sequence | % of KALNRQLGVAA [SEQ ID NO: 124] Reaction Velocity at an Inhibitor Concentration of 100 μM (+/-Peptide Sequence SEM*) |
|---|---|
| WLKKIKAWLKKIKALNRQLGVVA [SEQ ID NO: 159] | -32% (+/-6%) |
| KALNRQLGVAA [SEQ ID NO: 124] | 100% (+/-3%) |
| KALNRQLGVA [SEQ ID NO: 125] | 100% (+/-3%) |
| KAANRQLGVAA [SEQ ID NO: 126] | 152% (+/-3%) |
| KALARQLGVAA [SEQ ID NO: 127] | 39% (+/-1%) |

TABLE 3-continued

Reaction Velocities for MK2 Inhibitor Variants (n = 3)

| MK2 Inhibitor Variant Peptide Sequence | % of KALNRQLGVAA [SEQ ID NO: 124] Reaction Velocity at an Inhibitor Concentration of 100 μM (+/-Peptide Sequence SEM*) |
|---|---|
| KALNAQLGVAA [SEQ ID NO: 128] | 358% (+/-8%) |
| KALNRALGVAA [SEQ ID NO: 129] | 358% (+/-15%) |
| KALNRQAGVAA [SEQ ID NO: 130] | 118% (+/-4%) |
| KALNRQLAVAA [SEQ ID NO: 131] | 72% (+/-3%) |
| KALNRQLGAAA [SEQ ID NO: 132] | 373% (+/-13%) |
| KAdLNRQLGVAA [SEQ ID NO: 180] | 146% (+/-4%) |
| KALdNRQLGVAA [SEQ ID NO: 181] | 95% (+/-6%) |
| KALNdRQLGVAA [SEQ ID NO: 182] | 306% (+/-4%) |
| KALNRdQLGVAA [SEQ ID NO: 187] | 276% (+/-3%) |
| KALNRQdLGVAA [SEQ ID NO: 188] | 357% (+/-10%) |
| KALNRQLGdVAA [SEQ ID NO: 185] | 260% (+/-14%) |
| KKKALNRQLGVAA [SEQ ID NO: 133] | 91% (+/-4%) |

*SEM = Standard Error of the Mean for three values

Example 2

Transduction Domain Reaction Velocities

The MK2 inhibition activity of WLRRIKAWLRRIKA [SEQ ID NO: 134] transduction domain was compared with the MK2 inhibition activity of other known transduction domains—YARAAARQARA [SEQ ID NO: 135] and YGRKKRRQRRR [SEQ ID NO: 190]. The transduction domains were tested for MK2 activity using the same assay conditions as Example 1. The results are shown in Table 4.

TABLE 4

Reaction Velocities for Different Transduction Domains (n = 3)

| Peptide Sequence | [SEQ ID NO:] | % of KKKALNRQLGVAA [SEQ ID NO: 115] Reaction Velocity at an Inhibitor Concentration of 100 μM (+/-SEM*) |
|---|---|---|
| WLRRIKA | 137 | 394% (+/-5%) |
| WLRRIKAWLRRIKA | 134 | 19% (+/-2%) |

TABLE 4-continued

Reaction Velocities for Different Transduction Domains (n = 3)

| Peptide Sequence | [SEQ ID NO:] | % of KKKALNRQLGVAA [SEQ ID NO: 115] Reaction Velocity at an Inhibitor Concentration of 100 μM (+/-SEM*) |
|---|---|---|
| YARAAARQARA | 135 | 274% (+/-9%) |
| YGRKKRRQRRR | 136 | 158% (+/-11%) |

*SEM = Standard Error of the Mean for three values

These results indicate substantial differences in the effect of several transduction domains on inhibiting MK2 and that transduction domains are useful to inhibit the activity of kinases, such as MK2. The WLRRIKA [SEQ ID NO: 137] monomer had the same level of inhibition as the no inhibitor control (data not shown); however, the WLRRIKAWLRRIKA [SEQ ID NO: 134] transduction domain dimer inhibited MK2 significantly more than KKKALNRQLGVAA [SEQ ID NO: 115]. YARAAARQARA [SEQ ID NO: 135] and YGRKKRRQRRR [SEQ ID NO: 136] also inhibit MK2 but not nearly as much as WLRRIKAWLRRIKA [SEQ ID NO: 134].

Example 3

MK2 Inhibitor Peptides with Transduction Domains

A set of MK2 inhibitor peptides having transduction domains was synthesized (see Table 5). Variants included peptides with the WLRRIKAWLRRIKA [SEQ ID NO: 134] transduction domain and alanine substituted for asparagine, alanine substituted for glycine, or both alanine substitutions in the therapeutic domain. The same peptides with the YARAAARQARA [SEQ ID NO: 135] transduction domain also were prepared. The reaction velocities of these variants were compared to the reaction velocity of a blank with no inhibitor added. Results are shown in Table 6. The data in Table 6 shows a synergy between the transduction domain and the therapeutic domain in inhibiting MK2. Since the WLRRIKAWLRRIKA [SEQ ID NO: 134] transduction domain is a much stronger inhibitor of MK2 than the YARAAARQARA [SEQ ID NO: 135] transduction domain, peptides with a WLRRIKAWLRRIKA [SEQ ID NO: 134] transduction domain are much stronger inhibitors of MK2 at a given concentration than are peptides with the YARAAARQARA [SEQ ID NO: 135] transduction domain.

TABLE 5

Proposed Optimized Therapeutic Domains with Two Different Transduction Domains

| Peptides with WLRRIKAWLRRIKA [SEQ ID NO: 134] Transduction Domain | SEQ ID NO: | Peptides with YARAAARQARA [SEQ ID NO: 135] Transduction Domain | SEQ ID NO: |
|---|---|---|---|
| WLRRIKAWLRRIKALARQLAVA | 138 | YARAAARQARAKALARQLAVA | 143 |
| WLRRIKAWLRRIKALARQLGVA | 139 | YARAAARQARAKALARQLGVA | 144 |
| WLRRIKAWLRRIKALARQLAVA | 191 | YARAAARQARAKALNRQLAVA | 145 |

TABLE 5-continued

Proposed Optimized Therapeutic Domains with
Two Different Transduction Domains

| Peptides with WLRRIKAWLRRIKA [SEQ ID NO: 134] Transduction Domain | SEQ ID NO: | Peptides with YARAAARQARA [SEQ ID NO: 135] Transduction Domain | SEQ ID NO: |
|---|---|---|---|
| WLRRIKAWLRRIKALNRQLGVA | 141 | YARAAARQARAKALNRQLGVA | 146 |
| WLRRIKAWLRRIKALNRQLGVA A | 142 | YARAAARQARAKALNRQLGVA A | 147 |

TABLE 6

Reaction Velocities for Selected Optimized Peptides (n = 3)

| Peptide Sequence | SEQ ID NO of Peptide Sequence | % of Blank Reaction Velocity at an Inhibi-SEQtor Concentration 6.25pN (+/-SEM*) |
|---|---|---|
| WLRRIKAWLRRIKALARQLAVA | 138 | 3.3% (+/-0.4%) |
| WLRRIKAWLRRIKALARQLGVA | 139 | 3.9% (+/-0.8%) |
| WLRRIKAWLRRIKALNRQLAVA | 140 | -2.1% (+/-0.5%) |
| WLRRIKAWLRRIKKKALARQLAVA | 148 | 1.0% (+/-0.4%) |
| YARAAARQARAKALARQLGVA | 144 | 28.9% (+/-0.8%) |
| YARAAARQARAKKKALARQLAVA | 112 | 22.4% (+/-0.50%) |
| No Inhibitor Added | — | 100% (+/-2%) |

*SEM = Standard Error of the Mean or three values

Example 4

Kinase Profiler Assays

KIP peptides WLRRIKAWLRRIKALNRQLGVAA [SEQ ID NO: 142], KAFAKLAARLYRKALARQLGVAA [SEQ ID NO: 173], and FAKLAARLYRKALARQLGVAA [SEQ ID NO: 163] were utilized to profile a variety of different kinases. The kinase profiler assay services provided by Upstate, a part of Millipore Corporation (Billerica, Mass.), were utilized to conduct the kinase profiles. The kinase profiler assays, which are radiometric, are based on measuring the amount of radioactive transfer from an ATP (y-$^{33}$P-ATP) to a substrate peptide using known concentrations of kinase enzyme, inhibitor, ATP, and buffer at defined time points and temperatures. Details on the reaction conditions for each kinase are available at www.millipore.com/drugdiscovery/dd3/KinaseProfiler. For example, the inhibition of ROCK-1 (h) was tested using a buffer containing 20 mM MOPS, 1 mM EDTA, 0.01% Brij-35, 5% Glycerol, 0.1% P-mercaptoethanol, 1 mg/mL BSA. ROCK-1(h) (5-10 mU) was incubated with 8 mM MOPS pH 7.0, 0.2 mM EDTA, 30 i.IM of the peptide KEAKEKRQEQIAKRRRLSSLRASTSKSGGSQK [SEQ ID NO: 189], 10 mM Mg acetate and y-$^{33}$P-ATP (specific activity approximately 500 cpm/pmol, concentration as required) in a final reaction volume of 25 pl. The reaction was initiated by the addition of the MgATP mixture in the absence and presence of inhibitor compounds. After incubation for 40 minutes at room temperature, the reaction was stopped by the addition of 5) 11 of a 3% phosphoric acid solution. 10 pl of the reaction mixture then was spotted onto a P30 filtermat. The filtermat was washed three times for 5 minutes in 75 mM phosphoric acid, once in methanol, dried and counted by scintillation counting. Where the kinase is uninhibited, the kinase phosphorylates a positively charged substrate with radioactive ATP, which then binds to a negatively charged filter membrane. Scintillation counts (radioactivity) directly correlate with kinase activity. The assay was run at an ATP concentration within 15 micromolar of the $K_m$ for each individual kinase. All profile data less than 100 indicate kinase inhibition while data greater than 100 indicate kinase stimulation.

The results of the kinase profiler assay are shown in Table 7 for WLRRIKAWLRRIKALNRQLGVAA [SEQ ID NO: 142]; in Table 8 for KAFAKLAARLYRKALARQLGVAA [SEQ ID NO: 173]; and in Table 9 for FAKLAARLYRKALARQLGVAA [SEQ ID NO: 163]. The results show that KIP peptides are useful in regulating kinase function. More specifically, these data show that WLRRIKAWLRRIKALNRQLGVAA [SEQ ID NO: 142], KAFAKLAARLYRKALARQLGVAA [SEQ ID NO: 173], and FAKLAARLYRKALARQLGVAA [SEQ ID NO: 163] peptides inhibit several kinases, many of which are known to be important mediators of hyperplasia and cancer.

TABLE 7

Results of the kinase profiler assay using test peptide WLRRIKAWLRRIKALNRQLGVAA [SEQ ID NO: 142].

| Kinase | Profile-1 @ = 30 μm |
|---|---|
| Abl (h) | 24 |
| AMPK (r) | 36 |
| Aurora-A (h) | 46 |
| BTK (h) | 5 |
| CaMKI (h) | 9 |
| CDKI/cyclinB (h) | 17 |
| CHK1 (h) | 31 |
| CKIB (h) | 52 |
| CK2 (h) | 114 |
| cKit (h) | 23 |
| DYRK2 (h) | 93 |
| EGFR (h) | 10 |
| EphA2 (h) | 38 |
| FGFR1 (h) | 27 |
| Flt3 (h) | 38 |
| GSK3β (h) | 129 |
| IGF-IR (h) | 227 |
| IRAK4 (h) | 12 |
| JAK3 (h) | 85 |
| KDR (tl) | 27 |
| Lck (h) | 130 |

TABLE 7-continued

Results of the kinase profiler assay using test peptide WLRRIKAWLRRIKALNRQLGVAA [SEQ ID NO: 142].

| Kinase | Profile-1 @ = 30 µm |
|---|---|
| L1MK1 (h) | 89 |
| MAPKI (h) | 121 |
| MEKI (h) | 14 |
| Met (h) | 30 |
| MLCK (h) | 4 |
| PDGFRB (h) | 42 |
| PhKγ2 (h) | 15 |
| Pim-1 (h) | 5 |
| PKA (h) | 80 |
| PKB β (h) | 18 |
| PKC β 1 (h) | 8 |
| PKCδ (h) | 11 |
| PKG1α (h) | 16 |
| PKG1β (h) | 15 |
| Ret (h) | 117 |
| ROCK-1 (h) | 0 |
| Rsk2 (h) | 14 |
| SAPK2 a (h) | 61 |
| Src(1-530) (h) | 6 |
| Syk (h) | 19 |
| Tie2 (h) | 17 |
| TrkA (h) | 6 |

TABLE 8

Results of the kinase profiler assay using test peptide KAFAKLAARLYRKALARQLGVAA [SEQ ID NO: 173]

| Kinase | Profile-1 @ = 100 µm |
|---|---|
| Abl (h) | 55 |
| AMPK (r) | 118 |
| ASK1 (h) | 48 |
| Aurora-A (h) | 60 |
| BTK (h) | 16 |
| CaMKI (h) | 0 |
| CDKI/cyclinB (h) | 55 |
| CHK1 (h) | 68 |
| CKIB (h) | 97 |
| CK2 (h) | 79 |
| cKit (h) | 31 |
| DYRK2 (h) | −10 |
| EGFR (h) | 16 |
| EphA2 (h) | 22 |
| FGFR1 (h) | 35 |
| Flt3 (h) | 20 |
| GSK3β (h) | 184 |
| IGF-IR (h) | 76 |
| IRAK4 (h) | 16 |
| JAK3 (h) | 91 |
| JNK1α1 (h) | 92 |
| KDR (tl) | 56 |
| Lck (h) | 847 |
| L1MK1 (h) | 93 |
| MAPKI (h) | 108 |
| MAPKAP-K2 (h) | 8 |
| MAPKAP-K3 (h) | 17 |
| MEKI (h) | 66 |
| Met (h) | 22 |
| MKK4 (m) | 114 |
| MKK6 (h) | 48 |
| MLCK (h) | 2 |
| MSK1 (h) | 13 |
| MSK2 (h) | 30 |
| PDGFRβ (h) | 66 |
| PhKγ2 (h) | 27 |
| Pim-1 (h) | 1 |
| PKA (h) | 103 |
| PKB β (h) | 28 |
| PKC β 1 (h) | 23 |
| PKCδ (h) | 24 |
| PKG1α (h) | 25 |
| PKG1β (h) | 24 |
| PRAK | 148 |
| Ret (h) | 117 |

TABLE 8-continued

Results of the kinase profiler assay using test peptide KAFAKLAARLYRKALARQLGVAA [SEQ ID NO: 173]

| Kinase | Profile-1 @ = 100 μm |
|---|---|
| ROCK-1 (h) | 29 |
| Rsk2 (h) | 6 |
| SAPK2 a (h) | 59 |
| Src(1-530) (h) | 3 |
| Syk (h) | 4 |
| Tie2 (h) | 8 |
| TrkA (h) | 16 |

TABLE 9

Results of the kinase profiler assay using test peptide FAKLAARLYRKALARQLGVAA [SEQ ID NO: 163].

| Kinase | Profile-1 @ = 100 μm |
|---|---|
| Abl (h) | 41 |
| AMPK (r) | 101 |
| ASK1 (h) | 53 |
| Aurora-A (h) | 65 |
| BTK (h) | 19 |
| CaMKI (h) | 0 |
| CDKI/cyclinB (h) | 36 |
| CHK1 (h) | 54 |
| CKIB (h) | 99 |
| CK2 (h) | 80 |
| cKit (h) | 42 |
| DYRK2 (h) | -11 |
| EGFR (h) | 18 |
| EphA2 (h) | 32 |
| FGFR1 (h) | 22 |
| Flt3 (h) | 14 |
| GSK3β (h) | 188 |
| IGF-IR (h) | 69 |
| IRAK4 (h) | 13 |
| JAK3 (h) | 102 |
| JNK1α1 (h) | 91 |
| KDR (tl) | 78 |
| Lck (h) | 493 |
| L1MK1 (h) | 92 |

TABLE 9-continued

Results of the kinase profiler assay using test peptide FAKLAARLYRKALARQLGVAA [SEQ ID NO: 163].

| Kinase | Profile-1 @ = 100 μm |
|---|---|
| MAPKI (h) | 104 |
| MAPKAP-K2 (h) | 5 |
| MAPKAP-K3 (h) | 10 |
| MEKI (h) | 68 |
| Met (h) | 17 |
| MKK4 (m) | 90 |
| MKK6 (h) | 42 |
| MLCK (h) | 1 |
| MSK1 (h) | 11 |
| MSK2 (h) | 24 |
| PDGFRβ (h) | 92 |
| PhKγ2 (h) | 20 |
| Pim-1 (h) | 1 |
| PKA (h) | 76 |
| PKB β (h) | 16 |
| PKC β 1 (h) | 73 |
| PKCδ (h) | 40 |
| PKG1α (h) | 12 |
| PKG1β (h) | 15 |
| PRAK | 131 |
| Ret (h) | 89 |
| ROCK-1 (h) | 25 |
| Rsk2 (h) | -1 |
| SAPK2 a (h) | 30 |
| Src(1-530) (h) | 5 |
| Syk (h) | 38 |
| Tie2 (h) | 0 |
| TrkA (h) | 17 |

Example 5

Toxicity Testing of KIP Peptides on Multiple Cancer Cell Lines

The effect of six concentrations of four KIP peptides on seven cancer cell lines was evaluated. The KIP peptides used in these experiments are listed in Table 10.

TABLE 10

KIP Peptides tested on cancer cell lines

| Peptide Number | Peptide Primary Structure | SEQ ID NO: |
|---|---|---|
| 1 | HRRIKAWLKKIKALARQLGVAA | 166 |
| 2 | WLRRIKAHRRIKALARQLGVAA | 167 |
| 3 | WLRRIKAWLRR | 168 |
| 4 | WLRRIKAWLRRALNRQLGVAA | 169 |

The seven cell lines were: estrogen dependent MCF-7 breast cancer cells, non estrogen dependent MDA 231 breast cancer cells, SF 539 central nervous system cancer cells, HT29 colon cancer cells, Paca 2 pancreatic cancer cells, PC3 prostate cancer cells, and A549 lung cancer cells. For each cell line, exponentially growing cells were trypsinized and seeded into individual wells of a 96-well plate. Cells were maintained in a humidified, 5% $CO_2$ incubator at 37° C. for 24 hours. The next day, fresh media was added along with 1 µl of a stock solution of peptide to give final peptide concentrations of 0.3 µM, 1 µM, 3 µM, 10 µM, 30 µM, and 100 µM (n=4). Doxorubicin was tested as a positive control. After incubating the cells for 72 hours, to each well was added 20 µl of 0.5% MTT {3-(4,5-dimethyldiazol-2-yl)-2,5 diphenyl tetrazolium bromide} solution. The plates then were incubated for an additional 4 hours, at which time the absorbance at 570 nm was measured for each well using a microplate reader. The absorbance was plotted as function of peptide concentration, and IC50 values were calculated for each peptide for each cell line. The results from this experiment are presented in FIGS. 1-7. Calculated IC50 values are presented in Table 11. For all cell lines, the IC50 values for each of the four peptides was below 50 µM. These results indicate that KIP peptides are antiproliferative/cytotoxic to several different cancer cell lines in a dose dependent manner.

TABLE 11

IC50 for KIP peptides tested on cancer cell lines

| | Cell Line IC50 (µM) | | | | | | |
|---|---|---|---|---|---|---|---|
| Peptide | MCF-7 | MDA 231 | SF 539 | HT29 | Paca 2 | A549 | PC3 |
| Peptide 1 | 1.6 | 9.3 | 4.3 | 6.7 | 9.0 | 8.7 | 6.0 |
| Peptide 2 | 7.8 | 19.9 | 26.0 | 26.4 | 19.5 | 31.9 | 28.9 |
| Peptide 3 | 13.5 | 17.4 | 22.0 | 20.7 | 42.5 | 34.3 | 35.5 |
| Peptide 4 | 4.4 | 12.0 | 10.0 | 11.8 | 11.2 | 12.5 | 23.7 |

Example 6

Evaluation of Apoptosis in MCF-7 Breast Cancer Cells Using a KIP Peptide

MCF-7 breast cancer cells were seeded in individual wells of a 96-well plate and were maintained for 24 hours in a humidified, 5% CO2 incubator at 37° C. The next day, fresh media was added along with 1 µl of a stock solution of KIP peptide HRRIKAWLKKIKALARQLGVAA [SEQ ID NO: 166] to give a final concentration of 3 µM or 10 µM (n=4). After incubating the cells for 24 hours, cells were treated with Hoescht dye for nuclear staining, propidium iodide to stain for DNA from necrotic cells, and Annexin V to visualize apoptotic cells.

Figure 8:
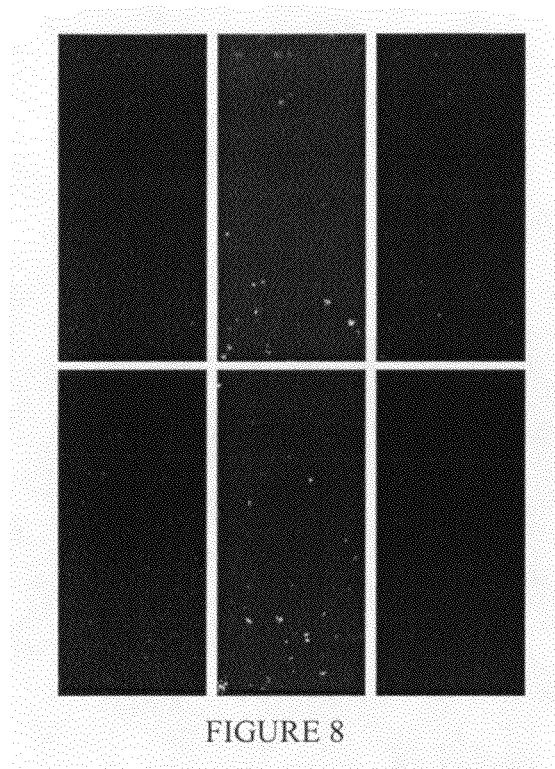
FIG. 8 shows that KIP peptides induce apoptosis in a cancer cell line. MCF-7 cells were treated for 24 hours with 3 μM (top panels) or 10 μM (bottom panels) of KIP peptide HRRIKAWLKKIKALARQLGVAA [SEQ ID NO: 166]. The cells were stained with Hoescht dye (panels A and D; blue), Annexin V antibody (panels B and E; green), and propidium iodide (panels C and F; red). For both concentrations tested, annexin V staining was much more intense than propidium iodide staining indicating that KIP peptides can induce apoptosis in a cancer cell line.

As seen in FIG. 8, MCF-7 breast cancer cells have a high degree of Annexin V staining relative to propidium iodide staining for both concentrations of KIP peptide. These results indicate that KIP peptides can induce apoptosis in a cancer cell line.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for inhibiting a kinase activity of a Ca2+/calmodulin-dependent protein kinase I (CaMKI) family kinase, the method comprising the step of providing a kinase inhibiting composition,
   wherein the kinase inhibiting composition comprises an inhibitory amount of a kinase inhibiting peptide,
   wherein the kinase inhibiting peptide comprises an amino acid sequence according to Formula VI:
   Z1-X1-X2-X3-X4-X5-X6-X7-X8-X9-X10-Z2 [Formula VI] [SEQ ID NO: 226],
   wherein
   each of Z1 and Z2 is absent or is a transduction domain;
   X1 is KA;
   X2 is L;
   X3 is A;
   X4 is R;
   X5 is selected from the group consisting of Q and N;
   X6 is L;
   X7 is G;
   X8 is V;
   X9 is A;
   X10 is A, and
   wherein the Ca2+/calmodulin-dependent protein kinase I (CaMKI) family kinase contacts the kinase inhibiting composition, and wherein the activity of the Ca2+/calmodulin-dependent protein kinase I (CaMKI) family kinase is inhibited.

2. The method according to claim 1, wherein the amino acid sequence of the kinase inhibiting peptide is WLR-RIKAWLRRIKALARQLGVAA [SEQ ID NO: 113].

3. The method according to claim 1, wherein the amino acid sequence of the kinase inhibiting peptide is KAFAK-LAARLYRKALARQLGVAA [SEQ ID NO: 173].

4. The method according to claim 1, wherein the amino acid sequence of the kinase inhibiting peptide is FAKLAAR-LYRKALARQLGVAA [SEQ ID NO: 163].

5. The method according to claim 1, wherein the $Ca^{2+}$/calmodulin-dependent protein kinase I (CaMKI) family kinase is selected from the group consisting of: CaMKI, CaMKIδ, and CaMKI1β.

6. A method for inhibiting hyperplasia in a cell population, the method comprising the step of providing a therapeutically effective amount of a kinase inhibiting composition to a subject in need thereof,
   wherein the kinase inhibiting composition comprises an inhibitory amount of a kinase inhibiting peptide,
   wherein the kinase inhibiting peptide inhibits a kinase activity of a Ca2+/calmodulin-dependent protein kinase I (CaMKI) family kinase,
   wherein the kinase inhibiting peptide is YARAAARQAR-AKALARQLGVAA [SEQ ID NO: 106]; and
   wherein at least one hyperplastic cell contacts the kinase inhibiting composition, and wherein the hyperplasia of the at least one hyperplastic cell is inhibited.

7. A method for inhibiting growth of a neoplasm, the method comprising the step of providing a therapeutically effective amount of a kinase inhibiting composition to a subject in need thereof,
   wherein the kinase inhibiting composition comprises an inhibitory amount of a kinase inhibiting peptide,
   wherein the kinase inhibiting peptide inhibits a kinase activity of a Ca2+/calmodulin-dependent protein kinase I (CaMKI) family kinase,
   wherein the amino acid sequence of the kinase inhibiting peptide is selected from the group consisting of FAK-LAARLYRKALARQLGVAA [SEQ ID NO: 163] and HRRIKAWLKKIKALARQLGVAA [SEQ ID NO: 166], and
   wherein the kinase inhibiting composition contacts the neoplasm, and wherein the growth of the neoplasm is inhibited.

8. The method according to claim 7, wherein the neoplasm is a carcinoma.

9. A method for inducing programmed cell death in a cell population, the method comprising the step of providing a kinase inhibiting composition,
   wherein the kinase inhibiting composition comprises an inhibitory amount of a kinase inhibiting peptide,
   wherein the kinase inhibiting peptide inhibits a kinase activity of a Ca2+/calmodulin-dependent protein kinase I (CaMKI) family kinase,
   wherein the kinase inhibiting peptide is HRRIKAWLK-KIKALARQLGVAA [SEQ ID NO: 166], and
   wherein the kinase inhibiting composition contacts at least one cell in the cell population, and wherein programmed cell death of the at least one cell is induced.

10. The method according to claim 9, wherein the cell is a prokaryotic cell.

11. The method according to claim 9, wherein the cell is a eukaryotic cell.

12. The method according to claim 9, wherein the programmed cell death occurs by apoptosis.

13. The method according to claim 7, wherein the neoplasm is selected from the group consisting of a breast cancer, a central nervous system cancer, a colon cancer, a pancreatic cancer, a prostate cancer, and a lung cancer.

14. The method according to claim 1, wherein the kinase inhibiting peptide is HRRIKAWLKKIKALARQLGVAA [SEQ ID NO: 166].

15. The method according to claim 1, wherein the kinase inhibiting peptide is YARAAARQARAKALARQLGVAA [SEQ ID NO: 106].

16. The method according to claim 7, wherein the kinase inhibiting peptide is HRRIKAWLKKIKALARQLGVAA [SEQ ID NO: 166].

17. The method according to claim 7, wherein the kinase inhibiting peptide is FAKLAARLYRKALARQLGVAA [SEQ ID NO: 163].

18. An isolated polypeptide of the formula HRRIKAWLKKIKALARQLGVAA [SEQ ID NO: 166].

19. A composition comprising the polypeptide of claim 18 and a pharmaceutically acceptable carrier.

20. A method for inhibiting growth of a neoplasm, the method comprising the step of providing a therapeutically effective amount of a kinase inhibiting composition to a subject in need thereof,
   wherein the neoplasm is selected from the group consisting of a melanoma, a prostate cancer, and a lung cancer,
      wherein the kinase inhibiting composition comprises an inhibitory amount of a kinase inhibiting peptide,
      wherein the kinase inhibiting peptide inhibits a kinase activity of a Ca2+/calmodulin-dependent protein kinase I (CaMKI) family kinase,
      wherein the amino acid sequence of the kinase inhibiting peptide is KAFAKLAARLYRKALARQLGVAA [SEQ ID NO: 173], and
   wherein the kinase inhibiting composition contacts the neoplasm, and wherein the growth of the neoplasm is inhibited.

21. A method for inhibiting growth of a neoplasm, the method comprising the step of providing a therapeutically effective amount of a kinase inhibiting composition to a subject in need thereof,
   wherein the neoplasm is a breast cancer,
      wherein the kinase inhibiting composition comprises an inhibitory amount of a kinase inhibiting peptide,
      wherein the kinase inhibiting peptide inhibits a kinase activity of a Ca2+/calmodulin-dependent protein kinase I (CaMKI) family kinase,
      wherein the amino acid sequence of the kinase inhibiting peptide is YARAAARQARAKALARQLGVAA [SEQ ID NO: 106], and
   wherein the kinase inhibiting composition contacts the neoplasm, and wherein the growth of the neoplasm is inhibited.

* * * * *

SEQUENCE LISTING

```
<160> NUMBER OF SEQ ID NOS: 229

<210> SEQ ID NO 1
<211> LENGTH: 9
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: misc_feature
<222> LOCATION: (1)..(9)
<223> OTHER INFORMATION: This region may encompass 4 to 9 "Arg" residues

<400> SEQUENCE: 1

Arg Arg Arg Arg Arg Arg Arg Arg Arg
1               5

<210> SEQ ID NO 2
```

```
<211> LENGTH: 13
<212> TYPE: PRT
<213> ORGANISM: Unknown
<220> FEATURE:
<223> OTHER INFORMATION: Description of Unknown: Mammalian
      sequence

<400> SEQUENCE: 2

Gly Arg Lys Lys Arg Arg Gln Arg Arg Pro Pro Gln
1               5                   10

<210> SEQ ID NO 3
<211> LENGTH: 12
<212> TYPE: PRT
<213> ORGANISM: Unknown
<220> FEATURE:
<223> OTHER INFORMATION: Description of Unknown: Mammalian
      sequence

<400> SEQUENCE: 3

Ala Tyr Ala Arg Ala Ala Arg Gln Ala Arg Ala
1               5                   10

<210> SEQ ID NO 4
<211> LENGTH: 34
<212> TYPE: PRT
<213> ORGANISM: Unknown
<220> FEATURE:
<223> OTHER INFORMATION: Description of Unknown: Mammalian
      sequence

<400> SEQUENCE: 4

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 5
<211> LENGTH: 27
<212> TYPE: PRT
<213> ORGANISM: Unknown
<220> FEATURE:
<223> OTHER INFORMATION: Description of Unknown: Mammalian
      sequence

<400> SEQUENCE: 5

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 6
<211> LENGTH: 12
<212> TYPE: PRT
<213> ORGANISM: Unknown
<220> FEATURE:
<223> OTHER INFORMATION: Description of Unknown: Mammalian
      sequence

<400> SEQUENCE: 6

Pro Leu Ser Ser Ile Phe Ser Arg Ile Gly Asp Pro
1               5                   10

<210> SEQ ID NO 7
<211> LENGTH: 16
<212> TYPE: PRT
```

-continued

```
<213> ORGANISM: Unknown
<220> FEATURE:
<223> OTHER INFORMATION: Description of Unknown: Mammalian
      sequence

<400> SEQUENCE: 7

Ala Ala Val Ala Leu Leu Pro Ala Val Leu Leu Ala Leu Leu Ala Pro
1               5                   10                  15

<210> SEQ ID NO 8
<211> LENGTH: 12
<212> TYPE: PRT
<213> ORGANISM: Unknown
<220> FEATURE:
<223> OTHER INFORMATION: Description of Unknown: Mammalian
      sequence

<400> SEQUENCE: 8

Ala Ala Val Leu Leu Pro Val Leu Leu Ala Ala Pro
1               5                   10

<210> SEQ ID NO 9
<211> LENGTH: 15
<212> TYPE: PRT
<213> ORGANISM: Unknown
<220> FEATURE:
<223> OTHER INFORMATION: Description of Unknown: Mammalian
      sequence

<400> SEQUENCE: 9

Val Thr Val Leu Ala Leu Gly Ala Leu Ala Gly Val Gly Val Gly
1               5                   10                  15

<210> SEQ ID NO 10
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 10

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 11
<211> LENGTH: 27
<212> TYPE: PRT
<213> ORGANISM: Unknown
<220> FEATURE:
<223> OTHER INFORMATION: Description of Unknown: Mammalian
      sequence

<400> SEQUENCE: 11

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 12
<211> LENGTH: 18
<212> TYPE: PRT
<213> ORGANISM: Unknown
<220> FEATURE:
<223> OTHER INFORMATION: Description of Unknown: Mammalian
      sequence
```

```
<400> SEQUENCE: 12

Lys Leu Ala Leu Lys Leu Ala Leu Lys Ala Leu Lys Ala Ala Leu Lys
1               5                   10                  15

Leu Ala

<210> SEQ ID NO 13
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 13

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 14
<211> LENGTH: 14
<212> TYPE: PRT
<213> ORGANISM: Unknown
<220> FEATURE:
<223> OTHER INFORMATION: Description of Unknown: Mammalian
      sequence

<400> SEQUENCE: 14

Lys Ala Phe Ala Lys Leu Ala Ala Arg Leu Tyr Arg Lys Ala
1               5                   10

<210> SEQ ID NO 15
<211> LENGTH: 14
<212> TYPE: PRT
<213> ORGANISM: Unknown
<220> FEATURE:
<223> OTHER INFORMATION: Description of Unknown: Mammalian
      sequence

<400> SEQUENCE: 15

Lys Ala Phe Ala Lys Leu Ala Ala Arg Leu Tyr Arg Ala Ala
1               5                   10

<210> SEQ ID NO 16
<211> LENGTH: 14
<212> TYPE: PRT
<213> ORGANISM: Unknown
<220> FEATURE:
<223> OTHER INFORMATION: Description of Unknown: Mammalian
      sequence

<400> SEQUENCE: 16

Ala Ala Phe Ala Lys Leu Ala Ala Arg Leu Tyr Arg Lys Ala
1               5                   10

<210> SEQ ID NO 17
<211> LENGTH: 14
<212> TYPE: PRT
<213> ORGANISM: Unknown
<220> FEATURE:
<223> OTHER INFORMATION: Description of Unknown: Mammalian
      sequence

<400> SEQUENCE: 17

Lys Ala Phe Ala Lys Leu Ala Ala Arg Leu Tyr Arg Lys Ala
1               5                   10
```

<210> SEQ ID NO 18
<211> LENGTH: 16
<212> TYPE: PRT
<213> ORGANISM: Unknown
<220> FEATURE:
<223> OTHER INFORMATION: Description of Unknown: Mammalian
      sequence

<400> SEQUENCE: 18

Lys Ala Phe Ala Lys Leu Ala Ala Arg Leu Tyr Arg Lys Ala Gly Cys
1               5                   10                  15

<210> SEQ ID NO 19
<211> LENGTH: 16
<212> TYPE: PRT
<213> ORGANISM: Unknown
<220> FEATURE:
<223> OTHER INFORMATION: Description of Unknown: Mammalian
      sequence

<400> SEQUENCE: 19

Lys Ala Phe Ala Lys Leu Ala Ala Arg Leu Tyr Arg Ala Ala Gly Cys
1               5                   10                  15

<210> SEQ ID NO 20
<211> LENGTH: 16
<212> TYPE: PRT
<213> ORGANISM: Unknown
<220> FEATURE:
<223> OTHER INFORMATION: Description of Unknown: Mammalian
      sequence

<400> SEQUENCE: 20

Ala Ala Phe Ala Lys Leu Ala Ala Arg Leu Tyr Arg Lys Ala Gly Cys
1               5                   10                  15

<210> SEQ ID NO 21
<211> LENGTH: 16
<212> TYPE: PRT
<213> ORGANISM: Unknown
<220> FEATURE:
<223> OTHER INFORMATION: Description of Unknown: Mammalian
      sequence

<400> SEQUENCE: 21

Lys Ala Phe Ala Lys Leu Ala Ala Arg Leu Tyr Arg Lys Ala Gly Cys
1               5                   10                  15

<210> SEQ ID NO 22
<211> LENGTH: 16
<212> TYPE: PRT
<213> ORGANISM: Unknown
<220> FEATURE:
<223> OTHER INFORMATION: Description of Unknown: Mammalian
      sequence

<400> SEQUENCE: 22

Lys Ala Phe Ala Lys Leu Ala Ala Gln Leu Tyr Arg Lys Ala Gly Cys
1               5                   10                  15

<210> SEQ ID NO 23
<211> LENGTH: 16
<212> TYPE: PRT
<213> ORGANISM: Unknown
<220> FEATURE:
<223> OTHER INFORMATION: Description of Unknown: Mammalian
      sequence

```
<400> SEQUENCE: 23

Ala Gly Gly Gly Gly Tyr Gly Arg Lys Lys Arg Arg Gln Arg Arg
1               5                   10                  15

<210> SEQ ID NO 24
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 24

Tyr Gly Arg Lys Lys Arg Arg Gln Arg Arg Arg
1               5                   10

<210> SEQ ID NO 25
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 25

Tyr Ala Arg Ala Ala Ala Arg Gln Ala Arg Ala
1               5                   10

<210> SEQ ID NO 26
<211> LENGTH: 8
<212> TYPE: PRT
<213> ORGANISM: Unknown
<220> FEATURE:
<223> OTHER INFORMATION: Description of Unknown: Mammalian
      sequence

<400> SEQUENCE: 26

Arg Gln Arg Arg Lys Lys Arg Gly
1               5

<210> SEQ ID NO 27
<211> LENGTH: 8
<212> TYPE: PRT
<213> ORGANISM: Unknown
<220> FEATURE:
<223> OTHER INFORMATION: Description of Unknown: Mammalian
      sequence

<400> SEQUENCE: 27

Gly Arg Lys Lys Arg Arg Gln Arg
1               5

<210> SEQ ID NO 28
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 28

Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 29
```

```
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 29

Tyr Gly Arg Lys Lys Arg Arg Gln Arg Arg Lys Ala Leu Asn Arg
1               5                   10                  15

Gln Leu Gly Val Ala
            20

<210> SEQ ID NO 30
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 30

Gly Arg Lys Lys Arg Arg Gln Arg Lys Ala Leu Asn Arg Gln Leu Gly
1               5                   10                  15

Val Ala

<210> SEQ ID NO 31
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 31

Arg Gln Arg Arg Lys Lys Arg Gly Lys Ala Leu Asn Arg Gln Leu Gly
1               5                   10                  15

Val Ala

<210> SEQ ID NO 32
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 32

Trp Leu Arg Arg Ile Lys Ala Trp Leu Arg Arg Ile Lys Ala Lys Ala
1               5                   10                  15

Leu Asn Arg Gln Leu Gly Val Ala
            20

<210> SEQ ID NO 33
<211> LENGTH: 31
<212> TYPE: PRT
<213> ORGANISM: Unknown
<220> FEATURE:
<223> OTHER INFORMATION: Description of Unknown: Mammalian
      sequence

<400> SEQUENCE: 33

Trp Leu Arg Arg Ile Lys Ala Trp Leu Arg Arg Ile Lys Ala Trp Leu
1               5                   10                  15

Arg Arg Ile Lys Ala Lys Ala Leu Asn Arg Gln Leu Gly Val Ala
            20                  25                  30
```

<210> SEQ ID NO 34
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 34

Tyr Ala Arg Ala Ala Ala Arg Gln Ala Arg Ala Lys Lys Lys Ala Leu
1               5                   10                  15

Asn Arg Gln Leu Gly Val Ala
            20

<210> SEQ ID NO 35
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 35

Tyr Gly Arg Lys Lys Arg Arg Gln Arg Arg Lys Lys Lys Ala Leu
1               5                   10                  15

Asn Arg Gln Leu Gly Val Ala
            20

<210> SEQ ID NO 36
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 36

Arg Gln Arg Arg Lys Lys Arg Gly Lys Lys Lys Ala Leu Asn Arg Gln
1               5                   10                  15

Leu Gly Val Ala
            20

<210> SEQ ID NO 37
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 37

Gly Arg Lys Lys Arg Arg Gln Arg Lys Lys Lys Ala Leu Asn Arg Gln
1               5                   10                  15

Leu Gly Val Ala
            20

<210> SEQ ID NO 38
<211> LENGTH: 26
<212> TYPE: PRT
<213> ORGANISM: Unknown
<220> FEATURE:
<223> OTHER INFORMATION: Description of Unknown: Mammalian
      sequence

<400> SEQUENCE: 38

-continued

Trp Leu Arg Arg Ile Lys Ala Trp Leu Arg Arg Ile Lys Ala Lys Lys
1               5                   10                  15

Lys Ala Leu Asn Arg Gln Leu Gly Val Ala
            20                  25

<210> SEQ ID NO 39
<211> LENGTH: 33
<212> TYPE: PRT
<213> ORGANISM: Unknown
<220> FEATURE:
<223> OTHER INFORMATION: Description of Unknown: Mammalian
      sequence

<400> SEQUENCE: 39

Trp Leu Arg Arg Ile Lys Ala Trp Leu Arg Arg Ile Lys Ala Trp Leu
1               5                   10                  15

Arg Arg Ile Lys Ala Lys Lys Ala Leu Asn Arg Gln Leu Gly Val
            20                  25                  30

Ala

<210> SEQ ID NO 40
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 40

Tyr Ala Arg Ala Ala Ala Arg Gln Ala Arg Ala Lys Lys Lys Ala Leu
1               5                   10                  15

Asn Arg Gly Leu Gly Val Ala
            20

<210> SEQ ID NO 41
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 41

Tyr Gly Arg Lys Lys Arg Arg Gln Arg Arg Lys Lys Lys Ala Leu
1               5                   10                  15

Asn Arg Gly Leu Gly Val Ala
            20

<210> SEQ ID NO 42
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 42

Arg Gln Arg Arg Lys Lys Arg Gly Lys Lys Lys Ala Leu Asn Arg Gly
1               5                   10                  15

Leu Gly Val Ala
            20

<210> SEQ ID NO 43
<211> LENGTH: 20
<212> TYPE: PRT

-continued

```
<213> ORGANISM: Unknown
<220> FEATURE:
<223> OTHER INFORMATION: Description of Unknown: Mammalian
      sequence

<400> SEQUENCE: 43

Gly Arg Lys Lys Arg Arg Gln Arg Lys Lys Ala Leu Asn Arg Gly
1               5                   10                  15

Leu Gly Val Ala
            20

<210> SEQ ID NO 44
<211> LENGTH: 26
<212> TYPE: PRT
<213> ORGANISM: Unknown
<220> FEATURE:
<223> OTHER INFORMATION: Description of Unknown: Mammalian
      sequence

<400> SEQUENCE: 44

Trp Leu Arg Arg Ile Lys Ala Trp Leu Arg Ile Lys Ala Lys Lys
1               5                   10                  15

Lys Ala Leu Asn Arg Gly Leu Gly Val Ala
            20                  25

<210> SEQ ID NO 45
<211> LENGTH: 33
<212> TYPE: PRT
<213> ORGANISM: Unknown
<220> FEATURE:
<223> OTHER INFORMATION: Description of Unknown: Mammalian
      sequence

<400> SEQUENCE: 45

Trp Leu Arg Arg Ile Lys Ala Trp Leu Arg Arg Ile Lys Ala Trp Leu
1               5                   10                  15

Arg Arg Ile Lys Ala Lys Lys Ala Leu Asn Arg Gly Leu Gly Val
            20                  25                  30

Ala

<210> SEQ ID NO 46
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 46

Tyr Ala Arg Ala Ala Ala Arg Gln Ala Arg Ala Lys Lys Lys Ala Leu
1               5                   10                  15

Asn Arg Gln Leu Ala Val Ala
            20

<210> SEQ ID NO 47
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 47

Tyr Gly Arg Lys Lys Arg Arg Gln Arg Arg Lys Lys Lys Ala Leu
1               5                   10                  15
```

Asn Arg Gln Leu Ala Val Ala
            20

<210> SEQ ID NO 48
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 48

Arg Gln Arg Arg Lys Lys Arg Gly Lys Lys Ala Leu Asn Arg Gln
1               5                   10                  15

Leu Ala Val Ala
            20

<210> SEQ ID NO 49
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 49

Gly Arg Lys Lys Arg Arg Gln Arg Lys Lys Lys Ala Leu Asn Arg Gln
1               5                   10                  15

Leu Ala Val Ala
            20

<210> SEQ ID NO 50
<211> LENGTH: 26
<212> TYPE: PRT
<213> ORGANISM: Unknown
<220> FEATURE:
<223> OTHER INFORMATION: Description of Unknown: Mammalian
      sequence

<400> SEQUENCE: 50

Trp Leu Arg Arg Ile Lys Ala Trp Leu Arg Arg Ile Lys Ala Lys Lys
1               5                   10                  15

Lys Ala Leu Asn Arg Gln Leu Ala Val Ala
            20                  25

<210> SEQ ID NO 51
<211> LENGTH: 33
<212> TYPE: PRT
<213> ORGANISM: Unknown
<220> FEATURE:
<223> OTHER INFORMATION: Description of Unknown: Mammalian
      sequence

<400> SEQUENCE: 51

Trp Leu Arg Arg Ile Lys Ala Trp Leu Arg Arg Ile Lys Ala Trp Leu
1               5                   10                  15

Arg Arg Ile Lys Ala Lys Lys Lys Ala Leu Asn Arg Gln Leu Ala Val
            20                  25                  30

Ala

<210> SEQ ID NO 52
<211> LENGTH: 23
<212> TYPE: PRT
<213> ORGANISM: Unknown
<220> FEATURE:
<223> OTHER INFORMATION: Description of Unknown: Mammalian

```
                              sequence

<400> SEQUENCE: 52

Tyr Ala Arg Ala Ala Ala Arg Gln Ala Arg Ala Lys Lys Ala Leu
1               5                   10                  15

Ala Arg Gln Leu Gly Val Ala
            20

<210> SEQ ID NO 53
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 53

Tyr Gly Arg Lys Lys Arg Arg Gln Arg Arg Lys Lys Lys Ala Leu
1               5                   10                  15

Ala Arg Gln Leu Gly Val Ala
            20

<210> SEQ ID NO 54
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 54

Arg Gln Arg Arg Lys Lys Arg Gly Lys Lys Lys Ala Leu Ala Arg Gln
1               5                   10                  15

Leu Gly Val Ala
            20

<210> SEQ ID NO 55
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 55

Gly Arg Lys Lys Arg Arg Gln Arg Lys Lys Lys Ala Leu Ala Arg Gln
1               5                   10                  15

Leu Gly Val Ala
            20

<210> SEQ ID NO 56
<211> LENGTH: 26
<212> TYPE: PRT
<213> ORGANISM: Unknown
<220> FEATURE:
<223> OTHER INFORMATION: Description of Unknown: Mammalian
      sequence

<400> SEQUENCE: 56

Trp Leu Arg Arg Ile Lys Ala Trp Leu Arg Arg Ile Lys Ala Lys Lys
1               5                   10                  15

Lys Ala Leu Ala Arg Gln Leu Gly Val Ala
            20                  25

<210> SEQ ID NO 57
```

```
<211> LENGTH: 33
<212> TYPE: PRT
<213> ORGANISM: Unknown
<220> FEATURE:
<223> OTHER INFORMATION: Description of Unknown: Mammalian
      sequence

<400> SEQUENCE: 57

Trp Leu Arg Arg Ile Lys Ala Trp Leu Arg Ile Lys Ala Trp Leu
1               5                   10                  15

Arg Arg Ile Lys Ala Lys Lys Ala Leu Ala Arg Gln Leu Gly Val
            20                  25                  30

Ala

<210> SEQ ID NO 58
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 58

Tyr Ala Arg Ala Ala Ala Arg Gln Ala Arg Ala Lys Ala Leu Asn Arg
1               5                   10                  15

Gly Leu Gly Val Ala
            20

<210> SEQ ID NO 59
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 59

Tyr Gly Arg Lys Lys Arg Arg Gln Arg Arg Lys Ala Leu Asn Arg
1               5                   10                  15

Gly Leu Gly Val Ala
            20

<210> SEQ ID NO 60
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 60

Arg Gln Arg Arg Lys Lys Arg Gly Lys Ala Leu Asn Arg Gly Leu Gly
1               5                   10                  15

Val Ala

<210> SEQ ID NO 61
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 61

Gly Arg Lys Lys Arg Arg Gln Arg Lys Ala Leu Asn Arg Gly Leu Gly
1               5                   10                  15
```

Val Ala

<210> SEQ ID NO 62
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 62

Trp Leu Arg Arg Ile Lys Ala Trp Leu Arg Arg Ile Lys Ala Lys Ala
1               5                   10                  15

Leu Asn Arg Gly Leu Gly Val Ala
            20

<210> SEQ ID NO 63
<211> LENGTH: 31
<212> TYPE: PRT
<213> ORGANISM: Unknown
<220> FEATURE:
<223> OTHER INFORMATION: Description of Unknown: Mammalian
      sequence

<400> SEQUENCE: 63

Trp Leu Arg Arg Ile Lys Ala Trp Leu Arg Arg Ile Lys Ala Trp Leu
1               5                   10                  15

Arg Arg Ile Lys Ala Lys Ala Leu Asn Arg Gly Leu Gly Val Ala
            20                  25                  30

<210> SEQ ID NO 64
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 64

Tyr Ala Arg Ala Ala Ala Arg Gln Ala Arg Ala Lys Ala Leu Asn Arg
1               5                   10                  15

Gln Leu Ala Val Ala
            20

<210> SEQ ID NO 65
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 65

Tyr Gly Arg Lys Lys Arg Arg Gln Arg Arg Lys Ala Leu Asn Arg
1               5                   10                  15

Gln Leu Ala Val Ala
            20

<210> SEQ ID NO 66
<211> LENGTH: 18
<212> TYPE: PRT
<213> ORGANISM: Unknown
<220> FEATURE:
<223> OTHER INFORMATION: Description of Unknown: Mammalian
      sequence

```
<400> SEQUENCE: 66

Arg Gln Arg Arg Lys Lys Arg Gly Lys Ala Leu Asn Arg Gln Leu Ala
1               5                   10                  15

Val Ala

<210> SEQ ID NO 67
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 67

Gly Arg Lys Lys Arg Arg Gln Arg Lys Ala Leu Asn Arg Gln Leu Ala
1               5                   10                  15

Val Ala

<210> SEQ ID NO 68
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 68

Trp Leu Arg Arg Ile Lys Ala Trp Leu Arg Arg Ile Lys Ala Lys Ala
1               5                   10                  15

Leu Asn Arg Gln Leu Ala Val Ala
            20

<210> SEQ ID NO 69
<211> LENGTH: 31
<212> TYPE: PRT
<213> ORGANISM: Unknown
<220> FEATURE:
<223> OTHER INFORMATION: Description of Unknown: Mammalian
      sequence

<400> SEQUENCE: 69

Trp Leu Arg Arg Ile Lys Ala Trp Leu Arg Arg Ile Lys Ala Trp Leu
1               5                   10                  15

Arg Arg Ile Lys Ala Lys Ala Leu Asn Arg Gln Leu Ala Val Ala
            20                  25                  30

<210> SEQ ID NO 70
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 70

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 71
<211> LENGTH: 21
<212> TYPE: PRT
<213> ORGANISM: Unknown
<220> FEATURE:
```

```
<223> OTHER INFORMATION: Description of Unknown: Mammalian
      sequence

<400> SEQUENCE: 71

Tyr Gly Arg Lys Lys Arg Arg Gln Arg Arg Lys Ala Leu Ala Arg
1               5                   10                  15

Gln Leu Gly Val Ala
            20

<210> SEQ ID NO 72
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 72

Arg Gln Arg Arg Lys Lys Arg Gly Lys Ala Leu Ala Arg Gln Leu Gly
1               5                   10                  15

Val Ala

<210> SEQ ID NO 73
<211> LENGTH: 18
<212> TYPE: PRT
<213> ORGANISM: Unknown
<220> FEATURE:
<223> OTHER INFORMATION: Description of Unknown: Mammalian
      sequence

<400> SEQUENCE: 73

Gly Arg Lys Lys Arg Arg Gln Arg Lys Ala Leu Ala Arg Gln Leu Gly
1               5                   10                  15

Val Ala

<210> SEQ ID NO 74
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 74

Trp Leu Arg Arg Ile Lys Ala Trp Leu Arg Arg Ile Lys Ala Lys Ala
1               5                   10                  15

Leu Ala Arg Gln Leu Gly Val Ala
            20

<210> SEQ ID NO 75
<211> LENGTH: 31
<212> TYPE: PRT
<213> ORGANISM: Unknown
<220> FEATURE:
<223> OTHER INFORMATION: Description of Unknown: Mammalian
      sequence

<400> SEQUENCE: 75

Trp Leu Arg Arg Ile Lys Ala Trp Leu Arg Arg Ile Lys Ala Trp Leu
1               5                   10                  15

Arg Arg Ile Lys Ala Lys Ala Leu Ala Arg Gln Leu Gly Val Ala
            20                  25                  30

<210> SEQ ID NO 76
<211> LENGTH: 24
```

```
<212> TYPE: PRT
<213> ORGANISM: Unknown
<220> FEATURE:
<223> OTHER INFORMATION: Description of Unknown: Mammalian
      sequence

<400> SEQUENCE: 76

Tyr Ala Arg Ala Ala Ala Arg Gln Ala Arg Ala Lys Lys Lys Ala Leu
1               5                   10                  15

Asn Arg Gly Leu Gly Val Ala Ala
            20

<210> SEQ ID NO 77
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 77

Tyr Gly Arg Lys Lys Arg Arg Gln Arg Arg Lys Lys Lys Ala Leu
1               5                   10                  15

Asn Arg Gly Leu Gly Val Ala Ala
            20

<210> SEQ ID NO 78
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 78

Arg Gln Arg Arg Lys Lys Arg Gly Lys Lys Lys Ala Leu Asn Arg Gly
1               5                   10                  15

Leu Gly Val Ala Ala
            20

<210> SEQ ID NO 79
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 79

Gly Arg Lys Lys Arg Arg Gln Arg Lys Lys Lys Ala Leu Asn Arg Gly
1               5                   10                  15

Leu Gly Val Ala Ala
            20

<210> SEQ ID NO 80
<211> LENGTH: 27
<212> TYPE: PRT
<213> ORGANISM: Unknown
<220> FEATURE:
<223> OTHER INFORMATION: Description of Unknown: Mammalian
      sequence

<400> SEQUENCE: 80

Trp Leu Arg Arg Ile Lys Ala Trp Leu Arg Arg Ile Lys Ala Lys Lys
1               5                   10                  15

Lys Ala Leu Asn Arg Gly Leu Gly Val Ala Ala
```

20              25

<210> SEQ ID NO 81
<211> LENGTH: 34
<212> TYPE: PRT
<213> ORGANISM: Unknown
<220> FEATURE:
<223> OTHER INFORMATION: Description of Unknown: Mammalian
      sequence

<400> SEQUENCE: 81

Trp Leu Arg Arg Ile Lys Ala Trp Leu Arg Arg Ile Lys Ala Trp Leu
1               5                   10                  15

Arg Arg Ile Lys Ala Lys Lys Ala Leu Asn Arg Gly Leu Gly Val
            20                  25                  30

Ala Ala

<210> SEQ ID NO 82
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 82

Tyr Ala Arg Ala Ala Ala Arg Gln Ala Arg Ala Lys Lys Lys Ala Leu
1               5                   10                  15

Asn Arg Gln Leu Ala Val Ala Ala
            20

<210> SEQ ID NO 83
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 83

Tyr Gly Arg Lys Lys Arg Arg Gln Arg Arg Lys Lys Lys Ala Leu
1               5                   10                  15

Asn Arg Gln Leu Ala Val Ala Ala
            20

<210> SEQ ID NO 84
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 84

Arg Gln Arg Arg Lys Lys Arg Gly Lys Lys Lys Ala Leu Asn Arg Gln
1               5                   10                  15

Leu Ala Val Ala Ala
            20

<210> SEQ ID NO 85
<211> LENGTH: 21
<212> TYPE: PRT
<213> ORGANISM: Unknown
<220> FEATURE:
<223> OTHER INFORMATION: Description of Unknown: Mammalian
      sequence

```
<400> SEQUENCE: 85

Gly Arg Lys Lys Arg Arg Gln Arg Lys Lys Ala Leu Asn Arg Gln
1               5                   10                  15

Leu Ala Val Ala Ala
            20

<210> SEQ ID NO 86
<211> LENGTH: 27
<212> TYPE: PRT
<213> ORGANISM: Unknown
<220> FEATURE:
<223> OTHER INFORMATION: Description of Unknown: Mammalian
      sequence

<400> SEQUENCE: 86

Trp Leu Arg Arg Ile Lys Ala Trp Leu Arg Ile Lys Ala Lys Lys
1               5                   10                  15

Lys Ala Leu Asn Arg Gln Leu Ala Val Ala Ala
            20                  25

<210> SEQ ID NO 87
<211> LENGTH: 34
<212> TYPE: PRT
<213> ORGANISM: Unknown
<220> FEATURE:
<223> OTHER INFORMATION: Description of Unknown: Mammalian
      sequence

<400> SEQUENCE: 87

Trp Leu Arg Arg Ile Lys Ala Trp Leu Arg Ile Lys Ala Trp Leu
1               5                   10                  15

Arg Arg Ile Lys Ala Lys Lys Lys Ala Leu Asn Arg Gln Leu Ala Val
            20                  25                  30

Ala Ala

<210> SEQ ID NO 88
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 88

Tyr Ala Arg Ala Ala Arg Gln Ala Arg Lys Lys Lys Ala Leu
1               5                   10                  15

Ala Arg Gln Leu Gly Val Ala Ala
            20

<210> SEQ ID NO 89
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 89

Tyr Gly Arg Lys Lys Arg Arg Gln Arg Arg Lys Lys Ala Leu
1               5                   10                  15

Ala Arg Gln Leu Gly Val Ala Ala
            20
```

```
<210> SEQ ID NO 90
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 90

Arg Gln Arg Arg Lys Lys Arg Gly Lys Lys Ala Leu Ala Arg Gln
1               5                   10                  15

Leu Gly Val Ala Ala
            20

<210> SEQ ID NO 91
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 91

Gly Arg Lys Lys Arg Arg Gln Arg Lys Lys Ala Leu Ala Arg Gln
1               5                   10                  15

Leu Gly Val Ala Ala
            20

<210> SEQ ID NO 92
<211> LENGTH: 27
<212> TYPE: PRT
<213> ORGANISM: Unknown
<220> FEATURE:
<223> OTHER INFORMATION: Description of Unknown: Mammalian
      sequence

<400> SEQUENCE: 92

Trp Leu Arg Arg Ile Lys Ala Trp Leu Arg Arg Ile Lys Ala Lys Lys
1               5                   10                  15

Lys Ala Leu Ala Arg Gln Leu Gly Val Ala Ala
            20                  25

<210> SEQ ID NO 93
<211> LENGTH: 34
<212> TYPE: PRT
<213> ORGANISM: Unknown
<220> FEATURE:
<223> OTHER INFORMATION: Description of Unknown: Mammalian
      sequence

<400> SEQUENCE: 93

Trp Leu Arg Arg Ile Lys Ala Trp Leu Arg Arg Ile Lys Ala Trp Leu
1               5                   10                  15

Arg Arg Ile Lys Ala Lys Lys Lys Ala Leu Ala Arg Gln Leu Gly Val
            20                  25                  30

Ala Ala

<210> SEQ ID NO 94
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 94
```

```
Tyr Ala Arg Ala Ala Arg Gln Ala Arg Ala Lys Ala Leu Asn Arg
1               5                   10                  15

Gly Leu Gly Val Ala Ala
            20
```

<210> SEQ ID NO 95
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 95

```
Tyr Gly Arg Lys Lys Arg Arg Gln Arg Arg Lys Ala Leu Asn Arg
1               5                   10                  15

Gly Leu Gly Val Ala Ala
            20
```

<210> SEQ ID NO 96
<211> LENGTH: 19
<212> TYPE: PRT
<213> ORGANISM: Unknown
<220> FEATURE:
<223> OTHER INFORMATION: Description of Unknown: Mammalian
      sequence

<400> SEQUENCE: 96

```
Arg Gln Arg Arg Lys Lys Arg Gly Lys Ala Leu Asn Arg Gly Leu Gly
1               5                   10                  15

Val Ala Ala
```

<210> SEQ ID NO 97
<211> LENGTH: 19
<212> TYPE: PRT
<213> ORGANISM: Unknown
<220> FEATURE:
<223> OTHER INFORMATION: Description of Unknown: Mammalian
      sequence

<400> SEQUENCE: 97

```
Gly Arg Lys Lys Arg Arg Gln Arg Lys Ala Leu Asn Arg Gly Leu Gly
1               5                   10                  15

Val Ala Ala
```

<210> SEQ ID NO 98
<211> LENGTH: 25
<212> TYPE: PRT
<213> ORGANISM: Unknown
<220> FEATURE:
<223> OTHER INFORMATION: Description of Unknown: Mammalian
      sequence

<400> SEQUENCE: 98

```
Trp Leu Arg Arg Ile Lys Ala Trp Leu Arg Arg Ile Lys Ala Lys Ala
1               5                   10                  15

Leu Asn Arg Gly Leu Gly Val Ala Ala
            20                  25
```

<210> SEQ ID NO 99
<211> LENGTH: 32
<212> TYPE: PRT
<213> ORGANISM: Unknown
<220> FEATURE:
<223> OTHER INFORMATION: Description of Unknown: Mammalian
      sequence

```
<400> SEQUENCE: 99

Trp Leu Arg Arg Ile Lys Ala Trp Leu Arg Arg Ile Lys Ala Trp Leu
1               5                   10                  15
Arg Arg Ile Lys Ala Lys Ala Leu Asn Arg Gly Leu Gly Val Ala Ala
            20                  25                  30

<210> SEQ ID NO 100
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 100

Tyr Ala Arg Ala Ala Ala Arg Gln Ala Arg Ala Lys Ala Leu Asn Arg
1               5                   10                  15
Gln Leu Ala Val Ala Ala
            20

<210> SEQ ID NO 101
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 101

Tyr Gly Arg Lys Lys Arg Arg Gln Arg Arg Lys Ala Leu Asn Arg
1               5                   10                  15
Gln Leu Ala Val Ala Ala
            20

<210> SEQ ID NO 102
<211> LENGTH: 19
<212> TYPE: PRT
<213> ORGANISM: Unknown
<220> FEATURE:
<223> OTHER INFORMATION: Description of Unknown: Mammalian
      sequence

<400> SEQUENCE: 102

Arg Gln Arg Arg Lys Lys Arg Gly Lys Ala Leu Asn Arg Gln Leu Ala
1               5                   10                  15
Val Ala Ala

<210> SEQ ID NO 103
<211> LENGTH: 19
<212> TYPE: PRT
<213> ORGANISM: Unknown
<220> FEATURE:
<223> OTHER INFORMATION: Description of Unknown: Mammalian
      sequence

<400> SEQUENCE: 103

Gly Arg Lys Lys Arg Arg Gln Arg Lys Ala Leu Asn Arg Gln Leu Ala
1               5                   10                  15
Val Ala Ala

<210> SEQ ID NO 104
<211> LENGTH: 25
<212> TYPE: PRT
<213> ORGANISM: Unknown
```

-continued

```
<220> FEATURE:
<223> OTHER INFORMATION: Description of Unknown: Mammalian
      sequence

<400> SEQUENCE: 104

Trp Leu Arg Arg Ile Lys Ala Trp Leu Arg Arg Ile Lys Ala Lys Ala
1               5                   10                  15

Leu Asn Arg Gln Leu Ala Val Ala Ala
            20                  25

<210> SEQ ID NO 105
<211> LENGTH: 32
<212> TYPE: PRT
<213> ORGANISM: Unknown
<220> FEATURE:
<223> OTHER INFORMATION: Description of Unknown: Mammalian
      sequence

<400> SEQUENCE: 105

Trp Leu Arg Arg Ile Lys Ala Trp Leu Arg Arg Ile Lys Ala Trp Leu
1               5                   10                  15

Arg Arg Ile Lys Ala Lys Ala Leu Asn Arg Gln Leu Ala Val Ala Ala
            20                  25                  30

<210> SEQ ID NO 106
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 106

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 107
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 107

Tyr Gly Arg Lys Lys Arg Arg Gln Arg Arg Lys Ala Leu Ala Arg
1               5                   10                  15

Gln Leu Gly Val Ala Ala
            20

<210> SEQ ID NO 108
<211> LENGTH: 19
<212> TYPE: PRT
<213> ORGANISM: Unknown
<220> FEATURE:
<223> OTHER INFORMATION: Description of Unknown: Mammalian
      sequence

<400> SEQUENCE: 108

Arg Gln Arg Arg Lys Lys Arg Gly Lys Ala Leu Ala Arg Gln Leu Gly
1               5                   10                  15

Val Ala Ala
```

```
<210> SEQ ID NO 109
<211> LENGTH: 19
<212> TYPE: PRT
<213> ORGANISM: Unknown
<220> FEATURE:
<223> OTHER INFORMATION: Description of Unknown: Mammalian
      sequence

<400> SEQUENCE: 109

Gly Arg Lys Lys Arg Arg Gln Arg Lys Ala Leu Ala Arg Gln Leu Gly
1               5                   10                  15

Val Ala Ala

<210> SEQ ID NO 110
<211> LENGTH: 25
<212> TYPE: PRT
<213> ORGANISM: Unknown
<220> FEATURE:
<223> OTHER INFORMATION: Description of Unknown: Mammalian
      sequence

<400> SEQUENCE: 110

Trp Leu Arg Arg Ile Lys Ala Trp Leu Arg Arg Ile Lys Ala Lys Ala
1               5                   10                  15

Leu Ala Arg Gln Leu Gly Val Ala Ala
            20                  25

<210> SEQ ID NO 111
<211> LENGTH: 32
<212> TYPE: PRT
<213> ORGANISM: Unknown
<220> FEATURE:
<223> OTHER INFORMATION: Description of Unknown: Mammalian
      sequence

<400> SEQUENCE: 111

Trp Leu Arg Arg Ile Lys Ala Trp Leu Arg Arg Ile Lys Ala Trp Leu
1               5                   10                  15

Arg Arg Ile Lys Ala Lys Ala Leu Ala Arg Gln Leu Gly Val Ala Ala
            20                  25                  30

<210> SEQ ID NO 112
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 112

Tyr Ala Arg Ala Ala Ala Arg Gln Ala Arg Ala Lys Lys Lys Ala Leu
1               5                   10                  15

Ala Arg Gln Leu Ala Val Ala
            20

<210> SEQ ID NO 113
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 113

Trp Leu Arg Arg Ile Lys Ala Trp Leu Arg Arg Ile Lys Ala Leu Ala
1               5                   10                  15
```

-continued

Arg Gln Leu Gly Val Ala Ala
            20

<210> SEQ ID NO 114
<211> LENGTH: 10
<212> TYPE: PRT
<213> ORGANISM: Unknown
<220> FEATURE:
<223> OTHER INFORMATION: Description of Unknown: Mammalian
      sequence

<400> SEQUENCE: 114

Lys Ala Leu Asn Arg Gln Leu Gly Val Ala
1               5                   10

<210> SEQ ID NO 115
<211> LENGTH: 13
<212> TYPE: PRT
<213> ORGANISM: Unknown
<220> FEATURE:
<223> OTHER INFORMATION: Description of Unknown: Mammalian
      sequence

<400> SEQUENCE: 115

Lys Lys Lys Ala Leu Asn Arg Gln Leu Gly Val Ala Ala
1               5                   10

<210> SEQ ID NO 116
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 116

Lys Ala Leu Asn Arg Gln Leu Gly Val Ala Ala
1               5                   10

<210> SEQ ID NO 117
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 117

Lys Ala Ala Asn Arg Gln Leu Gly Val Ala Ala
1               5                   10

<210> SEQ ID NO 118
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 118

Lys Ala Leu Ala Arg Gln Leu Gly Val Ala Ala
1               5                   10

<210> SEQ ID NO 119
<211> LENGTH: 11
<212> TYPE: PRT
<213> ORGANISM: Unknown
<220> FEATURE:
<223> OTHER INFORMATION: Description of Unknown: Mammalian -continued

<400> SEQUENCE: 119

Lys Ala Leu Asn Ala Gln Leu Gly Val Ala Ala
1               5                   10

<210> SEQ ID NO 120
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 120

Lys Ala Leu Asn Arg Ala Leu Gly Val Ala Ala
1               5                   10

<210> SEQ ID NO 121
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 121

Lys Ala Leu Asn Arg Gln Ala Gly Val Ala Ala
1               5                   10

<210> SEQ ID NO 122
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 122

Lys Ala Leu Asn Arg Gln Leu Ala Val Ala Ala
1               5                   10

<210> SEQ ID NO 123
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 123

Lys Ala Leu Asn Arg Gln Leu Gly Ala Ala Ala
1               5                   10

<210> SEQ ID NO 124
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 124

Lys Ala Leu Asn Arg Gln Leu Gly Val Ala Ala
1               5                   10

<210> SEQ ID NO 125
<211> LENGTH: 10

```
<212> TYPE: PRT
<213> ORGANISM: Unknown
<220> FEATURE:
<223> OTHER INFORMATION: Description of Unknown: Mammalian
      sequence

<400> SEQUENCE: 125

Lys Ala Leu Asn Arg Gln Leu Gly Val Ala
1               5                   10

<210> SEQ ID NO 126
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 126

Lys Ala Ala Asn Arg Gln Leu Gly Val Ala Ala
1               5                   10

<210> SEQ ID NO 127
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 127

Lys Ala Leu Ala Arg Gln Leu Gly Val Ala Ala
1               5                   10

<210> SEQ ID NO 128
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 128

Lys Ala Leu Asn Ala Gln Leu Gly Val Ala Ala
1               5                   10

<210> SEQ ID NO 129
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 129

Lys Ala Leu Asn Arg Ala Leu Gly Val Ala Ala
1               5                   10

<210> SEQ ID NO 130
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 130

Lys Ala Leu Asn Arg Gln Ala Gly Val Ala Ala
1               5                   10
```

```
<210> SEQ ID NO 131
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 131

Lys Ala Leu Asn Arg Gln Leu Ala Val Ala Ala
1               5                   10

<210> SEQ ID NO 132
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 132

Lys Ala Leu Asn Arg Gln Leu Gly Ala Ala Ala
1               5                   10

<210> SEQ ID NO 133
<211> LENGTH: 13
<212> TYPE: PRT
<213> ORGANISM: Unknown
<220> FEATURE:
<223> OTHER INFORMATION: Description of Unknown: Mammalian
      sequence

<400> SEQUENCE: 133

Lys Lys Lys Ala Leu Asn Arg Gln Leu Gly Val Ala Ala
1               5                   10

<210> SEQ ID NO 134
<211> LENGTH: 14
<212> TYPE: PRT
<213> ORGANISM: Unknown
<220> FEATURE:
<223> OTHER INFORMATION: Description of Unknown: Mammalian transduction
      domain sequence

<400> SEQUENCE: 134

Trp Leu Arg Arg Ile Lys Ala Trp Leu Arg Arg Ile Lys Ala
1               5                   10

<210> SEQ ID NO 135
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 135

Tyr Ala Arg Ala Ala Ala Arg Gln Ala Arg Ala
1               5                   10

<210> SEQ ID NO 136
<211> LENGTH: 11
<212> TYPE: PRT
<213> ORGANISM: Unknown
<220> FEATURE:
<223> OTHER INFORMATION: Description of Unknown: Mammalian
      sequence
```

```
<400> SEQUENCE: 136

Tyr Gly Arg Lys Lys Arg Arg Gln Arg Arg
1               5                   10

<210> SEQ ID NO 137
<211> LENGTH: 7
<212> TYPE: PRT
<213> ORGANISM: Unknown
<220> FEATURE:
<223> OTHER INFORMATION: Description of Unknown: Mammalian
      sequence

<400> SEQUENCE: 137

Trp Leu Arg Arg Ile Lys Ala
1               5

<210> SEQ ID NO 138
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 138

Trp Leu Arg Arg Ile Lys Ala Trp Leu Arg Arg Ile Lys Ala Leu Ala
1               5                   10                  15

Arg Gln Leu Ala Val Ala
            20

<210> SEQ ID NO 139
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 139

Trp Leu Arg Arg Ile Lys Ala Trp Leu Arg Arg Ile Lys Ala Leu Ala
1               5                   10                  15

Arg Gln Leu Gly Val Ala
            20

<210> SEQ ID NO 140
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 140

Trp Leu Arg Arg Ile Lys Ala Trp Leu Arg Arg Ile Lys Ala Leu Asn
1               5                   10                  15

Arg Gln Leu Ala Val Ala
            20

<210> SEQ ID NO 141
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 141
```

Trp Leu Arg Arg Ile Lys Ala Trp Leu Arg Arg Ile Lys Ala Leu Asn
1               5                   10                  15

Arg Gln Leu Gly Val Ala
            20

<210> SEQ ID NO 142
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 142

Trp Leu Arg Arg Ile Lys Ala Trp Leu Arg Arg Ile Lys Ala Leu Asn
1               5                   10                  15

Arg Gln Leu Gly Val Ala Ala
            20

<210> SEQ ID NO 143
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 143

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 144
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 144

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 145
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 145

Tyr Ala Arg Ala Ala Ala Arg Gln Ala Arg Ala Lys Ala Leu Asn Arg
1               5                   10                  15

Gln Leu Ala Val Ala
            20

<210> SEQ ID NO 146
<211> LENGTH: 21
<212> TYPE: PRT
<213> ORGANISM: Unknown

```
<220> FEATURE:
<223> OTHER INFORMATION: Description of Unknown: Mammalian
      sequence

<400> SEQUENCE: 146

Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 147
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 147

Tyr Ala Arg Ala Ala Ala Arg Gln Ala Arg Ala Lys Ala Leu Asn Arg
1               5                   10                  15

Gln Leu Gly Val Ala Ala
            20

<210> SEQ ID NO 148
<211> LENGTH: 24
<212> TYPE: PRT
<213> ORGANISM: Unknown
<220> FEATURE:
<223> OTHER INFORMATION: Description of Unknown: Mammalian
      sequence

<400> SEQUENCE: 148

Trp Leu Arg Arg Ile Lys Ala Trp Leu Arg Arg Ile Lys Lys Lys Ala
1               5                   10                  15

Leu Ala Arg Gln Leu Ala Val Ala
            20

<210> SEQ ID NO 149
<211> LENGTH: 13
<212> TYPE: PRT
<213> ORGANISM: Unknown
<220> FEATURE:
<223> OTHER INFORMATION: Description of Unknown: Mammalian MEK1
      sequence

<400> SEQUENCE: 149

Gly Met Pro Lys Lys Lys Pro Thr Pro Ile Gln Leu Asn
1               5                   10

<210> SEQ ID NO 150
<211> LENGTH: 17
<212> TYPE: PRT
<213> ORGANISM: Unknown
<220> FEATURE:
<223> OTHER INFORMATION: Description of Unknown: Mammalian protein
      transduction sequence

<400> SEQUENCE: 150

Asp Arg Gln Ile Lys Ile Trp Phe Gln Asn Arg Arg Met Lys Trp Lys
1               5                   10                  15

Lys

<210> SEQ ID NO 151
<211> LENGTH: 13
<212> TYPE: PRT
```

-continued

```
<213> ORGANISM: Unknown
<220> FEATURE:
<223> OTHER INFORMATION: Description of Unknown: Mammalian autocamtide-2
      related inhibitory peptide sequence

<400> SEQUENCE: 151

Lys Lys Ala Leu Arg Arg Gln Glu Ala Val Asp Ala Leu
1               5                   10

<210> SEQ ID NO 152
<211> LENGTH: 9
<212> TYPE: PRT
<213> ORGANISM: Human immunodeficiency virus 1

<400> SEQUENCE: 152

Arg Lys Lys Arg Arg Gln Arg Arg Arg
1               5

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Ala Arg Ala Ala Ala Arg Gln Ala Arg Ala
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Arg Gln Arg Arg Thr Ser Lys Leu Met Lys Arg
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Ala Val Leu Leu Pro Val Leu Leu Ala Ala Arg
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Arg Arg Arg Arg Arg Arg Arg Arg Arg
1               5

<210> SEQ ID NO 157
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Gly Trp Phe Arg Arg Trp Lys Lys
1               5

<210> SEQ ID NO 158
<211> LENGTH: 16
<212> TYPE: PRT
<213> ORGANISM: Unknown
<220> FEATURE:
<223> OTHER INFORMATION: Description of Unknown: Mammalian
      Antp protein transduction domain sequence

<400> SEQUENCE: 158

Arg Gln Ile Lys Ile Trp Phe Gln Asn Arg Arg Met Lys Trp Lys Lys
1               5                   10                  15

<210> SEQ ID NO 159
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 159

Trp Leu Lys Lys Ile Lys Ala Trp Leu Lys Lys Ile Lys Ala Leu Asn
1               5                   10                  15

Arg Gln Leu Gly Val Val Ala
            20

<210> SEQ ID NO 160
<211> LENGTH: 12
<212> TYPE: PRT
<213> ORGANISM: Unknown
<220> FEATURE:
<223> OTHER INFORMATION: Description of Unknown: Mammalian
      sequence

<400> SEQUENCE: 160

Phe Ala Lys Leu Ala Ala Arg Leu Tyr Arg Lys Ala
1               5                   10

<210> SEQ ID NO 161
<211> LENGTH: 14
<212> TYPE: PRT
<213> ORGANISM: Unknown
<220> FEATURE:
<223> OTHER INFORMATION: Description of Unknown: Mammalian
      sequence

<400> SEQUENCE: 161

Phe Ala Lys Leu Ala Ala Arg Leu Tyr Arg Lys Ala Gly Cys
1               5                   10

<210> SEQ ID NO 162
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 162
```

```
Phe Ala Lys Leu Ala Ala Arg Leu Tyr Arg Lys Ala Leu Asn Arg Gln
1               5                   10                  15

Leu Gly Val Ala Ala
            20

<210> SEQ ID NO 163
<211> LENGTH: 21
<212> TYPE: PRT
<213> ORGANISM: Unknown
<220> FEATURE:
<223> OTHER INFORMATION: Description of Unknown: Mammalian
      sequence

<400> SEQUENCE: 163

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 164
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 164

Phe Ala Lys Leu Ala Ala Arg Leu Tyr Arg Lys Ala Leu Asn Arg Gln
1               5                   10                  15

Leu Gly Val Ala
            20

<210> SEQ ID NO 165
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 165

Phe Ala Lys Leu Ala Ala Arg Leu Tyr Arg Lys Ala Leu Ala Arg Gln
1               5                   10                  15

Leu Gly Val Ala
            20

<210> SEQ ID NO 166
<211> LENGTH: 22
<212> TYPE: PRT
<213> ORGANISM: Unknown
<220> FEATURE:
<223> OTHER INFORMATION: Description of Unknown: Mammalian kinase
      inhibitory peptide sequence

<400> SEQUENCE: 166

His Arg Arg Ile Lys Ala Trp Leu Lys Lys Ile Lys Ala Leu Ala Arg
1               5                   10                  15

Gln Leu Gly Val Ala Ala
            20

<210> SEQ ID NO 167
<211> LENGTH: 22
<212> TYPE: PRT
<213> ORGANISM: Unknown
```

```
<220> FEATURE:
<223> OTHER INFORMATION: Description of Unknown: Mammalian kinase
      inhibitory peptide sequence

<400> SEQUENCE: 167

Trp Leu Arg Arg Ile Lys Ala His Arg Arg Ile Lys Ala Leu Ala Arg
1               5                   10                  15

Gln Leu Gly Val Ala Ala
            20

<210> SEQ ID NO 168
<211> LENGTH: 11
<212> TYPE: PRT
<213> ORGANISM: Unknown
<220> FEATURE:
<223> OTHER INFORMATION: Description of Unknown: Mammalian kinase
      inhibitory peptide sequence

<400> SEQUENCE: 168

Trp Leu Arg Arg Ile Lys Ala Trp Leu Arg Arg
1               5                   10

<210> SEQ ID NO 169
<211> LENGTH: 21
<212> TYPE: PRT
<213> ORGANISM: Unknown
<220> FEATURE:
<223> OTHER INFORMATION: Description of Unknown: Mammalian kinase
      inhibitory peptide sequence

<400> SEQUENCE: 169

Trp Leu Arg Arg Ile Lys Ala Trp Leu Arg Arg Ala Leu Asn Arg Gln
1               5                   10                  15

Leu Gly Val Ala Ala
            20

<210> SEQ ID NO 170
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 170

Tyr Ala Arg Ala Ala Ala Arg Gln Ala Arg Ala Leu Asn Arg Gln Leu
1               5                   10                  15

Gly Val Ala Ala
            20

<210> SEQ ID NO 171
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 171

Tyr Ala Arg Ala Ala Ala Arg Gln Ala Arg Ala Leu Ala Arg Gln Leu
1               5                   10                  15

Gly Val Ala Ala
            20

<210> SEQ ID NO 172
<211> LENGTH: 23
```

```
<212> TYPE: PRT
<213> ORGANISM: Unknown
<220> FEATURE:
<223> OTHER INFORMATION: Description of Unknown: Mammalian
      sequence

<400> SEQUENCE: 172

Lys Ala Phe Ala Lys Leu Ala Ala Arg Leu Tyr Arg Lys Ala Leu Asn
1               5                   10                  15

Arg Gln Leu Gly Val Ala Ala
            20

<210> SEQ ID NO 173
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 173

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 174
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 174

Lys Ala Phe Ala Lys Leu Ala Ala Arg Leu Tyr Arg Lys Ala Leu Asn
1               5                   10                  15

Arg Gln Leu Gly Val Ala
            20

<210> SEQ ID NO 175
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 175

Lys Ala Phe Ala Lys Leu Ala Ala Arg Leu Tyr Arg Lys Ala Leu Ala
1               5                   10                  15

Arg Gln Leu Gly Val Ala
            20

<210> SEQ ID NO 176
<211> LENGTH: 21
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: misc_feature
<222> LOCATION: (1)..(21)
<223> OTHER INFORMATION: This sequence may disclose 7, 14 or 21 residues
      which encompass 1 to 3 "Trp Leu Arg Arg Ile Lys Ala" repeats

<400> SEQUENCE: 176
```

```
Trp Leu Arg Arg Ile Lys Ala Trp Leu Arg Arg Ile Lys Ala Trp Leu
1               5                   10                  15

Arg Arg Ile Lys Ala
            20

<210> SEQ ID NO 177
<211> LENGTH: 20
<212> TYPE: PRT
<213> ORGANISM: Unknown
<220> FEATURE:
<223> OTHER INFORMATION: Description of Unknown: Mammalian
      sequence

<400> SEQUENCE: 177

Trp Leu Arg Arg Ile Lys Ala Trp Leu Arg Arg Ala Leu Ala Arg Gln
1               5                   10                  15

Leu Gly Val Ala
            20

<210> SEQ ID NO 178
<211> LENGTH: 23
<212> TYPE: PRT
<213> ORGANISM: Unknown
<220> FEATURE:
<223> OTHER INFORMATION: Description of Unknown: Mammalian
      sequence

<400> SEQUENCE: 178

Trp Leu Arg Arg Ile Lys Ala Trp Leu Arg Arg Ile Lys Ala Leu Asn
1               5                   10                  15

Arg Gln Leu Gly Val Ala Ala
            20

<210> SEQ ID NO 179
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (2)..(2)
<223> OTHER INFORMATION: D-Ala

<400> SEQUENCE: 179

Lys Ala Leu Asn Arg Gln Leu Gly Val Ala Ala
1               5                   10

<210> SEQ ID NO 180
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (3)..(3)
<223> OTHER INFORMATION: D-Leu

<400> SEQUENCE: 180

Lys Ala Leu Asn Arg Gln Leu Gly Val Ala Ala
1               5                   10

<210> SEQ ID NO 181
<211> LENGTH: 11
```

```
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (4)..(4)
<223> OTHER INFORMATION: D-Asn

<400> SEQUENCE: 181

Lys Ala Leu Asn Arg Gln Leu Gly Val Ala Ala
1               5                   10

<210> SEQ ID NO 182
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (5)..(5)
<223> OTHER INFORMATION: D-Arg

<400> SEQUENCE: 182

Lys Ala Leu Asn Arg Gln Leu Gly Val Ala Ala
1               5                   10

<210> SEQ ID NO 183
<211> LENGTH: 11
<212> TYPE: PRT
<213> ORGANISM: Unknown
<220> FEATURE:
<223> OTHER INFORMATION: Description of Unknown: Mammalian
      sequence

<400> SEQUENCE: 183

Lys Ala Leu Asn Arg Gln Leu Gly Val Ala Ala
1               5                   10

<210> SEQ ID NO 184
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Val

<400> SEQUENCE: 184

Lys Ala Leu Asn Arg Gln Leu Gly Val Ala Ala
1               5                   10

<210> SEQ ID NO 185
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (9)..(9)
```

```
<223> OTHER INFORMATION: D-Val

<400> SEQUENCE: 185

Lys Ala Leu Asn Arg Gln Leu Gly Val Ala Ala
1               5                   10

<210> SEQ ID NO 186
<211> LENGTH: 4
<212> TYPE: PRT
<213> ORGANISM: Unknown
<220> FEATURE:
<223> OTHER INFORMATION: Description of Unknown: Mammalian
      sequence

<400> SEQUENCE: 186

Lys Lys Lys Ala
1

<210> SEQ ID NO 187
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (6)..(6)
<223> OTHER INFORMATION: Any amino acid

<400> SEQUENCE: 187

Lys Ala Leu Asn Arg Xaa Leu Gly Val Ala Ala
1               5                   10

<210> SEQ ID NO 188
<211> LENGTH: 11
<212> TYPE: PRT
<213> ORGANISM: Unknown
<220> FEATURE:
<223> OTHER INFORMATION: Description of Unknown: Mammalian
      sequence
<220> FEATURE:
<221> NAME/KEY: MOD_RES
<222> LOCATION: (7)..(7)
<223> OTHER INFORMATION: D-Gln

<400> SEQUENCE: 188

Lys Ala Leu Asn Arg Gln Gln Gly Val Ala Ala
1               5                   10

<210> SEQ ID NO 189
<211> LENGTH: 32
<212> TYPE: PRT
<213> ORGANISM: Unknown
<220> FEATURE:
<223> OTHER INFORMATION: Description of Unknown: Mammalian
      sequence

<400> SEQUENCE: 189

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
            20                  25                  30

<210> SEQ ID NO 190
<211> LENGTH: 12
<212> TYPE: PRT
<213> ORGANISM: Unknown
<220> FEATURE:
```

-continued

<223> OTHER INFORMATION: Description of Unknown: Mammalian
      sequence

<400> SEQUENCE: 190

Tyr Gly Arg Lys Lys Lys Arg Gln Arg Arg
1               5                   10

<210> SEQ ID NO 191
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 191

Trp Leu Arg Arg Ile Lys Ala Trp Leu Arg Arg Ile Lys Ala Leu Ala
1               5                   10                  15

Arg Gln Leu Ala Val Ala
            20

<210> SEQ ID NO 192
<211> LENGTH: 22
<212> TYPE: PRT
<213> ORGANISM: Unknown
<220> FEATURE:
<223> OTHER INFORMATION: Description of Unknown: Mammalian
      sequence

<400> SEQUENCE: 192

His Arg Arg Ile Lys Ala Trp Leu Lys Lys Ile Leu Ala Leu Ala Arg
1               5                   10                  15

Gln Leu Gly Val Ala Ala
            20

<210> SEQ ID NO 193
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES

```
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
```

```
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
```

```
<222> LOCATION: (59)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 193

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent

<400> SEQUENCE: 194

Xaa Xaa Xaa Xaa Xaa Xaa Xaa Xaa Xaa Xaa Xaa
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
```

```
<222> LOCATION: (2)..(2)
<223> OTHER INFORMATION: Any amino acid
<220> FEATURE:
<221> NAME/KEY: MOD_RES
<222> LOCATION: (3)..(4)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (6)..(6)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid

<400> SEQUENCE: 195

Xaa Xaa Xaa Xaa Xaa Xaa Xaa
1               5

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(4)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (6)..(6)
<223> OTHER INFORMATION: Any basic amino acid

<400> SEQUENCE: 196

Xaa Xaa Xaa Xaa Xaa Xaa
1               5

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(4)
<223> OTHER INFORMATION: Any basic amino acid
<220> FEATURE:
<221> NAME/KEY: MOD_RES
```

```
<222> LOCATION: (5)..(5)
<223> OTHER INFORMATION: Any hydrophobic amino acid

<400> SEQUENCE: 197

Xaa Xaa Xaa Xaa Xaa
1               5

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Any basic amino acid
<220> FEATURE:
<221> NAME/KEY: MOD_RES
<222> LOCATION: (4)..(4)
<223> OTHER INFORMATION: Any hydrophobic amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any hydrophobic amino acid

<400> SEQUENCE: 198

Xaa Xaa Xaa Xaa Xaa Xaa
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid, His or Asn
<220> FEATURE:
<221> NAME/KEY: MOD_RES
<222> LOCATION: (2)..(3)
<223> OTHER INFORMATION: Any basic amino acid
<220> FEATURE:
<221> NAME/KEY: MOD_RES
<222> LOCATION: (4)..(4)
<223> OTHER INFORMATION: Any hydrophobic amino acid
<220> FEATURE:
<221> NAME/KEY: MOD_RES
<222> LOCATION: (5)..(5)
<223> OTHER INFORMATION: Any basic amino acid

<400> SEQUENCE: 199

Xaa Xaa Xaa Xaa Xaa
1               5

<210> SEQ ID NO 200
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Any basic amino acid
<220> FEATURE:
<221> NAME/KEY: MOD_RES
<222> LOCATION: (4)..(4)
<223> OTHER INFORMATION: Any hydrophobic amino acid

<400> SEQUENCE: 200

Xaa Xaa Xaa Xaa
1

<210> SEQ ID NO 201
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(4)
<223> OTHER INFORMATION: Any basic amino acid

<400> SEQUENCE: 201

Xaa Xaa Xaa Xaa
1

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any basic amino acid
<220> FEATURE:
<221> NAME/KEY: MOD_RES
<222> LOCATION: (4)..(5)
<223> OTHER INFORMATION: Any hydrophobic amino acid

<400> SEQUENCE: 202

Xaa Xaa Xaa Xaa Xaa
1               5

<210> SEQ ID NO 203
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any basic amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any hydrophobic amino acid

<400> SEQUENCE: 203

Xaa Xaa Xaa Xaa
1

<210> SEQ ID NO 204
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any basic amino acid
<220> FEATURE:
<221> NAME/KEY: MOD_RES
<222> LOCATION: (4)..(4)
<223> OTHER INFORMATION: Any hydrophobic amino acid

<400> SEQUENCE: 204

Xaa Xaa Xaa Xaa
1

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any basic amino acid
<220> FEATURE:
<221> NAME/KEY: MOD_RES
<222> LOCATION: (3)..(4)
<223> OTHER INFORMATION: Any hydrophobic amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any hydrophobic amino acid

<400> SEQUENCE: 205
```

Xaa Xaa Xaa Xaa Xaa Xaa
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any basic amino acid
<220> FEATURE:
<221> NAME/KEY: MOD_RES
<222> LOCATION: (3)..(4)
<223> OTHER INFORMATION: Any hydrophobic amino acid
<220> FEATURE:
<221> NAME/KEY: MOD_RES
<222> LOCATION: (5)..(5)
<223> OTHER INFORMATION: Any basic amino acid

<400> SEQUENCE: 206

Xaa Xaa Xaa Xaa Xaa
1               5

<210> SEQ ID NO 207
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any basic amino acid
<220> FEATURE:
<221> NAME/KEY: MOD_RES
<222> LOCATION: (3)..(4)
<223> OTHER INFORMATION: Any hydrophobic amino acid

<400> SEQUENCE: 207

Xaa Xaa Xaa Xaa
1

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(3)
<223> OTHER INFORMATION: Any hydrophobic amino acid
<220> FEATURE:
<221> NAME/KEY: MOD_RES
<222> LOCATION: (4)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any hydrophobic amino acid

<400> SEQUENCE: 208

Xaa Xaa Xaa Xaa Xaa Xaa

-continued

```
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(3)
<223> OTHER INFORMATION: Any hydrophobic amino acid
<220> FEATURE:
<221> NAME/KEY: MOD_RES
<222> LOCATION: (4)..(5)
<223> OTHER INFORMATION: Any basic amino acid

<400> SEQUENCE: 209

Xaa Xaa Xaa Xaa Xaa
1               5

<210> SEQ ID NO 210
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(3)
<223> OTHER INFORMATION: Any hydrophobic amino acid
<220> FEATURE:
<221> NAME/KEY: MOD_RES
<222> LOCATION: (4)..(4)
<223> OTHER INFORMATION: Any basic amino acid

<400> SEQUENCE: 210

Xaa Xaa Xaa Xaa
1

<210> SEQ ID NO 211
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any hydrophobic amino acid, His, Asn, any amino
      acid or any basic amino acid
<220> FEATURE:
<221> NAME/KEY: MOD_RES
<222> LOCATION: (4)..(4)
<223> OTHER INFORMATION: Any hydrophobic amino acid, any amino acid or
      any basic amino acid
<220> FEATURE:
<221> NAME/KEY: MOD_RES
<222> LOCATION: (5)..(6)
<223> OTHER INFORMATION: Any hydrophobic amino acid or any basic amino
      acid
<220> FEATURE:
<221> NAME/KEY: MOD_RES
<222> LOCATION: (7)..(7)
```

<223> OTHER INFORMATION: Any hydrophobic amino acid
<220> FEATURE:
<221> NAME/KEY: misc_feature
<222> LOCATION: (1)..(7)
<223> OTHER INFORMATION: This region may encompass 4 to 7 residues in
      length
<220> FEATURE:
<221> NAME/KEY: MOD_RES
<222> LOCATION: (8)..(10)
<223> OTHER INFORMATION: Any hydrophobic amino acid, His, Asn, any amino
      acid or any basic amino acid
<220> FEATURE:
<221> NAME/KEY: MOD_RES
<222> LOCATION: (11)..(11)
<223> OTHER INFORMATION: Any hydrophobic amino acid, any amino acid or
      any basic amino acid
<220> FEATURE:
<221> NAME/KEY: MOD_RES
<222> LOCATION: (12)..(13)
<223> OTHER INFORMATION: Any hydrophobic amino acid or any basic amino
      acid
<220> FEATURE:
<221> NAME/KEY: MOD_RES
<222> LOCATION: (14)..(14)
<223> OTHER INFORMATION: Any hydrophobic amino acid
<220> FEATURE:
<221> NAME/KEY: misc_feature
<222> LOCATION: (8)..(14)
<223> OTHER INFORMATION: This region may encompass 4 to 7 residues in
      length
<220> FEATURE:
<221> NAME/KEY: MOD_RES
<222> LOCATION: (15)..(15)
<223> OTHER INFORMATION: Any amino acid except Lys or absent
<220> FEATURE:
<221> NAME/KEY: MOD_RES
<222> LOCATION: (16)..(16)
<223> OTHER INFORMATION: Any amino acid or absent
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (19)..(19)
<223> OTHER INFORMATION: Any basic amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (25)..(25)
<223> OTHER INFORMATION: Any amino acid or absent
<220> FEATURE:
<223> OTHER INFORMATION: see specification as filed for detailed
      description of substitutions and preferred embodiments

<400> SEQUENCE: 211

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 212
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES

```
<222> LOCATION: (2)..(2)
<223> OTHER INFORMATION: Any hydrophobic amino acid, His or Asn
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
```

```
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
```

<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any hydrophobic amino acid, His or Asn
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 212

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

<210> SEQ ID NO 213
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent -continued

```
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
```

```
        acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
        any basic amino acid
<220> FEATURE:
<221> NAME/KEY: MOD_RES
<222> LOCATION: (37)..(38)
<223> OTHER INFORMATION: Any hydrophobic amino acid or any basic amino
        acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
        present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
        acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
        any basic amino acid
<220> FEATURE:
<221> NAME/KEY: MOD_RES
<222> LOCATION: (44)..(45)
<223> OTHER INFORMATION: Any hydrophobic amino acid or any basic amino
        acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
        present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
        acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
        any basic amino acid
<220> FEATURE:
<221> NAME/KEY: MOD_RES
<222> LOCATION: (51)..(52)
<223> OTHER INFORMATION: Any hydrophobic amino acid or any basic amino
        acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
        present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
```

```
<220> FEATURE:
<221> NAME/KEY: MOD_RES
<222> LOCATION: (59)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 213

Xaa Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Ala Xaa Xaa Xaa Xaa Xaa Xaa Xaa Xaa Xaa
    50                  55                  60

<210> SEQ ID NO 214
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(3)
<223> OTHER INFORMATION: Any hydrophobic amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
```

```
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
```

-continued

```
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Any hydrophobic amino acid
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(63)
<223> OTHER INFORMATION: Any amino acid
<220> FEATURE:
<221> NAME/KEY: MOD_RES
```

```
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 214

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
        50                  55                  60

<210> SEQ ID NO 215
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(3)
<223> OTHER INFORMATION: Leu, Ile, Val or Met
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
```

```
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
```

-continued

```
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Leu, Ile, Val or Met
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
```

```
<220> FEATURE:
<223> OTHER INFORMATION: see specification as filed for detailed
      description of substitutions and preferred embodiments

<400> SEQUENCE: 215

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 216
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(3)
<223> OTHER INFORMATION: Gln, Ala or Asn
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
```

-continued

```
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
```

```
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Gln, Ala or Asn
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 216
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 217
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Gln or Asn
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
```

```
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
```

```
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(59)
<223> OTHER INFORMATION: His or Asn
<220> FEATURE:
<221> NAME/KEY: MOD_RES
<222> LOCATION: (60)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 217

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
        50                  55              60

<210> SEQ ID NO 218
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
```

```
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
```

```
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (60)..(60)
<223> OTHER INFORMATION: Any hydrophobic amino acid
<220> FEATURE:
<221> NAME/KEY: MOD_RES
<222> LOCATION: (61)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 218

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
```

```
                    20                  25                  30
Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
        50                  55                  60
```

```
<210> SEQ ID NO 219
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Leu, Ile, Val or Met
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
```

-continued

```
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
```

-continued

```
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (60)..(60)
<223> OTHER INFORMATION: Leu, Ile, Val or Met
<220> FEATURE:
<221> NAME/KEY: MOD_RES
<222> LOCATION: (61)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 219

Xaa Xaa Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 220
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (8)..(8)
<223> OTHER INFORMATION: Gly, Ala, Cys, Ser, Thr or Tyr
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
<220> FEATURE:
<221> NAME/KEY: MOD_RES -continued

```
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
<223> OTHER INFORMATION: Any hydrophobic amino acid, any amino acid or
      any basic amino acid
```

```
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (61)..(61)
<223> OTHER INFORMATION: Gly, Ala, Cys, Ser, Thr or Tyr
<220> FEATURE:
<221> NAME/KEY: MOD_RES
<222> LOCATION: (62)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 220
```

-continued

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 221
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length
```

-continued

```
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
```

-continued

```
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(61)
<223> OTHER INFORMATION: Any amino acid
<220> FEATURE:
<221> NAME/KEY: MOD_RES
<222> LOCATION: (62)..(62)
<223> OTHER INFORMATION: Any hydrophobic amino acid
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments
```

<400> SEQUENCE: 221

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 222
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (9)..(9)
<223> OTHER INFORMATION: Leu, Ile, Val or Met
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)

```
<223> OTHER INFORMATION: This region may encompass 4 to 7 residues in
      length
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
```

```
<221> NAME/KEY: MOD_RES
<222> LOCATION: (43)..(43)
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(61)
<223> OTHER INFORMATION: Any amino acid
<220> FEATURE:
<221> NAME/KEY: MOD_RES
<222> LOCATION: (62)..(62)
<223> OTHER INFORMATION: Leu, Ile, Val or Met
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
``` description of substitutions and preferred embodiments

<400> SEQUENCE: 222

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 223
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: misc_feature
<222> LOCATION: (1)..(11)
<223> OTHER INFORMATION: This region may or may not be present
<220> FEATURE:
<221> NAME/KEY: MOD_RES
<222> LOCATION: (12)..(14)
<223> OTHER INFORMATION: Any hydrophobic amino acid, His, Asn, any amino
      acid or any basic amino acid
<220> FEATURE:
<221> NAME/KEY: MOD_RES
<222> LOCATION: (15)..(15)
<223> OTHER INFORMATION: Any hydrophobic amino acid, any amino acid or
      any basic amino acid
<220> FEATURE:
<221> NAME/KEY: MOD_RES
<222> LOCATION: (16)..(17)
<223> OTHER INFORMATION: Any hydrophobic amino acid or any basic amino
      acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: misc_feature
<222> LOCATION: (12)..(18)
<223> OTHER INFORMATION: This region may encompass 4 to 7 residues in
      length

```
<220> FEATURE:
<221> NAME/KEY: MOD_RES
<222> LOCATION: (19)..(21)
<223> OTHER INFORMATION: Any hydrophobic amino acid, His, Asn, any amino
      acid or any basic amino acid
<220> FEATURE:
<221> NAME/KEY: MOD_RES
<222> LOCATION: (22)..(22)
<223> OTHER INFORMATION: Any hydrophobic amino acid, any amino acid or
      any basic amino acid
<220> FEATURE:
<221> NAME/KEY: MOD_RES
<222> LOCATION: (23)..(24)
<223> OTHER INFORMATION: Any hydrophobic amino acid or any basic amino
      acid
<220> FEATURE:
<221> NAME/KEY: MOD_RES
<222> LOCATION: (25)..(25)
<223> OTHER INFORMATION: Any hydrophobic amino acid
<220> FEATURE:
<221> NAME/KEY: misc_feature
<222> LOCATION: (19)..(25)
<223> OTHER INFORMATION: This region may encompass 4 to 7 residues in
      length
<220> FEATURE:
<221> NAME/KEY: MOD_RES
<222> LOCATION: (26)..(28)
<223> OTHER INFORMATION: Any hydrophobic amino acid, His, Asn, any amino
      acid or any basic amino acid
<220> FEATURE:
<221> NAME/KEY: MOD_RES
<222> LOCATION: (29)..(29)
<223> OTHER INFORMATION: Any hydrophobic amino acid, any amino acid or
      any basic amino acid
<220> FEATURE:
<221> NAME/KEY: MOD_RES
<222> LOCATION: (30)..(31)
<223> OTHER INFORMATION: Any hydrophobic amino acid or any basic amino
      acid
<220> FEATURE:
<221> NAME/KEY: MOD_RES
<222> LOCATION: (32)..(32)
<223> OTHER INFORMATION: Any hydrophobic amino acid
<220> FEATURE:
<221> NAME/KEY: misc_feature
<222> LOCATION: (26)..(32)
<223> OTHER INFORMATION: This region may or may not be present and if
      present may encompass 4 to 7 residues in length
<220> FEATURE:
<221> NAME/KEY: MOD_RES
<222> LOCATION: (33)..(35)
<223> OTHER INFORMATION: Any hydrophobic amino acid, His, Asn, any amino
      acid or any basic amino acid
<220> FEATURE:
<221> NAME/KEY: MOD_RES
<222> LOCATION: (36)..(36)
<223> OTHER INFORMATION: Any hydrophobic amino acid, any amino acid or
      any basic amino acid
<220> FEATURE:
<221> NAME/KEY: MOD_RES
<222> LOCATION: (37)..(38)
<223> OTHER INFORMATION: Any hydrophobic amino acid or any basic amino
      acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: misc_feature
<222> LOCATION: (33)..(39)
<223> OTHER INFORMATION: This region may or may not be present and if
      present may encompass 4 to 7 residues in length
<220> FEATURE:
<221> NAME/KEY: MOD_RES
<222> LOCATION: (40)..(42)
<223> OTHER INFORMATION: Any hydrophobic amino acid, His, Asn, any amino
      acid or any basic amino acid
<220> FEATURE:
<221> NAME/KEY: MOD_RES
<222> LOCATION: (43)..(43)
```

```
<223> OTHER INFORMATION: Any hydrophobic amino acid, any amino acid or
      any basic amino acid
<220> FEATURE:
<221> NAME/KEY: MOD_RES
<222> LOCATION: (44)..(45)
<223> OTHER INFORMATION: Any hydrophobic amino acid or any basic amino
      acid
<220> FEATURE:
<221> NAME/KEY: MOD_RES
<222> LOCATION: (46)..(46)
<223> OTHER INFORMATION: Any hydrophobic amino acid
<220> FEATURE:
<221> NAME/KEY: misc_feature
<222> LOCATION: (40)..(46)
<223> OTHER INFORMATION: This region may or may not be present and if
      present may encompass 4 to 7 residues in length
<220> FEATURE:
<221> NAME/KEY: MOD_RES
<222> LOCATION: (47)..(49)
<223> OTHER INFORMATION: Any hydrophobic amino acid, His, Asn, any amino
      acid or any basic amino acid
<220> FEATURE:
<221> NAME/KEY: MOD_RES
<222> LOCATION: (50)..(50)
<223> OTHER INFORMATION: Any hydrophobic amino acid, any amino acid or
      any basic amino acid
<220> FEATURE:
<221> NAME/KEY: MOD_RES
<222> LOCATION: (51)..(52)
<223> OTHER INFORMATION: Any hydrophobic amino acid or any basic amino
      acid
<220> FEATURE:
<221> NAME/KEY: MOD_RES
<222> LOCATION: (53)..(53)
<223> OTHER INFORMATION: Any hydrophobic amino acid
<220> FEATURE:
<221> NAME/KEY: misc_feature
<222> LOCATION: (47)..(53)
<223> OTHER INFORMATION: This region may or may not be present and if
      present may encompass 4 to 7 residues in length
<220> FEATURE:
<221> NAME/KEY: MOD_RES
<222> LOCATION: (54)..(54)
<223> OTHER INFORMATION: Any amino acid except Lys or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (58)..(58)
<223> OTHER INFORMATION: Any basic amino acid
<220> FEATURE:
<221> NAME/KEY: MOD_RES
<222> LOCATION: (59)..(61)
<223> OTHER INFORMATION: Any amino acid
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (64)..(64)
<223> OTHER INFORMATION: Any amino acid or absent
<220> FEATURE:
<221> NAME/KEY: misc_feature
<222> LOCATION: (54)..(64)
<223> OTHER INFORMATION: This region may or may not be present
<220> FEATURE:
<223> OTHER INFORMATION: see specification as filed for detailed
      description of substitutions and preferred embodiments

<400> SEQUENCE: 223

Xaa Xaa Xaa Xaa Xaa Xaa Xaa Xaa Val Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Val Xaa Xaa
    50                  55                  60

<210> SEQ ID NO 224
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (3)..(4)
<223> OTHER INFORMATION: Any basic amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any basic amino acid
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (11)..(12)
<223> OTHER INFORMATION: Any basic amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (19)..(20)
<223> OTHER INFORMATION: Any basic amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(22)
<223> OTHER INFORMATION: Any basic amino acid
<220> FEATURE:
<221> NAME/KEY: MOD_RES
<222> LOCATION: (23)..(26)
<223> OTHER INFORMATION: Any amino acid
<220> FEATURE:
<221> NAME/KEY: MOD_RES
<222> LOCATION: (27)..(28)
<223> OTHER INFORMATION: Any basic amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
```

```
<222> LOCATION: (30)..(30)
<223> OTHER INFORMATION: Any basic amino acid
<220> FEATURE:
<221> NAME/KEY: MOD_RES
<222> LOCATION: (31)..(34)
<223> OTHER INFORMATION: Any amino acid
<220> FEATURE:
<221> NAME/KEY: MOD_RES
<222> LOCATION: (35)..(36)
<223> OTHER INFORMATION: Any basic amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (38)..(38)
<223> OTHER INFORMATION: Any basic amino acid
<220> FEATURE:
<221> NAME/KEY: MOD_RES
<222> LOCATION: (39)..(40)
<223> OTHER INFORMATION: Any amino acid
<220> FEATURE:
<221> NAME/KEY: misc_feature
<222> LOCATION: (1)..(40)
<223> OTHER INFORMATION: This sequence may encompass 2 to 5 "Xaa Xaa Xaa
      Xaa Xaa Xaa Xaa Xaa" repeats

<400> SEQUENCE: 224

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
        35                  40

<210> SEQ ID NO 225
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (3)..(4)
<223> OTHER INFORMATION: Lys, Arg or His
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Lys, Arg or His
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (11)..(12)
<223> OTHER INFORMATION: Lys, Arg or His
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Lys, Arg or His
<220> FEATURE:
```

```
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (19)..(20)
<223> OTHER INFORMATION: Lys, Arg or His
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(22)
<223> OTHER INFORMATION: Lys, Arg or His
<220> FEATURE:
<221> NAME/KEY: MOD_RES
<222> LOCATION: (23)..(26)
<223> OTHER INFORMATION: Any amino acid
<220> FEATURE:
<221> NAME/KEY: MOD_RES
<222> LOCATION: (27)..(28)
<223> OTHER INFORMATION: Lys, Arg or His
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (30)..(30)
<223> OTHER INFORMATION: Lys, Arg or His
<220> FEATURE:
<221> NAME/KEY: MOD_RES
<222> LOCATION: (31)..(34)
<223> OTHER INFORMATION: Any amino acid
<220> FEATURE:
<221> NAME/KEY: MOD_RES
<222> LOCATION: (35)..(36)
<223> OTHER INFORMATION: Lys, Arg or His
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (38)..(38)
<223> OTHER INFORMATION: Lys, Arg or His
<220> FEATURE:
<221> NAME/KEY: MOD_RES
<222> LOCATION: (39)..(40)
<223> OTHER INFORMATION: Any amino acid
<220> FEATURE:
<221> NAME/KEY: misc_feature
<222> LOCATION: (1)..(40)
<223> OTHER INFORMATION: This sequence may encompass 2 to 5 "Xaa Xaa Xaa
      Xaa Xaa Xaa Xaa Xaa" repeats

<400> SEQUENCE: 225

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
        35                  40

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Absent or is a transduction domain
```

```
<220> FEATURE:
<221> NAME/KEY: MOD_RES
<222> LOCATION: (2)..(5)
<223> OTHER INFORMATION: This region may encompass 1 to 4 residues
      selected from "Ala," "Lys Ala," "Lys Lys Ala," "Lys Lys Lys Ala"
      or "Arg Ala" or is absent
<220> FEATURE:
<221> NAME/KEY: MOD_RES
<222> LOCATION: (6)..(6)
<223> OTHER INFORMATION: An aliphatic amino acid, Gly, Leu, Ala, Val,
      Ile, Met, Tyr, Trp or Phe
<220> FEATURE:
<221> NAME/KEY: MOD_RES
<222> LOCATION: (7)..(7)
<223> OTHER INFORMATION: An aliphatic amino acid, Val, Leu, Ile, Ala,
      Gly, Gln, Asn, Ser, Thr or Cys
<220> FEATURE:
<221> NAME/KEY: MOD_RES
<222> LOCATION: (8)..(8)
<223> OTHER INFORMATION: Gln, Asn, His, Arg or Lys
<220> FEATURE:
<221> NAME/KEY: MOD_RES
<222> LOCATION: (9)..(9)
<223> OTHER INFORMATION: Gln or Asn
<220> FEATURE:
<221> NAME/KEY: MOD_RES
<222> LOCATION: (10)..(10)
<223> OTHER INFORMATION: An aliphatic amino acid, Cys, Ala, Gly, Leu,
      Val, Ile, Met, Tyr, Trp or Phe
<220> FEATURE:
<221> NAME/KEY: MOD_RES
<222> LOCATION: (11)..(11)
<223> OTHER INFORMATION: An aliphatic amino acid, Ser, Ala, Cys, Thr or
      Gly
<220> FEATURE:
<221> NAME/KEY: MOD_RES
<222> LOCATION: (12)..(12)
<223> OTHER INFORMATION: Val, Leu, Ile or Met
<220> FEATURE:
<221> NAME/KEY: MOD_RES
<222> LOCATION: (13)..(14)
<223> OTHER INFORMATION: Any amino acid or absent
<220> FEATURE:
<221> NAME/KEY: MOD_RES
<222> LOCATION: (15)..(15)
<223> OTHER INFORMATION: Absent or is a transduction domain
<220> FEATURE:
<223> OTHER INFORMATION: see specification as filed for detailed
      description of substitutions and preferred embodiments

<400> SEQUENCE: 226

Xaa Xaa Xaa Xaa Xaa Xaa Xaa Xaa Xaa Xaa Xaa Xaa Xaa Xaa Xaa
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Absent or is a transduction domain
<220> FEATURE:
<221> NAME/KEY: MOD_RES
<222> LOCATION: (2)..(5)
<223> OTHER INFORMATION: This region may encompass 1 to 4 residues
      selected from "Ala," "Lys Ala," "Lys Lys Ala," "Lys Lys Lys Ala"
      or "Arg Ala" or is absent
<220> FEATURE:
<221> NAME/KEY: MOD_RES
<222> LOCATION: (6)..(6)
<223> OTHER INFORMATION: Gly, Leu, Ala, Val, Ile, Met, Tyr, Trp or Phe
<220> FEATURE:
<221> NAME/KEY: MOD_RES
<222> LOCATION: (7)..(7)
```

```
<223> OTHER INFORMATION: An aliphatic amino acid, Val, Leu, Ile, Ala,
      Gly, Gln, Asn, Ser, Thr or Cys
<220> FEATURE:
<221> NAME/KEY: MOD_RES
<222> LOCATION: (8)..(8)
<223> OTHER INFORMATION: Gln, Asn, His, Arg or Lys
<220> FEATURE:
<221> NAME/KEY: MOD_RES
<222> LOCATION: (9)..(9)
<223> OTHER INFORMATION: Gln or Asn
<220> FEATURE:
<221> NAME/KEY: MOD_RES
<222> LOCATION: (10)..(10)
<223> OTHER INFORMATION: An aliphatic amino acid, Cys, Ala, Gly, Leu,
      Val, Ile, Met, Tyr, Trp or Phe
<220> FEATURE:
<221> NAME/KEY: MOD_RES
<222> LOCATION: (11)..(11)
<223> OTHER INFORMATION: An aliphatic amino acid, Ser, Ala, Cys, Thr or
      Gly
<220> FEATURE:
<221> NAME/KEY: MOD_RES
<222> LOCATION: (12)..(12)
<223> OTHER INFORMATION: Val, Leu, Ile or Met
<220> FEATURE:
<221> NAME/KEY: MOD_RES
<222> LOCATION: (13)..(14)
<223> OTHER INFORMATION: Any amino acid or absent
<220> FEATURE:
<221> NAME/KEY: MOD_RES
<222> LOCATION: (15)..(15)
<223> OTHER INFORMATION: Absent or is a transduction domain
<220> FEATURE:
<223> OTHER INFORMATION: see specification as filed for detailed
      description of substitutions and preferred embodiments

<400> SEQUENCE: 227

Xaa Xaa Xaa Xaa Xaa Xaa Xaa Xaa Xaa Xaa Xaa Xaa Xaa Xaa Xaa
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Absent or is a transduction domain
<220> FEATURE:
<221> NAME/KEY: MOD_RES
<222> LOCATION: (2)..(5)
<223> OTHER INFORMATION: This region may encompass 1 to 4 residues
      selected from "Ala," "Lys Ala," "Lys Lys Ala," "Lys Lys Lys Ala"
      or "Arg Ala" or is absent
<220> FEATURE:
<221> NAME/KEY: MOD_RES
<222> LOCATION: (6)..(6)
<223> OTHER INFORMATION: An aliphatic amino acid, Gly, Leu, Ala, Val,
      Ile, Met, Tyr, Trp or Phe
<220> FEATURE:
<221> NAME/KEY: MOD_RES
<222> LOCATION: (7)..(7)
<223> OTHER INFORMATION: Val, Leu, Ile, Ala, Gly, Gln, Asn, Ser, Thr or
      Cys
<220> FEATURE:
<221> NAME/KEY: MOD_RES
<222> LOCATION: (8)..(8)
<223> OTHER INFORMATION: Gln, Asn, His, Arg or Lys
<220> FEATURE:
<221> NAME/KEY: MOD_RES
<222> LOCATION: (9)..(9)
<223> OTHER INFORMATION: Gln or Asn
<220> FEATURE:
<221> NAME/KEY: MOD_RES
<222> LOCATION: (10)..(10)
```

<223> OTHER INFORMATION: An aliphatic amino acid, Cys, Ala, Gly, Leu,
      Val, Ile, Met, Tyr, Trp or Phe
<220> FEATURE:
<221> NAME/KEY: MOD_RES
<222> LOCATION: (11)..(11)
<223> OTHER INFORMATION: An aliphatic amino acid, Ser, Ala, Cys, Thr or
      Gly
<220> FEATURE:
<221> NAME/KEY: MOD_RES
<222> LOCATION: (12)..(12)
<223> OTHER INFORMATION: Val, Leu, Ile or Met
<220> FEATURE:
<221> NAME/KEY: MOD_RES
<222> LOCATION: (13)..(14)
<223> OTHER INFORMATION: Any amino acid or absent
<220> FEATURE:
<221> NAME/KEY: MOD_RES
<222> LOCATION: (15)..(15)
<223> OTHER INFORMATION: Absent or is a transduction domain
<220> FEATURE:
<223> OTHER INFORMATION: see specification as filed for detailed
      description of substitutions and preferred embodiments

<400> SEQUENCE: 228

Xaa Xaa Xaa Xaa Xaa Xaa Xaa Xaa Xaa Xaa Xaa Xaa Xaa Xaa Xaa
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Absent or is a transduction domain
<220> FEATURE:
<221> NAME/KEY: MOD_RES
<222> LOCATION: (2)..(5)
<223> OTHER INFORMATION: This region may encompass 1 to 4 residues
      selected from "Ala," "Lys Ala," "Lys Lys Ala," "Lys Lys Lys Ala"
      or "Arg Ala" or is absent
<220> FEATURE:
<221> NAME/KEY: MOD_RES
<222> LOCATION: (6)..(6)
<223> OTHER INFORMATION: An aliphatic amino acid, Gly, Leu, Ala, Val,
      Ile, Met, Tyr, Trp or Phe
<220> FEATURE:
<221> NAME/KEY: MOD_RES
<222> LOCATION: (7)..(7)
<223> OTHER INFORMATION: An aliphatic amino acid, Val, Leu, Ile, Ala,
      Gly, Gln, Asn, Ser, Thr or Cys
<220> FEATURE:
<221> NAME/KEY: MOD_RES
<222> LOCATION: (8)..(8)
<223> OTHER INFORMATION: Gln, Asn, His, Arg or Lys
<220> FEATURE:
<221> NAME/KEY: MOD_RES
<222> LOCATION: (9)..(9)
<223> OTHER INFORMATION: Gln or Asn
<220> FEATURE:
<221> NAME/KEY: MOD_RES
<222> LOCATION: (10)..(10)
<223> OTHER INFORMATION: Cys, Ala, Gly, Leu, Val, Ile, Met, Tyr, Trp or
      Phe
<220> FEATURE:
<221> NAME/KEY: MOD_RES
<222> LOCATION: (11)..(11)
<223> OTHER INFORMATION: An aliphatic amino acid, Ser, Ala, Cys, Thr or
      Gly
<220> FEATURE:
<221> NAME/KEY: MOD_RES
<222> LOCATION: (12)..(12)
<223> OTHER INFORMATION: Val, Leu, Ile or Met
<220> FEATURE:
<221> NAME/KEY: MOD_RES

```
<222> LOCATION: (13)..(14)
<223> OTHER INFORMATION: Any amino acid or absent
<220> FEATURE:
<221> NAME/KEY: MOD_RES
<222> LOCATION: (15)..(15)
<223> OTHER INFORMATION: Absent or is a transduction domain
<220> FEATURE:
<223> OTHER INFORMATION: see specification as filed for detailed
      description of substitutions and preferred embodiments

<400> SEQUENCE: 229

Xaa Xaa Xaa Xaa Xaa Xaa Xaa Xaa Xaa Xaa Xaa Xaa Xaa Xaa Xaa
1               5                   10                  15
```